United States Patent
Gupta et al.

(10) Patent No.: US 8,858,995 B2
(45) Date of Patent: Oct. 14, 2014

(54) METHODS AND COMPOSITIONS FOR CONTROLLED DELIVERY OF PHYTOCHEMICAL AGENTS

(75) Inventors: Ramesh C. Gupta, Louisville, KY (US); Manicka V. Vadhanam, Louisville, KY (US); Farrukh Aqil, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 13/429,601

(22) Filed: Mar. 26, 2012

(65) Prior Publication Data

US 2012/0231079 A1 Sep. 13, 2012

Related U.S. Application Data

(63) Continuation-in-part of application No. 12/401,175, filed on Mar. 10, 2009, now Pat. No. 8,172,806.

(60) Provisional application No. 61/035,153, filed on Mar. 10, 2008, provisional application No. 61/096,108, filed on Sep. 11, 2008.

(51) Int. Cl.
*A61K 9/26* (2006.01)
*A61K 47/40* (2006.01)
(Continued)

(52) U.S. Cl.
CPC ............. *A61K 9/0036* (2013.01); *A61K 47/40* (2013.01); *A61K 45/06* (2013.01); *A61K 31/121* (2013.01); *A61K 36/82* (2013.01); *A61K 31/05* (2013.01); *A61K 9/0024* (2013.01); *A61K 31/366* (2013.01); *A61K 36/235* (2013.01); *A61K 47/10* (2013.01); *A61K 47/34* (2013.01); *A61K 31/404* (2013.01); *A61K 31/01* (2013.01); *A61K 36/9066* (2013.01); *A61K 31/497* (2013.01)
USPC ........................................................ 424/469

(58) Field of Classification Search
None
See application file for complete search history.

(56) References Cited

U.S. PATENT DOCUMENTS

| 4,244,357 A | 1/1981 | Morrison |
| 4,702,917 A | 10/1987 | Schindler |

(Continued)

FOREIGN PATENT DOCUMENTS

| WO | 9962510 A2 | 12/1999 |
| WO | 0164214 A2 | 9/2001 |

OTHER PUBLICATIONS

Malins et al., "Progression of human breast cancers to the metastatic state is linked to hydroxyl radical-induced DNA damage," Proc Natl Acad Sci U S A, 93, 1996, pp. 2557-2563.

(Continued)

*Primary Examiner* — Anand Desai
*Assistant Examiner* — Melissa Mercier
(74) *Attorney, Agent, or Firm* — Stites & Harbison PLLC; Terry L. Wright

(57) ABSTRACT

Compositions are provided that comprises a biocompatible polymeric matrix incorporating an effective amount of a phytochemical agent, a combination of phytochemical agents, or a phytochemical agent and one or more additional therapeutic agents. Methods of treating a cancer using the compositions are further provided.

20 Claims, 49 Drawing Sheets

(51) Int. Cl.
*A61K 45/06* (2006.01)
*A61K 31/121* (2006.01)
*A61K 9/00* (2006.01)
*A61K 36/82* (2006.01)
*A61K 31/05* (2006.01)
*A61K 31/366* (2006.01)
*A61K 36/235* (2006.01)
*A61K 47/10* (2006.01)
*A61K 47/34* (2006.01)
*A61K 31/404* (2006.01)
*A61K 31/01* (2006.01)
*A61K 36/9066* (2006.01)
*A61K 31/497* (2006.01)

(56) References Cited

U.S. PATENT DOCUMENTS

| | | | |
|---|---|---|---|
| 5,651,986 | A | 7/1997 | Brem et al. |
| 6,190,591 | B1 * | 2/2001 | van Lengerich ............... 264/141 |
| 7,153,520 | B2 * | 12/2006 | Seo et al. ....................... 424/426 |
| 8,303,650 | B2 * | 11/2012 | Shokoohi ...................... 623/1.42 |
| 2003/0099709 | A1 * | 5/2003 | Shah et al. .................... 424/469 |
| 2003/0180352 | A1 | 9/2003 | Patel et al. |
| 2004/0033273 | A1 * | 2/2004 | Patwardhan et al. ......... 424/725 |
| 2005/0042293 | A1 | 2/2005 | Jackson et al. |
| 2005/0129731 | A1 | 6/2005 | Horres et al. |
| 2006/0079508 | A1 | 4/2006 | Falardeau et al. |
| 2006/0148877 | A1 | 7/2006 | Bernstein et al. |
| 2006/0193790 | A1 | 8/2006 | Doyle et al. |
| 2010/0076542 | A1 | 3/2010 | Orlowski |
| 2010/0086599 | A1 | 4/2010 | Huempel et al. |

OTHER PUBLICATIONS

Martinez-Tome et al., "Antioxidant properties of Mediterranean spices compared with common food additives," J Food Prot, 64, 2001, pp. 1412-1419.
McPherson et al., "Breast cancer-epidemiology, risk factors, and genetics," BMJ, 321, 2000, pp. 624-628.
Meyskens et al., "Diet and cancer: the disconnect between epidemiology and randomized clinical trials," Cancer Epidemiol Biomarkers Prev, 14, 2005, pp. 1366-1369.
Morse et al., "Cancer chemoprevention: principles and prospects," Carcinogenesis. 14, 1993, pp. 1737-1746.
Narod et al., "Prevention and management of hereditary breast cancer," J Clin Oncol. 23, 2005,,pp. 1656-1663.
O'Dwyer et al., "The chemopreventive agent oltipraz stimulates repair of damaged DNA," Cancer Res., 57, 1997, pp. 1050-1053.
Prall et al., "Estrogen regulation of cell cycle progression in breast cancer cells," J Steroid Biochem Mol Biol, 65, 1998, pp. 169-174.
Ramos et al., "DNA repair and breast carcinoma susceptibility in women," Cancer, 100, 2004, pp. 1352-1357.
Satyanarayana et al., "Antioxidant activity of the aqueous extracts of spicy food additives—evaluation and comparison with ascorbic acid in in-vitro systems," J Herb Pharmacother, 4, 2004, pp. 1-10.
Seeram et al., "Bioavailability of ellagic acid in human plasma after consumption of ellagitannins from pomegranate (*Punica granatum* L.) juice," Clin. Chim. Acta, 348, 2004, pp. 63-68.
Shull et al., "Ovary-intact, but not ovariectomized female ACI rats treated with 17β-estradiol rapidly develop mammary carcinoma," Carcinogenesis, 18, 1997, pp. 1595-1601.
Singletary et al., "Ellagic acid effects on the carcinogenicity, DNA-binding and metabolism of 7, 12-demethylbenzoanthracene (DMBA)," In Vivo, 3, 1989, pp. 173-175.
Smith et al., "Use of a microsome-mediated test system to assess efficacy and mechanisms of cancer chemopreventive agents," Carcinogenesis, 17, 1996, pp. 1285-1290.
Smith et al., "Determining efficacy of cancer chemopreventive agents using a cell-free system concomitant with DNA adduction," Mutat Res, 425, 1999, pp. 143-152.
Smith et al., "Effect of chemopreventive agents on microsome-mediated DNA adduction of the breast carcinogen dibenzo[a,l]pyrene," Mutat Res, 412, 1998, pp. 307-314.
Smith et al., "Effects of chemopreventive agents on DNA adduction induced by the potent mammary carcinogen dibenzo[a,l]pyrene in the human breast cells MCF-7," Mutat Res, 480-481, 2001), pp. 97-108.
Srinivasaan et al., "A Rapid Screening Assay for Antioxidant Potential of Natural and Synthetic Agents in vitro," Int J Oncol, 20, 2002, pp. 983-986.
Srivastave, KC., "Extracts from two frequently consumed spices-cumin and turmeric-inhibit platelet aggregation and alter eicosanoid biosynthesis in human blood platelets," Prostaglandins Leukot Essent Fatty Acids, 37, 1989, pp. 57-64.
Steinmetz et al., "Vegetables, fruit, and cancer," I. Epidemiology. Cancer Causes Control, 2, 1991, pp. 325-357.
Sun, Y, "Free radicals, antioxidant enzymes, and carcinogenesis," Free Radic Biol Med, 8, 1990, pp. 583-599.
Teel et al., Disposition of the plant Phenol ellagic acid in the mouse following oral administration by gavage, Xenobiotica, 18, 1988, pp. 397-405.
Todorovic et al., "Analysis of potential biomarkers of estrogen-initiated cancer in the urine of Syrian golden hamsters treated with 4-hydroxyestradiolm" Carcinogenesis. 22, 2001, pp. 905-911.
Turan et al, "The effects of steroidal estrogens in ACI rat mammary carcinogenesis: 17β-estradiol, 2-hydroxyestradiol, 4-hydroxyestradiol, 16α-hydroxyestradiol and 4-hydroxyestrone," J Endocrin, 183, 2004, pp. 91-99.
Uma Pradeep et al., "Common Indian spices: nutrient composition, consumption and contribution to dietary value," Plant Foods Hum Nutr, 44, 1993, pp. 137-148.
Vadhanam et al., "An improvised model for estrogen-mediated mammary tumors in aci rats," Proc Am Assoc Cancer Res, 47, 2006, Abst #1771.
Willett, WC, Diet and cancer, J Am Med Assoc, 293, 2006, pp. 233-234.
Yun et al., "Delphinidin, an anthocyanidin in pigmented fruits and vegetables, induces apoptosis and cell cycle arrest in human colon cancer HCT116 cells," Mol Carcinog, 48, 2009, pp. 260-270.
Zhang et al., "Dietary carotenoids and vitamins A, C, and E and risk of breast cancer," J. Natl. Cancer Inst, 91, 1999, ppc. 547-556.
ISA/US, International Search Report and Written Opinion for related international patent application No. PCT/US09136663, mailed Jul. 8, 2009.
EPO, Supplementary European Search Report for corresponding European Patent Application No. EP09719335, completed May 20, 2011.
Weinberg et al., "Antitumor efficacy and local distribution of doxorubicin via intratumoral delivery from polymer millirods," Journal of Biomedical Materials Research Part A, 2006, pp. 161-170.
Sung et al., "Controlled release of nalbuphine prodrugs from biodegradable polymeric matrices: influence of prodrug hydrophilicity and polymer composition," International Journal of Pharmaceutics, 1998, vol. 172, pp. 17-25.
Wang et al., "A mechanistic model of controlled drug release from polymer millirods: Effects of excipients and complex binding," Journal of Controlled Release, 2007, vol. 119, pp. 111-120.
Weinberg et al., "Polymer Implants for Intratumoral Drug Delivery and Cancer Therapy," Journal of Pharmaceutical Sciences, 2008, vol. 97:5, pp. 1681-1702.
Desai et al., "Effect of formulation parameters on 2-methoxyestradiol release from injectable cylindrical poly(DL-lactide-co-glycolide) implants," European Journala of Pharmaceutics and Biopharmaceutics, 2008, vol. 70, pp. 187-198.
Desai et al., "Formulation and Characterization of Injectable (DL-lactide-co-glycolide) Implants Loaded with N-Acetylcysteine, a MMP Inhibitor," Pharmaceutical Research, Mar. 2006, vol. 25:2, pp. 586-597.
Desai et al., Formulation and In Vitro-In Vivo Evaluation of Black Raspberry Extract-Loaded PLGA/PLA Injectable Millicylindrical Implants for Sustained Delivery of Chemopreventive Anthocyanins, Pharmaceutical Research, Apr. 2010, vol. 27:4, pp. 628-643.

(56) References Cited

OTHER PUBLICATIONS

Aqil et al., "Multi-layer polymeric implants for sustained release of chemopreventives," Cancer Letters, 2012, vol. 326, pp. 33-40.
Jeyabalan et al., "Sustained Overexpression of CYP1A1 and 1B1 and Steady Accumulation of DNA Adducts by Low-Dose, Continuous Exposure to Benzo[a]pyrene by Polymeric Implants," Chemical Research in Toxicology, 2011, vol. 24, pp. 1937-1943.
Gupta et al., "Contolled-release systemic delivery—a new concept in cancer chemoprevention," Carcinogenesis, 2012, vol. 33:8, pp. 1608-1615.
Bansal et al., Controlled systemic delivery by polymeric implants enhances tissue and plasma curcumin levels compared with oral administration, European Journal of Pharmaceutics and Biopharmaceutics, 2012, vol. 80, pp. 571-577.
Bansal et al., "Development and In Vitro-In Vivo Evaluation of Polymeric Implants for Continuous Systemic Delivery of Curcumin," Pharm Res, 2011, vol. 28, pp. 1121-1130.
Bansal et al., "Advanced Drug Delivery Systems of Curcumin for Cancer Chemoprevention," Cancer Prevention Research, 2011, vol. 4, pp. 1158-1171.
Bansal et al., "Curcumin implants for continuous systemic delivery: safety and biocompatibility," Drug Deliv and Transl Res, 2011, vol. 1, pp. 332-341.
Cao et al., Sustained Systemic Delivery of Green Tea Polyphenols by Polymeric Implants Significantly Diminishes Benzo[a]pyrene-induced DNA Adducts, Chemical Research in Toxicology, 2011, vol. 24, 877-886.
Aqil et al., "Enhanced activity of punicalagin delivered via polymeric implants against benzo[a]pyrene-induced DNA adducts," Mutation Research, 2012, vol. 743, pp. 59-66.
Exner et al., "Drug-eluting polymer implants in cancer therapy," Expert Opin Drug Deliv, 2008, vol. 5(7), pp. 775-788.
Harnish et al., "Beneficial effects of estrogen treatment in the HLA-B27 transgenic rat model of inflammatory bowel disease," Am J Physiol Gastrointest Liver Physiol, 286, 2004, pp. G118-G125.
Harvell et al., "Dietary energy restriction inhibits estrogen-induced mammary, but not pituitary, tumorigenesis in the ACI rat," Carcinogenesis, 23, 2002, pp. 161-169.
Hede, K., "Rexinoids may be ready for prime time in prevention, but challenges remain," J Natl Cancer Inst, 96, 2004, pp. 1807-1808.
Hemminki et al., "Implications of results of molecular epidemiology on DNA adducts, their repair and mutations for mechanisms of human cancer," IARC Sci Publ, 157, 2004, pp. 217-235.
Hemminiki, K., "DNA adducts in biomonitoring," J Occup Environ Med, 37, 1995, pp. 44-51.
Hennekens et al., "Lack of effect of long-term supplementation with beta carotene on the incidence of malignant neoplasms and cardiovascular disease," N Engl J Med, 334, 1996, pp. 1145-1149.
Hirose et al., "Chemoprevention of heterocyclic amine-induced mammary carcinogenesis in rats," Environ Mol Mutagen, 39(2-3), 2002, pp. 271-278.
Holtzman, S., "Retinyl acetate inhibits estrogen-induced mammary carcinogenesis in female ACI rats," Carcinogenesis, 9, 1988, pp. 305-307.
Imaida et al., "Lack of chemopreventive effects of lycopene and curcumin on experimental rat prostate carcinogenesis," Carcinogenesis, 22(3), 2001, pp. 467-472.
Jemal et al., "Cancer Statistics 2005," CA Cancer J Clin, 55, 2005, pp. 10-30.
Jemal et al., "Cancer statistics, 2006," CA Cancer J Clin, 56, 2006, pp. 106-130.
Hatcher et al.,"Curcumin: From ancient medicine to current clinical trials," Cell. Mol. Life Sci., 65, 2008, pp. 1631-1652.
Garcea et al., "Consumption of the putative chemopreventive agent curcumin by cancer patients: Assessment of curcumin levels in the colorectum and their pharmacodynamic consequences," Cancer Epidemiol. Biomarkers Prev., 14, 2005, pp. 120-125.
Dhillon et al., "Phase II trial of curcumin in patients with advanced pancreatic cancer," Clin. Cancer Res., 14, 2008, pp. 4491-4499.

Langer, "New methods of drug delivery," Science, 249, 1990, pp. 1527-1533.
Karp et al., "Development and therapeutic applications of advanced biomaterials," Current Opinion Biotech, 18, 2007, pp. 454-459.
Nair et al., "Polymers as biomaterials for tissue engineering and controlled drug delivery," Adv. Biochem. Engin/ Biotechnol., 102, 2006, pp. 47-90.
Gunatillake et al., "Biodegradable synthetic polymers for tissue engineering," Eur. Cells Materials, 5, 2003, pp. 1-16.
Saigal et al., "Site specific chronotherapeutic drug delivery systems: A patent review," Recent Patents Drug Delivery Formulation, 3, 2009, pp. 64-70.
Anal, "Time-controlled pulsative delivery systems for bioactive compounds," Recent Patents Drug Delivery Formulation, 1, 2007, pp. 73-79.
Urquhart, "Controlled drug delivery: therapeutic and pharmacological aspects," J Int. Med, 248, 2000, pp. 357-376.
Darney, "The role of hormonal contraceptives: Hormonal implants: Contraception for a new century," Am J Obst Gynecol, 170(5S), 1994, pp. 1536-1543.
Ma et al., "A biodegradable levonorgestrel-releasing implant made of PCL/F68 compound as tested in rats and dogs," Contraception, 74, 2006, pp. 141-147.
Cohen et al., "Silastic implants for delivery of oestradiol to mice," J Reprod Fertility, 99, 1993, pp. 219-223.
Dunn et al., "Sustained release of cisplatin in dogs from an injectable implant delivery system," J Bioactive Compatible Polymers, 11, 1996, pp. 286-300.
Weissleder et al., "Quantitation of slow drug release from an implantable and degradable gentamicin conjugate by in vivo magnetic resonance imaging," Antimicrob Agents Chemother, 39, 1995, pp. 839-845.
Ugalde et al., "Distribution of anthocyanins delivered from a bioadhesive black raspberry gel following topical intraoral application in normal healthy volunteers," Pharmc Res, 26, 2009, pp. 977-986.
Siddiqui et al., "Introducing nanochemoprevention as a novel approach for cancer control: Proof of principle with green tea polyphenol epigallocatechin-3-gallate," Cancer Res, 69, 2009, pp. 1712-1716.
Sweet, "The enigmatic cervix," Derm Clinics, 16, 1998, pp. 739-745.
Marrazzo et al., "Management of women with cervicitis," Clin Infect Dis, 44(S3), 2007, pp. S102-S110.
Lusk et al., "Cervicitis: a review," Curr Opinion Infect Dis, 21, 2008, pp. 49-55.
Mashburn, "Etiology, diagnosis and management of vaginitis," J Midwifery Womens Health, 51, 2006, pp. 423-430.
Angotti et al., "Vaginitis: Making sense of over-the-counter treatment options," Infec Dis Obst Gynecol, 2007, pp. 1-4.
Cullins et al., "Treating vaginitis," Nurse Practioner, 24, 1999, pp. 46-65.
Keskar et al., "Cervical cancer treatment with a locally insertable controlled release delivery system," J Controlled Release, 115, 2006, pp. 280-288.
Ruffin et al., Low-dose topical delivery of all-trans retinoic acid for cervical intraepithelial neoplasia II and III, Cancer Epidemiol Biomarkers Prey, 13, 2004, pp. 2148-2152.
Disilvestro et al., "Treatment of cervical intraepithelial neoplasia levels 2 and 3 with adapalene, a retinoid-related molecule," J Lower Genital Tract Dis, 5, 2001, pp. 33-37.
Catalone et al., "Mouse model of cervicovaginal toxicity and inflammation for preclinical evaluation of topical vaginal microbicides," Antimicrobial Agents Chemother, 48, 2004, pp. 1837-1847.
Das, "Investigation of the clearance of human papillomavirus infection in uterine cervix by Basant, a polyherba vaginal cream and curcumin," Institute of Cytology and Preventive Oncology, Annual Report 2003-2005, pp. 5-6.
Das Neves et al., "Gels as vaginal drug delivery systems," Int J Pharmaceutics, 318, 2006, pp. 1-14.
Kelloff et al., "Mechanistic considerations in chemopreventive drug development," J Cell Biochem Suppl, 20, 1994, pp. 1-24.

(56) References Cited

OTHER PUBLICATIONS

Kelloff et al., "Intermediate biomarkers of precancer and their application in chemoprevention," J. Cell. Biochem., (Suppl.) 16G, 1992, pp. 15-21.
Kelsey et al., "Epidemiology and Prevention of Breast Cancer," Annu Rev Pub Hlth, 17, 1996, pp. 47-67.
Kensler et al., "Development of cancer chemopreventive agents: oltipraz as a paradigm," Chem. Res. Toxicol., 12, 1999, pp. 113-126.
Li et al., "Carcinogenic activities of various steroidal and nonsteroidal estrogens in the hamster kidney: relation to hormonal activity and cell proliferation," Cancer Res, 55, 1995, pp. 4347-4351.
Li et al., "Ploidy differences between hormone- and chemical carcinogen-induced rat mammary neoplasms : comparison to invasive human ductal breast cancer," Mol Carcinogensis, 33, 2002, pp. 56-65.
Li et al., "Estrogen-induced breast cancer in female ACI rats," In: Hormonal Carcinogenesis (Eds. Li JJ, Daling JR and Li SA), vol. III, 2000, pp. 178-188, Springer-Verlag, NY.
Li et al., "Prevention of solely estrogen-induced mammary tumors in female ACI rats by tamoxifen: evidence for estrogen receptor mediation," J Endocrinol, 175, 2002, pp. 297-305.
Liehr, JG., "Is Estradiol a genotoxic mutagenic carcinogen?" Endocrine Rev, 21, 2000, pp. 40-54.
Lubet et al., "Efficacy of targretin on methylnitrosourea-induced mammary cancers: prevention and therapy dose response curves and effects on proliferation and apoptosis," Carcinogenesis, 26, 2005, pp. 441-448.
Aggarwal et al., "Suppression of the Nuclear Factor-κB Activation pathway by spice derived phytochemicals," Ann NY Acad Sci, 1030, 2004, pp. 434-441.
Aggarwal et al.,"Anticancer potential of curcumin: preclinical and clinical studies," Anticancer Res, 23, 2003, pp. 363-398.
Aggarwal et al., From chemoprevention to chemotherapy: common targets and common goals, Expert Opin Investig Drugs, 13, 2004, pp. 1327-1338.
Anderson et al., "Oestrogenic compounds and oxidative stress (in human sperm and lymphocytes in the Comet assay)," Mutat Res, 544, 2003, pp. 173-178.
Angele et al., "Altered expression of DNA double-strand break detection and repair proteins in breast carcinomas," Histopathology, 43, 2003, pp. 347-353.
Arif et al., "Artifactual formation of 8-oxo-2'-deoxyguanosine: role of fluorescent light and inhibitors," Oncol Rep, 10, 2003, pp. 2071-2074.
Arif et al., "Inhibition of cigarette smoke-related lipophilic DNA adducts in rat tissues by dietary oltipraz," Carcinogenesis, 19, 1998, pp. 515-1517.
Arif et al., Inhibition of cigarette smoke-related DNA adducts in rat tissues by indole-3-carbinol. Mutat Res, 452, 2000, pp. 11-18.
Banerjee et al., "Suppression of 7,12-Dimethylbenz(a)anthracene-induced Mammary Carcinogenesis in Rats by Resveratrol: Role of Nuclear Factor-κB, Cyclooxygenase 2, and Matrix Metalloprotease 9," Cancer Res, 62, 2002, pp. 4945-4954.
Beach et al., "Human biomonitoring and the 32P-postlabeling assay (Commentary)," Carcinogenesis, 13, 1992, pp. 1053-1074.
Bendich, A. "Carotenoids and the immune response," J Nutr, 119, 1989, pp. 112-115.
Bernstein et al., "Endogenous hormones and breast cancer risk," Epidemiol Rev, 15, 1993, pp. 48-65.
Berwick et al., "Markers of DNA repair and susceptibility to cancer in humans: an epidemiologic review," J. Natl Cancer Inst, 92, 2000, pp. 874-897.
Bettuzzi et al., "Chemoprevention of human prostate cancer by oral administration of green tea catechins in volunteers with high-grade prostate intraepithelial neoplasia: a preliminary report from a one-year proof-of-principle study," Cancer Res, 66, 2006, pp. 1234-1240.
Blot et al., "Nutrition intervention trials in Linxian, China: supplementation with specific vitamin/mineral combinations, cancer incidence, and disease-specific mortality in the general population," J Natl Cancer Inst, 85, 1993, pp. 1483-1492.
Bolton et al., "Role of quinoids in estrogen carcinogenesis," Chem Res Toxicol, 11, 1998, pp. 1113-1127.
Bolton et al., "Role of quinones in toxicology," Chem Res Toxicol, 13, 2000, pp. 135-160.
Borek, C., "Dietary antioxidants and human cancer," Integr Cancer Ther, 3, 2004, pp. 333-341.
Braithwaite et al., "Repair of DNA lesions induced by polycyclic aromatic hydrocarbons in human cell-free extracts: involvement of two excision repair mechanisms in vitro," Carcinogenesis, 19, 1998, pp. 1239-1246.
Carolin et al., "Prevention of breast cancer," Critical Rev Oncol Hemat, 33, 2000, pp. 221-238.
Castagnetta et al., "Gas chromatography/mass spectrometry of catechol estrogens," Steroids, 57, 1992, pp. 437-443.
Cavalieri et al., "Estrogens as endogenous genotoxic agents—DNA adducts and mutations," J Nat Cancer Inst Monogr, 27, 2000, pp. 75-93.
Chadwick et al., "Identification of pathway-selective estrogen receptor ligands that inhibit NF-κB transcriptional activity," PNAS USA, 102, 2005, pp. 2543-2548.
Chaudhary et al., "Detection of endogenous malondialdehyde-deoxyguanosine adducts in human liver," Science, 265, 1994, pp. 1580-1582.
Chithra et al., "*Coriandrum sativum*—effect on lipid metabolism in 1,2-dimethyl hydrazine induced colon cancer," J Ethnopharm, 71, 2000, pp. 457-463.
Clapper et al., "Glutathione S-transferases-biomarkers of cancer risk and chemopreventive response," Chem Biol Interact, 111-122, 1998, pp. 377-388.
Clapper, ML, "Chemopreventive activity of oltipraz," Pharmacol. Ther., 78, 1998, pp. 17-27.
Cribb et al., "Role of polymorphic human cytochrome P450 enzymes in estrone oxidation," Cancer Epidemiol Biomarkers Prey, 15, 2006, pp. 551-558.
Devanesan et al., "Catechol estrogen metabolites and conjugates in mammary tumors and hyperplastic tissue from estrogen receptor-alpha knock-out (ERKO)/Wnt-1 mice: Implications for initiation of mammary tumors," Carcinogenesis, 22, 2001, pp. 1573-1576.
Dickson et al., "Growth factors in breast cancer," Endocr Rev, 16, 1995, pp. 559-589.
Digianni et al., "Complementary and alternative medicine use among women with breast cancer," J Clin Oncol, 20, 2002, pp. 34s-38s.
Dorai et al., "Role of chemopreventive agents in cancer therapy," Cancer Lett, 215, 2004, pp. 129-140.
Dunnick et al., "Chemically-induced mammary gland cancer in the National Toxicology Program's carcinogenesis assay," Carcinogenesis, 16, 1995, pp. 173-179.
El-Bayoumy, K., "Evaluation of chemopreventive agents against breast cancer and proposed strategies for future clinical intervention trials," Carcinogenesis, 15, 1994, pp. 2395-2420.
Elliott et al., "Measurement of cellular repair activities for oxidative DNA damage," Free Rad. Biol. Med., 28, 2000, pp. 1438-1446.
Evans et al., "Estrogen receptors alpha and beta have similar activities in multiple endothelial cell pathways," Endocrinology, 143, 2002, pp. 3785-3795.
Ferruzzi et al., "Analysis of Lycopene geometrical isomers in viological microsamples by liquid chromatography with coulombic array detection," J. Chromatogr. B., 760, 2001, pp. 289-299.
Foley et al., "Comparison of proliferating cell nuclear antigen to tritiated thymidine as a marker of proliferating hepatocytes in rats," Environ Health Perspect, 101, 1993, pp. 199-206.
Gagandeep et al., "Chemopreventive effects of cuminum cyminum in chemically induced forestomach and uterine cervix tumors in murine model systems," Nutr Cancer, 47, 2003, pp. 171-180.
Garg et al., "Interception of reactive, DNA adduct forming metabolites present in rodent serum following carcinogen exposure. Implication for use of body fluids in biomonitoring," Teratogenesis, carcinogenesis and Mutagenesis, 13, 1993, pp. 151-166.
Giovannucci, E., "Tomatoes, tomato-based products, lycopene, and cancer: review of the epidemiological literature," J. Natl Cancer Inst, 91, 1999, pp. 317-331.

(56) References Cited

OTHER PUBLICATIONS

Greenlee et al., "Cancer statistics," CA-Cancer J Clin, 51, 2001, pp. 15-36.

Greenwald et al., "Chemoprevention," CA-Cancer J Clin 45, 1995, pp. 31-49.

Grilli, S., "Tamoxifen (TAM): the dispute goes on," Ann 1st Super Sanita, 42, 2006, pp. 170-173.

Gupta et al., "Enhancement of pre-existing DNA adducts in rodents exposed to cigarette smoke," Mut. Res., 424, 1999, pp. 195-205.

Gupta et al., "Background DNA damage from endogenous and unavoidable exogenous carcinogens: a basis for spontaneous cancer incidence?," Mutat Res, 424, 1999, pp. 1-8.

Gupta et al., "32P-Postlabeling analysis of non-radioactive aromatic carcinogen-DNA adducts," Carcinogenesis, 3, 1982, pp. 1081-1092.

Gupta, R.C., "Enhanced sensitivity of 32P-postlabeling analysis of aromatic carcinogen-DNA adducts," Cancer Res, 45, 1985, pp. 5656-5662.

Hampton T., "Clinical trials point to complexities of chemoprevention for cancer," J Am Med Assoc, 294, 2005, pp. 29-31.

IP Australia, Patent Examination Report No. 1 issued in related Australian application No. 2009223653, issued Jul. 8, 2013.

ISA/KR, International Search Report and Written Opinion issued in related international application No. PCT/US2013/033877, mailed Jul. 2, 2013.

* cited by examiner

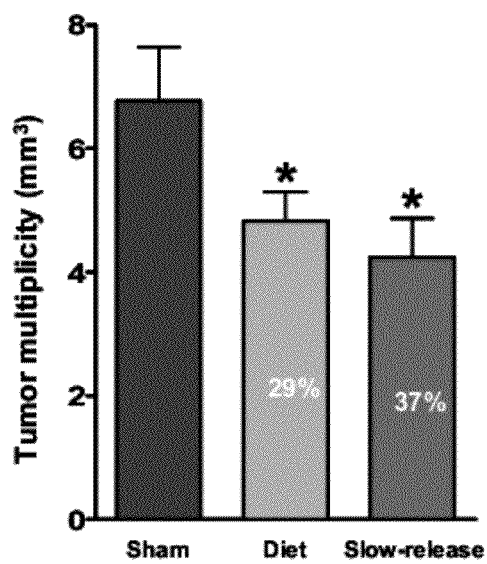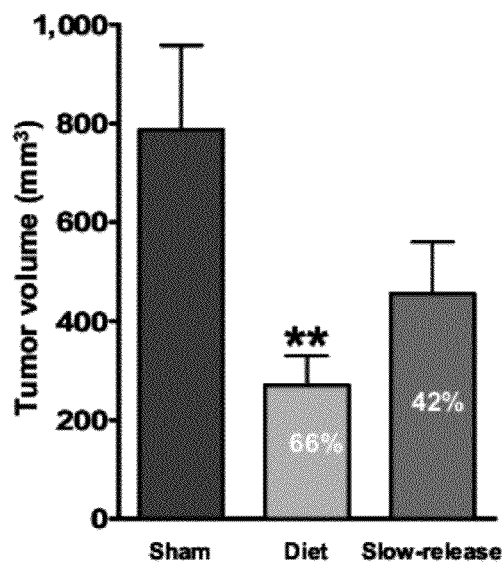
FIGURE 24A                    FIGURE 24B

METHODS AND COMPOSITIONS FOR CONTROLLED DELIVERY OF PHYTOCHEMICAL AGENTS

RELATED APPLICATIONS

This application is a continuation-in-part of U.S. application Ser. No. 12/401,175, filed Mar. 10, 2009, which claims priority from U.S. Provisional Application Ser. No. 61/035,153, filed Mar. 10, 2008, and U.S. Application Ser. No. 61/096,108, filed Sep. 11, 2008, all of which are incorporated herein by this reference.

GOVERNMENT INTEREST

This invention was made with U.S. Government support under Grant Numbers CA-90892, CA-118114, and CA-125152 awarded by the National Institutes of Health. The government has certain rights in the invention.

TECHNICAL FIELD

The presently-disclosed subject matter relates to methods and compositions for the controlled delivery of phytochemical agents. In particular, the presently-disclosed subject matter relates to methods and compositions for treating cancer wherein a phytochemical agent is incorporated into and released in a controlled manner from a biocompatible and biodegradable polymeric matrix.

BACKGROUND

Despite recent advances in cancer detection and treatment strategies, cancer continues to contribute significantly to human mortality and remains second only to heart disease as the leading cause of death in the United States. In 2008 there were an estimated 565,650 deaths from cancer and each year about 1,437,180 new cases of cancer are diagnosed. Among those, lung cancer, breast cancer, and cervical cancer are among the most significant. For example, lung cancer remains the leading cause of cancer death in men and women, resulting in more than 215,000 new cases a year and over 161,000 deaths each year. Similarly, breast cancer and cervical cancer continue to be significant causes of cancer death in women with estimates of over 40,000 and over 3,500 women dying each year from breast and cervical cancer, respectively.

Overall, the survival rate for cancer has risen in recent years, but designing effective treatment strategies for cancer patients still represents a major challenge. In this regard, it has become increasingly clear that the problem of cancer mortality cannot be solved by treatment alone, but must also be approached from a prophylactic standpoint. Intervention with compounds of natural origin, such as phytochemical agents, is considered one such effective means to not only treat cancer, but also to prophylactically address cancer development. However, many of the same problems that are encountered with the administration of traditional chemotherapeutic agents are also encountered with these compounds of natural origin.

Typically, chemotherapeutic agents are administered orally or intravenously in bolus doses to elicit a response. Oral delivery of the chemotherapeutic agents often presents a bioavailability problem, as a large part of the agents is destroyed in the gut and the remainder is, at least in part, detoxified during first pass in the liver. Systemic delivery overcomes this hurdle, but this route of administration often leads to undesirable dose spikes. Moreover, a major limitation of both oral and intravenous delivery of traditional chemotherapeutic agents is that high doses of the agents are usually required in order to achieve an effective tissue or plasma concentration, but the high doses generally result in undesirable toxicity.

Accordingly, there remains a need in the art for methods and compositions for the delivery of compounds of natural origin in controlled low doses over extended periods of time. In particular, there remains a need in the art for methods and compositions for delivering low doses of phytochemical agents in a sustained manner such that phytochemical agents can effectively be used to address cancer mortality from both a therapeutic and prophylactic standpoint.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments of the presently-disclosed subject matter, a composition is provided that comprises a biocompatible polymeric matrix incorporating an effective amount of a phytochemical agent. In some embodiments, the composition is capable of releasing a controlled low dose of the phytochemical agent over a time period. In some embodiments, the time period is at least about 18 months.

In some embodiments of the presently-disclosed subject matter, the biocompatible polymeric matrix comprises a polymer that can be selected from polycaprolactone, cyclodextrin, F68, polyethylene glycol, and combinations thereof. In some embodiments, the biocompatible polymeric matrix is comprised of polycaprolactone in combination with a second polymer that, in some embodiments, can be selected from cyclodextrin, F68, and polyethylene glycol. In some embodiments, the polycaprolactone is combined with the second polymer in a ratio of about 4:1 or about 9:1 to form the biocompatible polymeric matrix. In some embodiments, the biocompatible polymeric matrix comprises polycaprolactone and F68 in a ratio of about 4:1. In some embodiments, the biocompatible polymeric matrix comprises polycaprolactone and polyethylene glycol in a ratio of about 65:35. In some embodiments, the biocompatible matrix is biodegradable.

With regard to the phytochemical agents that are incorporated into the biocompatible polymeric matrices of the presently-disclosed subject matter, in some embodiments, the phytochemical agent comprises about 2% to about 50% of the weight of the polymer or polymers forming the biocompatible polymeric matrix. In some embodiments, the phytochemical agent is selected from curcumin, green tea polyphenols, punicalagin, diindolylmethane, oltipraz, tocotrienol, tocopherol, plumbagin, cyanidin, delphinidin, lycopene, lupeol, curcurbitacin-B, Withaferin A, indole-3-carbinol, genestein, equol, resveratrol, co-enzyme Q-10, ellagic acid, petunidin, malvidin, peonidin, fennel extract, and combinations thereof.

In some embodiments, the phytochemical agent incorporated into the biocompatible polymeric matrix is a combination of one or more individual phytochemical agents. In some embodiments, the phytochemical agent is a combination of: oltipraz and curcumin; curcumin, ellagic acid, co-enzyme Q-10, and lycopene; curcumin, green tea polyphenols, diindolylmethane, and punicalagin; delphinidin, petunidin, malvidin, peonidin, and cyanidin; or punicalagin and delphinidin. In some embodiments, each phytochemical agent can be incorporated into the same biocompatible polymeric matrix or, in some embodiments, each phytochemical agent one or more additional biocompatible polymeric matrices such that the one or more additional biocompatible polymeric matrices each incorporate a single phytochemical agent. In some embodiments, a second biocompatible matrix is provided that incorporates at least one phytochemical agent.

In some embodiments, the compositions of the presently-disclosed subject matter can further comprise an effective amount of an anti-inflammatory agent or an effective amount of a chemotherapeutic agent. In some embodiments, the anti-inflammatory agents and the chemotherapeutic agents are incorporated into the same biocompatible polymeric matrix that also incorporates a phytochemical agent. In some embodiments, the anti-inflammatory agents and the chemotherapeutic agents are incorporated into a second biocompatible polymeric matrix.

In some embodiments of the presently-disclosed compositions, the compositions further include a polymeric coating that surrounds the biocompatible polymeric matrix that incorporates an effective amount of the phytochemical agent. In some embodiments, the polymeric coating is comprised of polycaprolactone. In some embodiments, the polymeric coating comprises one or more layers, such as, in some embodiments, about 5 to about 40 layers. In some embodiments, the biocompatible polymeric matrix itself, which incorporates the effective amount of the phytochemical agents, is provided in the form of a coating such that the compositions of the presently-disclosed subject matter can be utilized as a coating for additional compositions.

Further provided, in some embodiments of the presently-disclosed subject matter, are methods for treating a cancer. In some embodiments, a method for treating a cancer is provided that comprises administering to a subject in need thereof an effective amount of a composition comprising a biocompatible polymeric matrix incorporating a phytochemical agent, where the phytochemical agent is incorporated into and released over a time period from the biocompatible polymeric matrix at a controlled low dose of the phytochemical agent. In some embodiments, the time period is at least about 18 months.

In some embodiments, a method of treating a cancer is provided that further comprises administering an effective amount of an anti-inflammatory agent or a chemotherapeutic agent that is incorporated into and released over a time period from the biocompatible polymeric matrix or a second biocompatible polymeric matrix.

In some embodiments of the presently-disclosed methods for treating a cancer, the cancer is selected from breast cancer, lung cancer, or cervical cancer. In some embodiments, the subject is at an increased risk of developing a primary cancer, which, in some embodiments, is breast cancer, lung cancer, or cervical cancer. In some embodiments, the subject is at an increased risk of developing a secondary cancer.

In some embodiments, a method for treating a cancer is provided wherein a phytochemical agent is administered to a subject by subcutaneous implantation of a biocompatible matrix incorporating a phytochemical agent. In some embodiments, the phytochemical agent is administered by implantation of a biocompatible polymeric matrix incorporating that phytochemical agent at a site distant from the site of the cancer. In some embodiments, the implantation occurs at a site of a cancer or at a site suspected of developing a cancer.

Still further provided, in some embodiments of the presently-disclosed subject matter, is a device for insertion into a cervical canal. In some embodiments, the device comprises: a substantially cylindrical shaft having a proximal end and a distal end, and defining a canal that extends from the proximal end to the distal end; and, a cap attached to the proximal end of the cylindrical shaft that includes a central opening in registry with the canal defined by the shaft. In some embodiments, the device is comprised of a biocompatible polymeric matrix incorporating an effective amount of a phytochemical agent in accordance with the presently-disclosed subject matter.

In some embodiments, a device is provided where the cylindrical shaft is suitably adapted for engaging the walls of a cervical canal and where a bottom surface of the cap is suitably adapted for engaging an external orifice of a uterus. In some embodiments, a device is provided where the canal defined by the cylindrical shaft allows for the passage of bodily fluids from the uterus.

In some embodiments of the device for cervical insertion, the bottom surface of the cap has a concave shape such that the bottom surface of the cap suitably engages an external orifice of the uterus. In some embodiments, a device for cervical insertion is provided where the distal end of the cylindrical shaft is tapered. In some embodiments, a device for cervical insertion is provided where the cylindrical shaft is about 19 to about 25 mm in length and about 9 to 11 mm in diameter; the cap is about 20 to about 25 mm in diameter; and, the canal is about 4 mm to about 5 mm in diameter.

Advantages of the presently-disclosed subject matter will become evident to those of ordinary skill in the art after a study of the description, Figures, and non-limiting Examples in this document.

BRIEF DESCRIPTION OF THE DRAWINGS

FIG. 2 includes graphs depicting the release of curcumin from a biocompatible polymeric matrix in vitro.

FIG. 3 includes graphs depicting the release of green tea polyphenols (GTPs) from a biocompatible polymeric matrix in vitro.

FIG. 4 includes graphs depicting the release of diindolylmethane (DIM) from a biocompatible polymeric matrix in vitro.

FIG. 5 includes graphs depicting the release of punicalagins from a biocompatible polymeric matrix in vitro.

FIG. 6 includes graphs depicting the release of oltipraz from a biocompatible polymeric matrix in vitro.

FIG. 7 includes graphs depicting the release of lycopene from a biocompatible polymeric matrix in vitro.

FIG. 8 includes graphs depicting the release of resveratrol from a biocompatible polymeric matrix in vitro.

FIG. 9 includes graphs depicting the effect of incorporating various loads of curcumin into a biocompatible polymeric matrix in vitro, including incorporating 2% w/w of curcumin (♦), 5% w/w of curcumin (※), and 20% w/w of curcumin (▲) into separate biocompatible polymeric matrices.

FIG. 10 includes graphs depicting the effect of incorporating various loads of GTPs into a biocompatible polymeric matrix in vitro, including incorporating 1% w/w of GTPs (♦), 2.5% w/w of GTPs (※), 5% w/w of GTPs (▲), and 10% w/w of GTPs (※) into a separate biocompatible polymeric matrices comprised of polycaprolactone, MW 65K polymers and polycaprolactone, MW 15K polymers that were combined in a 1:4 ratio.

FIG. 13 includes graphs depicting the long-term in vivo release of curcumin from a biocompatible polymeric matrix.

FIG. 14 includes graphs depicting the long-term in vivo release of GTPs from a biocompatible polymeric matrix.

15B is a graph depicting the cumulative release of DIM from a biocompatible polymeric matrix where the total amount (mg) of DIM released (y-axis) and the total percentage of DIM released (y-axis) are plotted against a treatment period measured in weeks (x-axis).

Figure 16A:
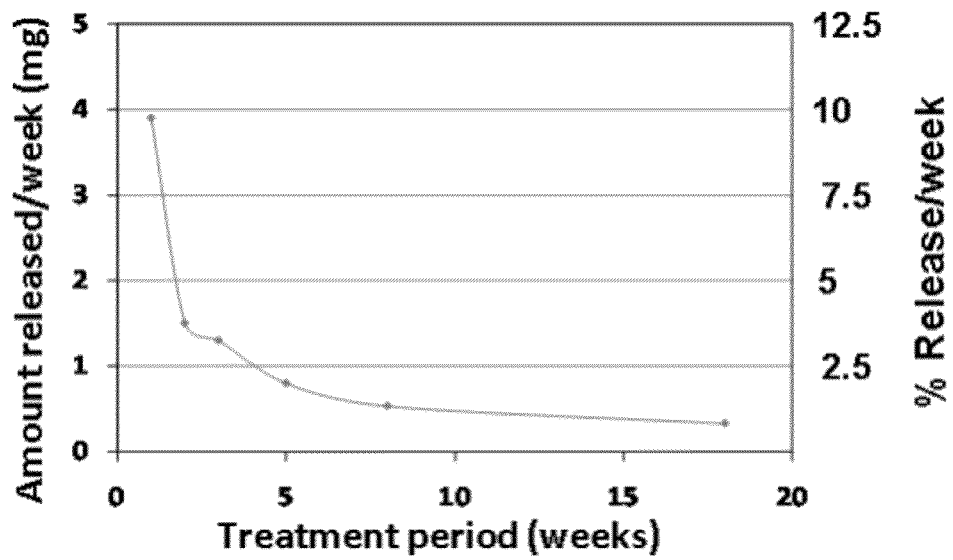
Figure 16B:
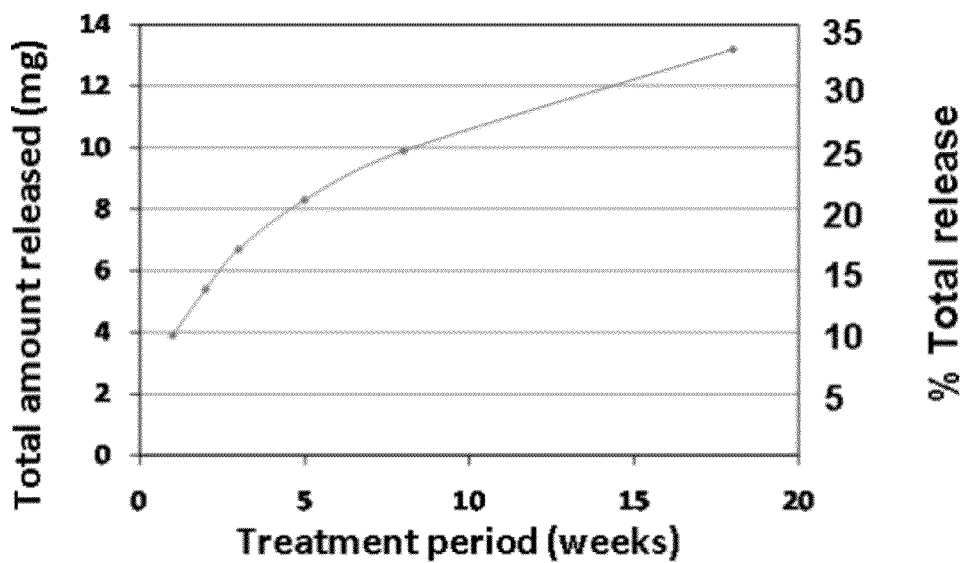

FIG. 16 includes graphs depicting the long-term in vivo release of punicalagins from a biocompatible polymeric matrix. FIG. 16A is a graph depicting the daily release of punicalagins from a biocompatible polymeric matrix where the total amount (mg) of punicalagins released per week (y-axis) and the total percentage of punicalagins released per week (y-axis) from the matrix are plotted against a treatment period measured in weeks (x-axis). FIG. 16B is a graph depicting the cumulative release of punicalagins from a biocompatible polymeric matrix where the total amount (mg) of punicalagins released (y-axis) and the total percentage of punicalagins released (y-axis) are plotted against a treatment period measured in weeks (x-axis).

Figure 17:
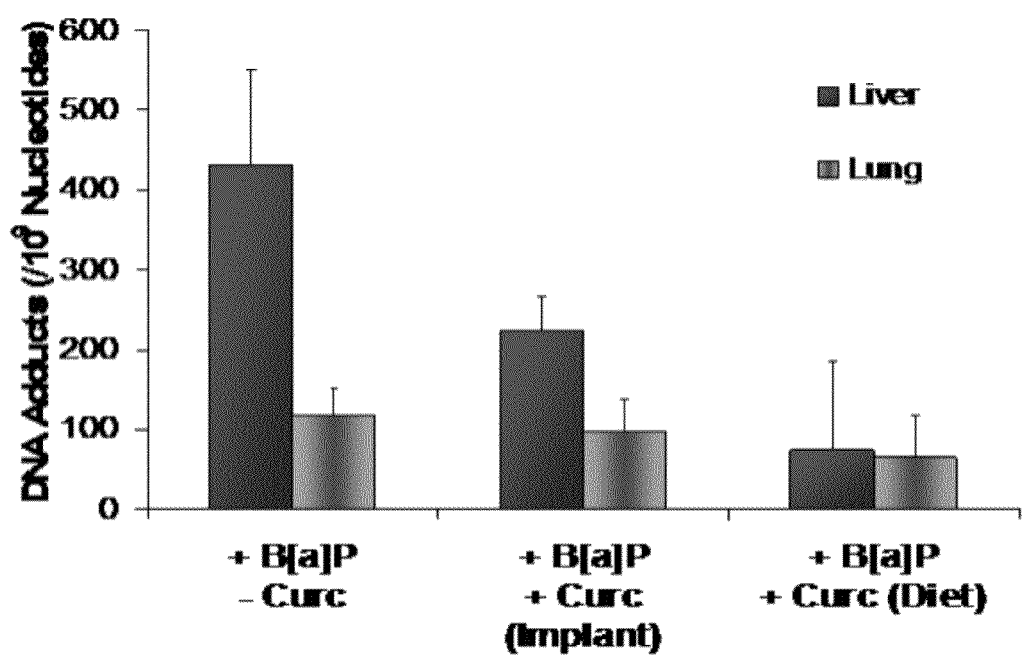

FIG. 17 is a graph depicting the effect of curcumin, administered by subcutaneous implantation of a biocompatible polymeric matrix incorporating 20% w/w curcumin or by diet, on the formation of DNA adducts in liver and lung tissue of rats treated with a single bolus dose of benzo[a]pyrene.

Figure 18:
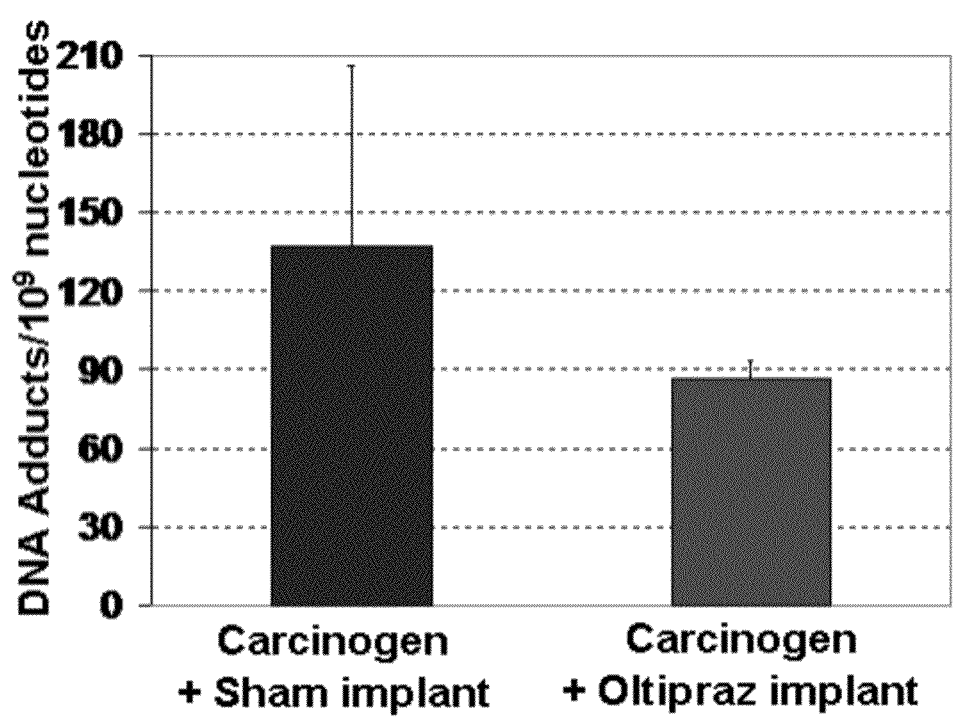

FIG. 18 is a graph depicting the effect of oltipraz, administered by subcutaneous implantation of a biocompatible polymeric matrix incorporating 10% w/w oltipraz, on the formation of DNA adducts in liver tissue of rats treated with a bolus dose of dibenzo[a,1]pyrene.

Figure 19:
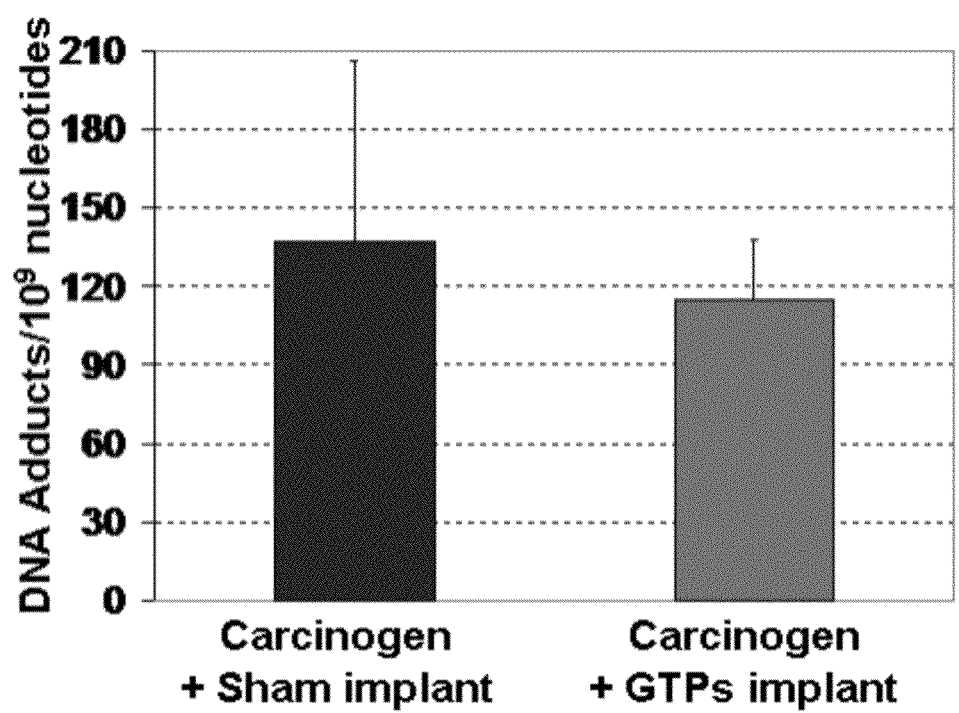

FIG. 19 is a graph depicting the effect of GTPs, administered by subcutaneous implantation of a biocompatible polymeric matrix incorporating 10% w/w GTPs, on the formation of DNA adducts in liver tissue of rats treated with a bolus dose of dibenzo[a,1]pyrene.

Figure 20:
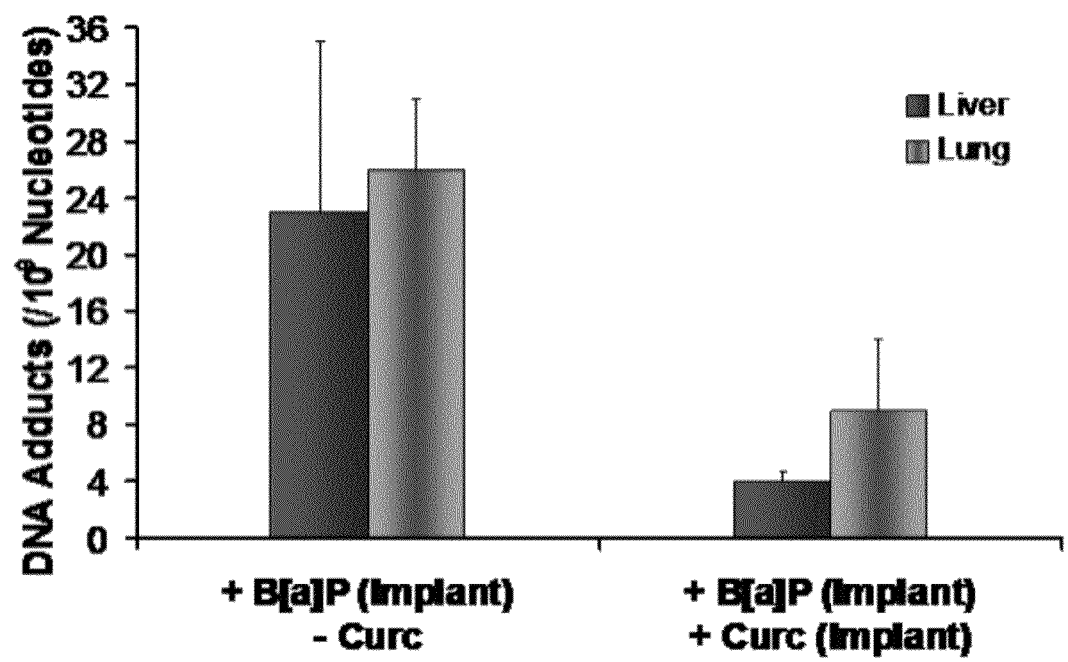

FIG. 20 is a graph depicting the effect of curcumin, administered by subcutaneous implantation of a 1 cm biocompatible polymeric matrix incorporating 20% w/w curcumin, on the formation of DNA adducts in liver and lung tissue of rats treated with a sustained low dose of benzo[a]pyrene.

Figure 21:
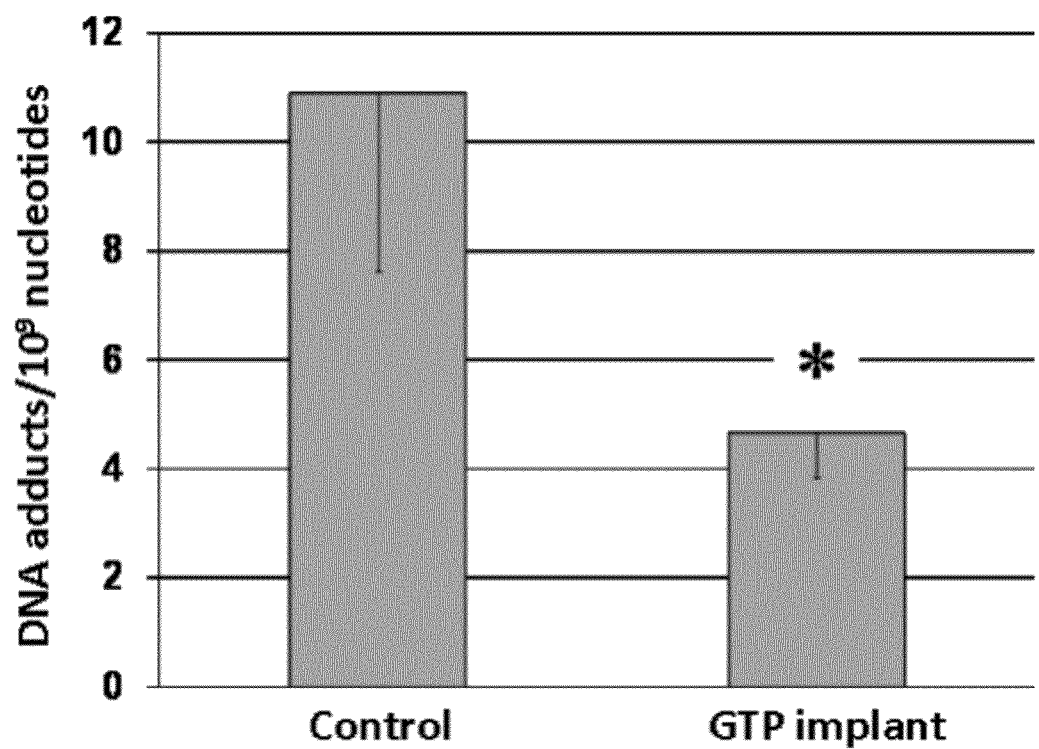

FIG. 21 is a graph depicting the effect of GTPs, administered by subcutaneous implantation of two 2-cm biocompatible polymeric matrices incorporating 10% w/w GTPs, on the formation of DNA adducts in liver tissue of rats treated with a sustained low dose of benzo[a]pyrene.

Figure 22A:
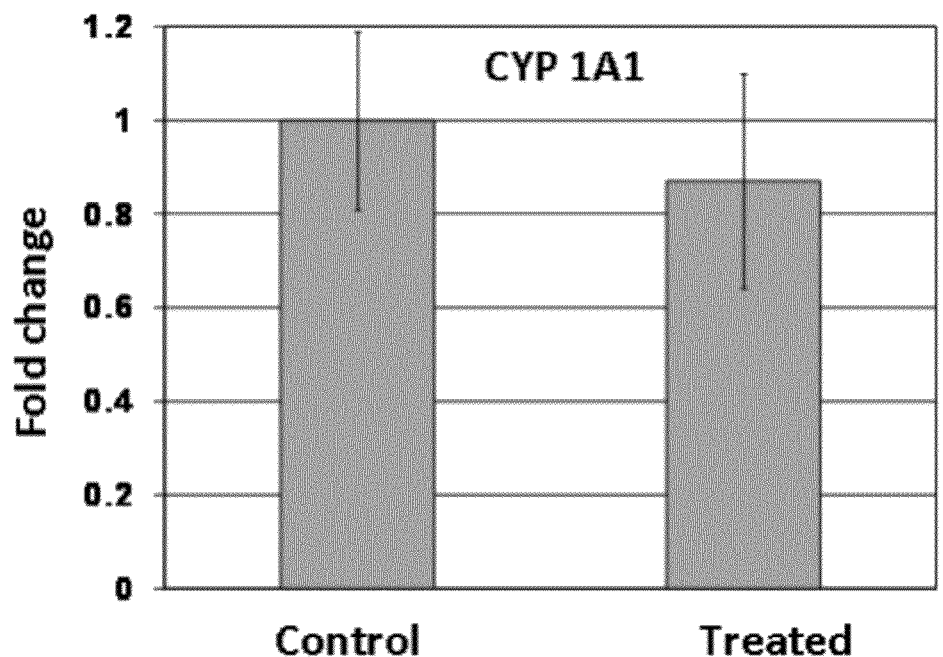
Figure 22B:
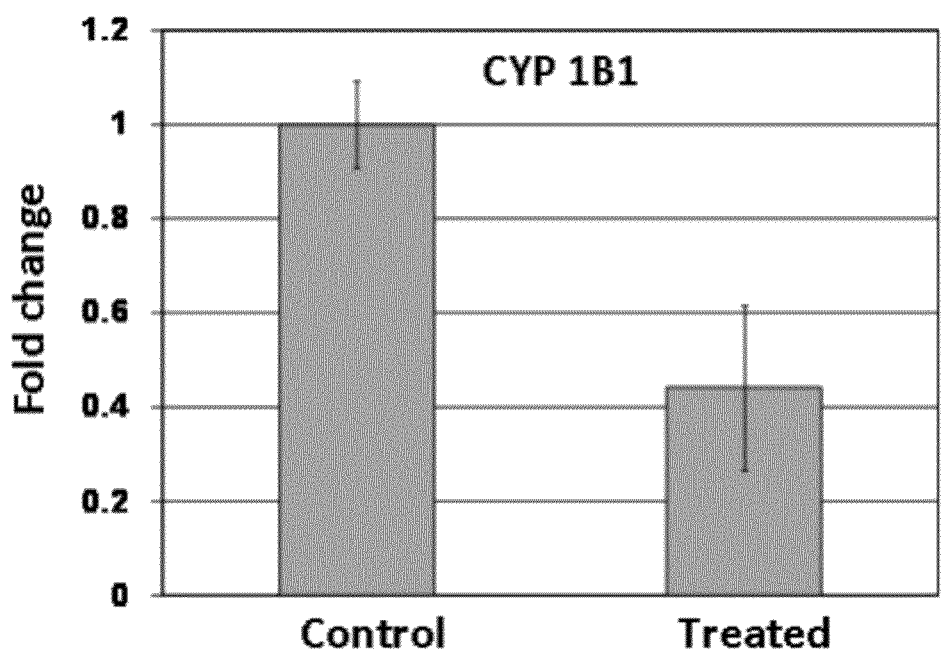

FIG. 22 includes graphs depicting the effect of GTPs, administered by subcutaneous implantation of two 2-cm biocompatible polymeric matrices incorporating 10% w/w GTPs, on expression of various cytochrome P450 (CYP) mRNA in liver tissue of rats treated with a sustained low dose of benzo[a]pyrene. FIG. 22A is a graph depicting the effect of GTPs on the expression of CYP 1A1. FIG. 22B is a graph depicting the effect of GTPs on the expression of CYP 1B1.

Figure 23A:
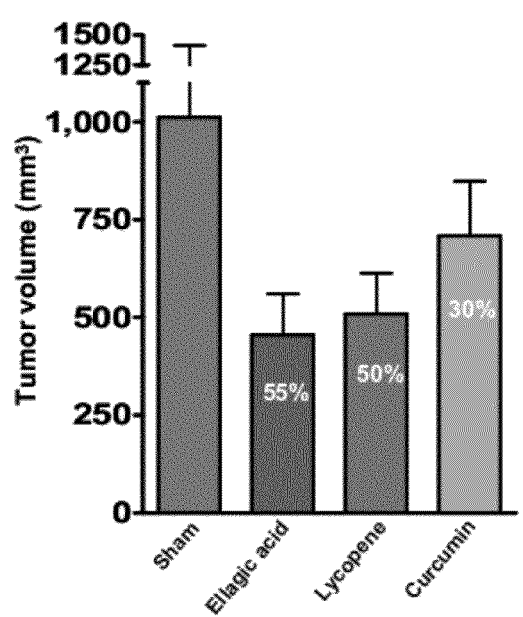
Figure 23B:
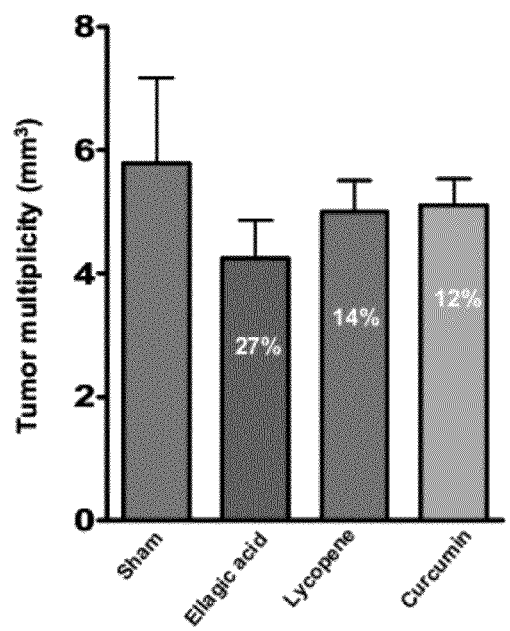

FIG. 23 includes graphs depicting the modulation of 17β-estradiol-induced mammary tumor volume (FIG. 23A) and mammary tumor multiplicity (FIG. 23B) by silastic tubing implants incorporating either ellagic acid, lycopene, or curcumin.

FIG. 24 includes graphs depicting the inhibition of 17β-estradiol-induced mammary tumor multiplicity (FIG. 24A) and mammary tumor volume (FIG. 24B) by ellagic acid, administered by a silastic tubing implant incorporating ellagic acid (slow release) or by dietary supplementation with ellagic acid.

Figure 25:
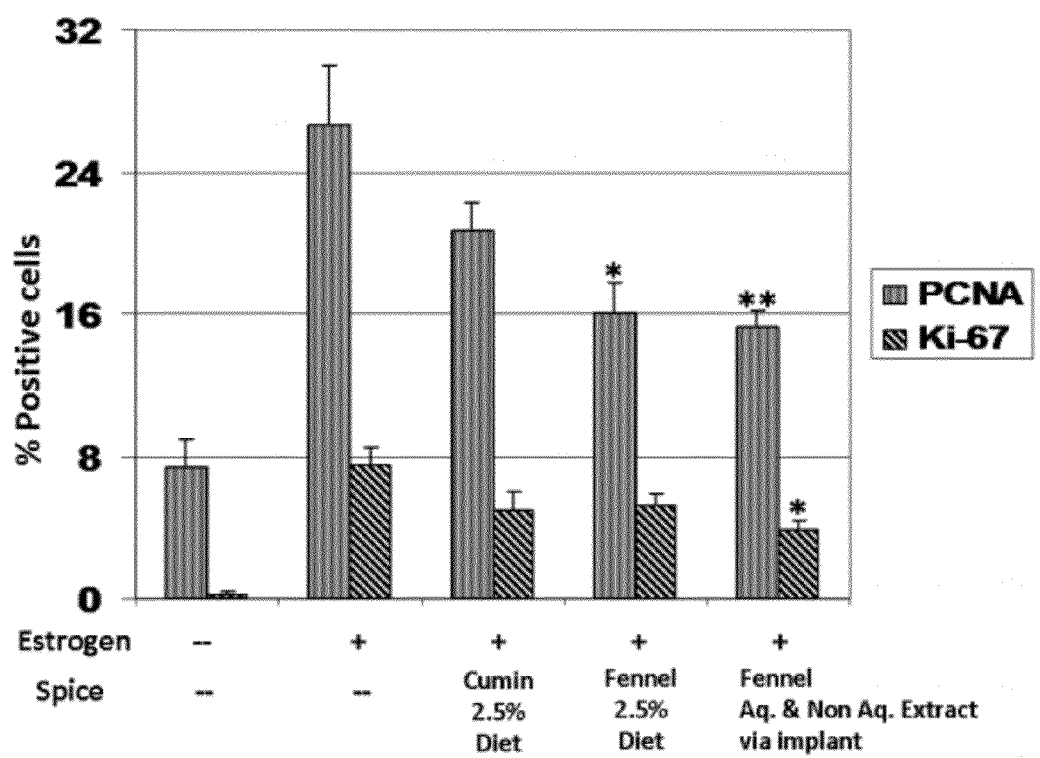

FIG. 25 is a graph depicting the effect of a biocompatible silastic tubing implant incorporating fennel extract on 17β-estradiol-induced mammary cell proliferation as measured by cytological evaluation of histological sections for cellular markers of proliferation, including proliferating cell nuclear antigen (PCNA) and the Ki-67 protein.

Figure 26A:
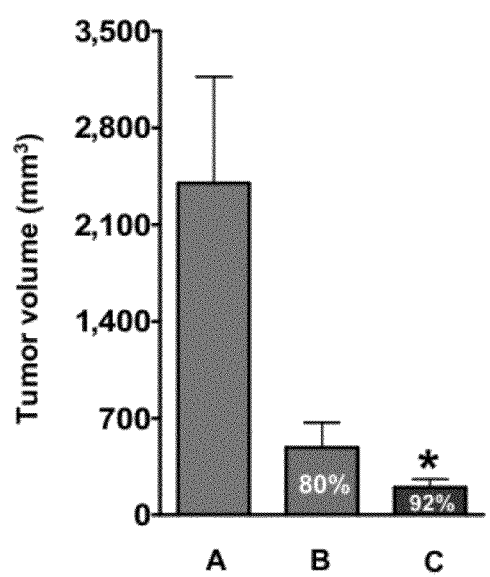
Figure 26B:
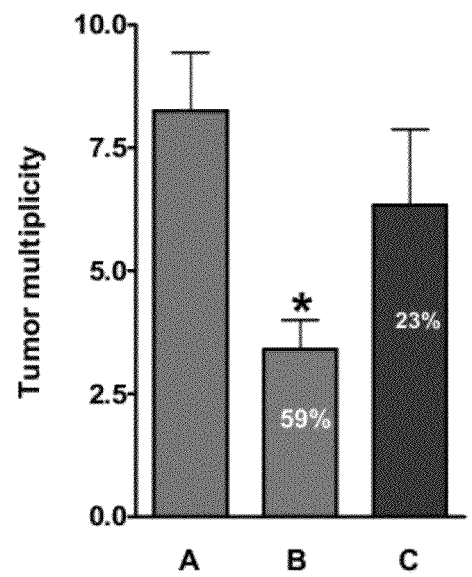

FIG. 26 includes graphs depicting the inhibition of 17β-estradiol-induced mammary tumor volume (FIG. 26A) and mammary tumor multiplicity (FIG. 26B) by the combined administration of phytochemical agents incorporated into biocompatible silastic tubing implants and implanted subcutaneously (A: sham implant; B: one implant each of oltipraz and curcumin; and, C: one implant each of curcumin, ellagic acid, coenzyme-Q 10, and lycopene), where the numbers on the bars represent percent reduction.

Figure 27:
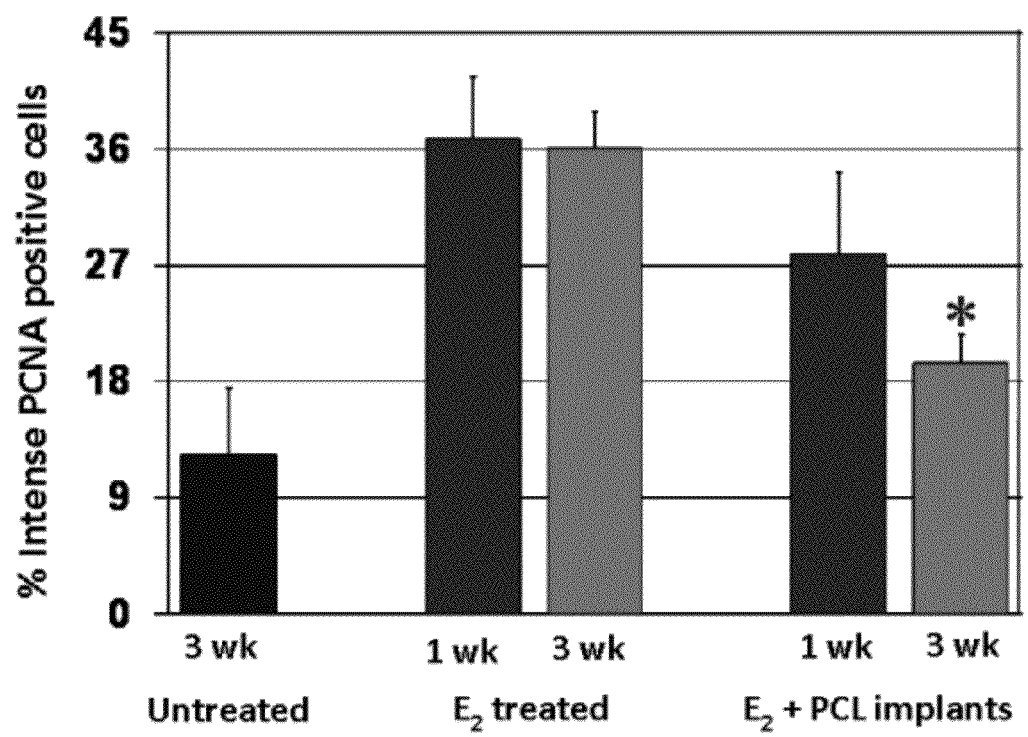

FIG. 27 is a graph depicting the effect of combined administration of curcumin, GTPs, DIM, and punicalagin implants, comprised of a biocompatible polymeric matrix, on mammary cell proliferation in rats treated with 17β-estradiol, where the percentage of PCNA positive cells is plotted against treatment groups at different time intervals.

Figure 28:
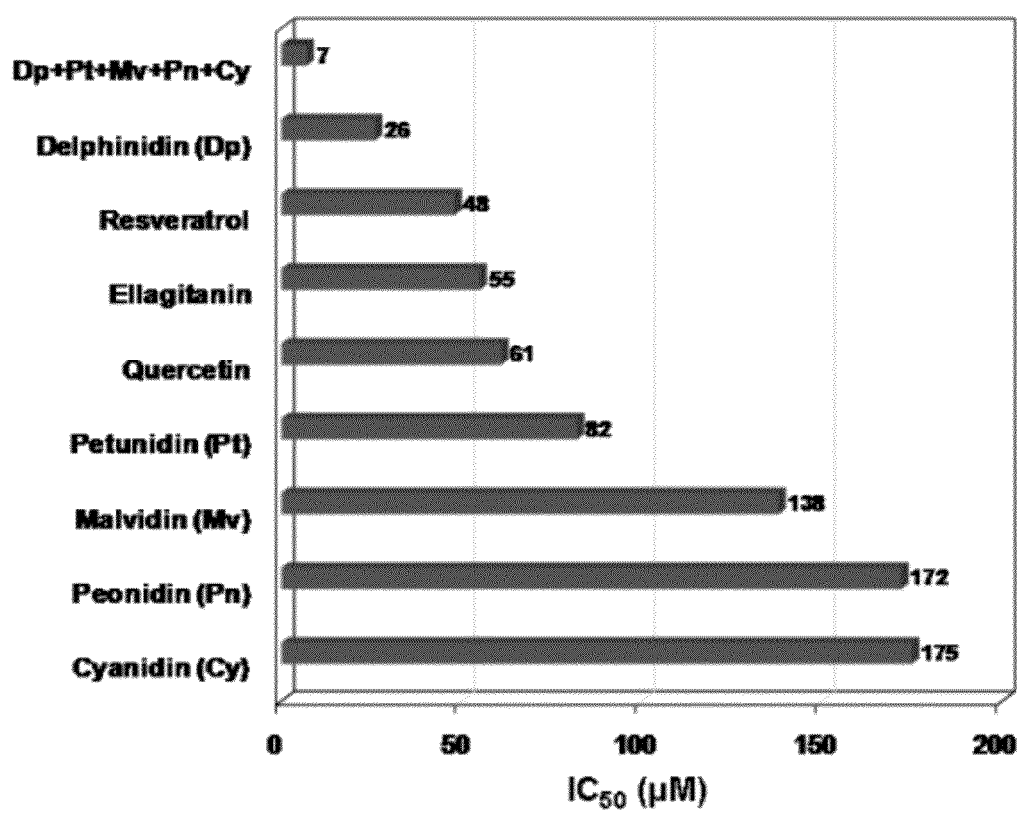

FIG. 28 is a graph depicting the synergistic activity of various phytochemical agents in inhibiting growth of H1299 human lung cancer cells, where the various phytochemical agents (y-axis) are plotted against the half maximal inhibitory concentration ($IC_{50}$) for each agent (x-axis).

Figure 29:
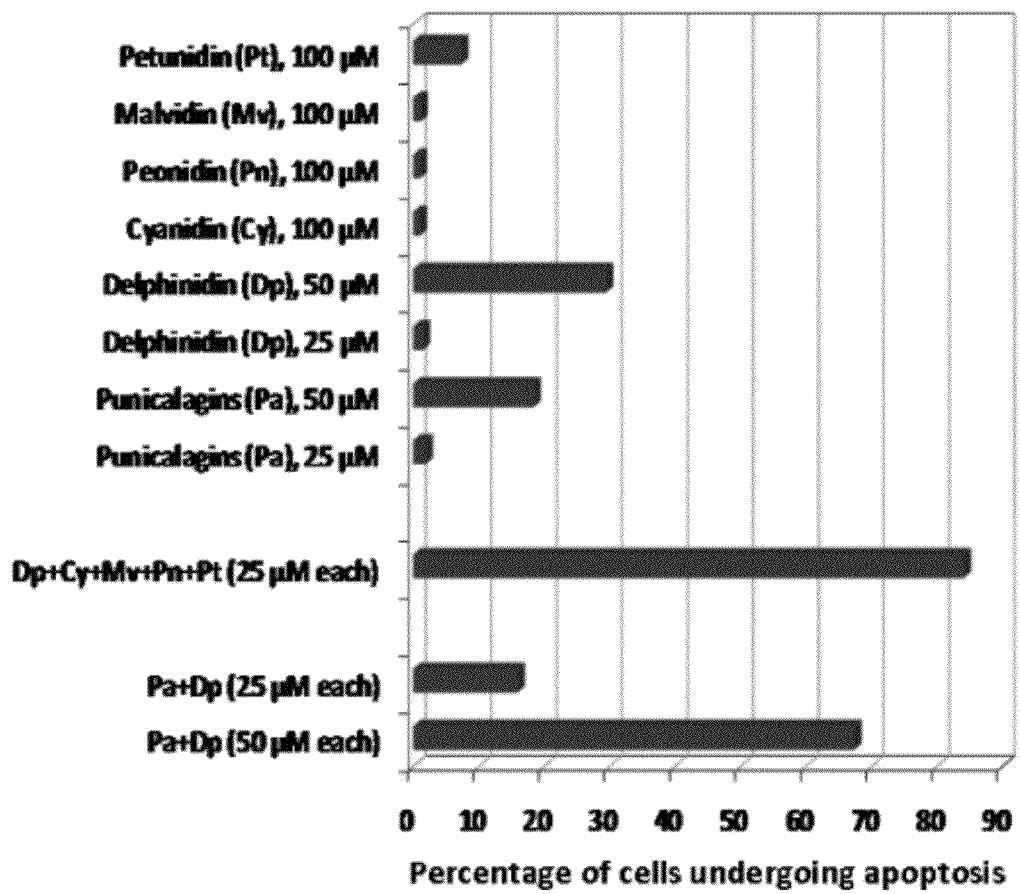

FIG. 29 is a graph depicting the synergistic activity of various phytochemical agents in inducing apoptosis in H1299 human lung cancer cells where the various phytochemical agents (y-axis) are plotted against the percentage of cells undergoing apoptosis (x-axis).

Figure 30:
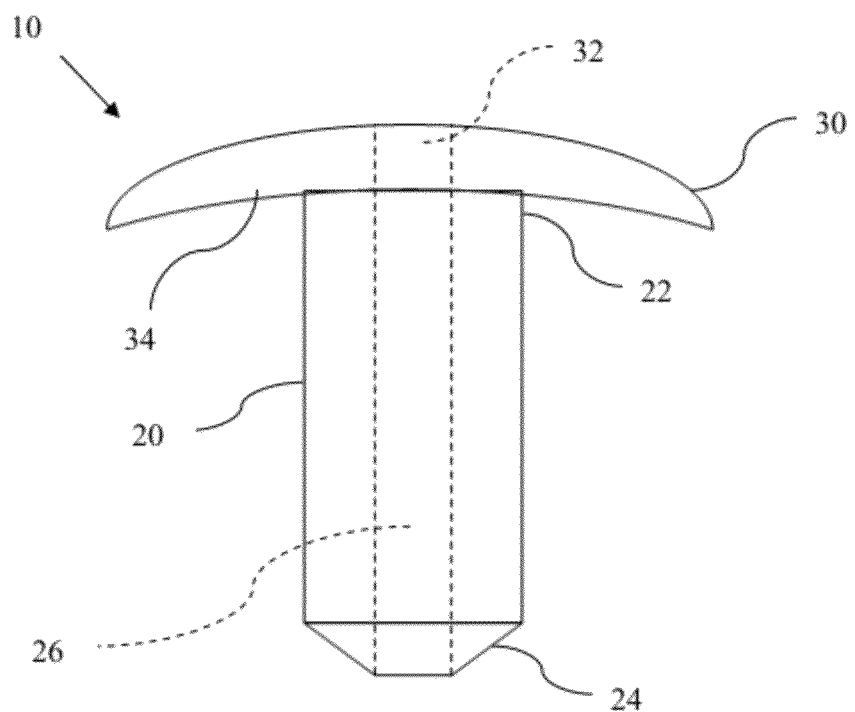

FIG. 30 is a side view of a device for insertion into a cervical canal made in accordance with the presently-disclosed subject matter.

Figure 31:
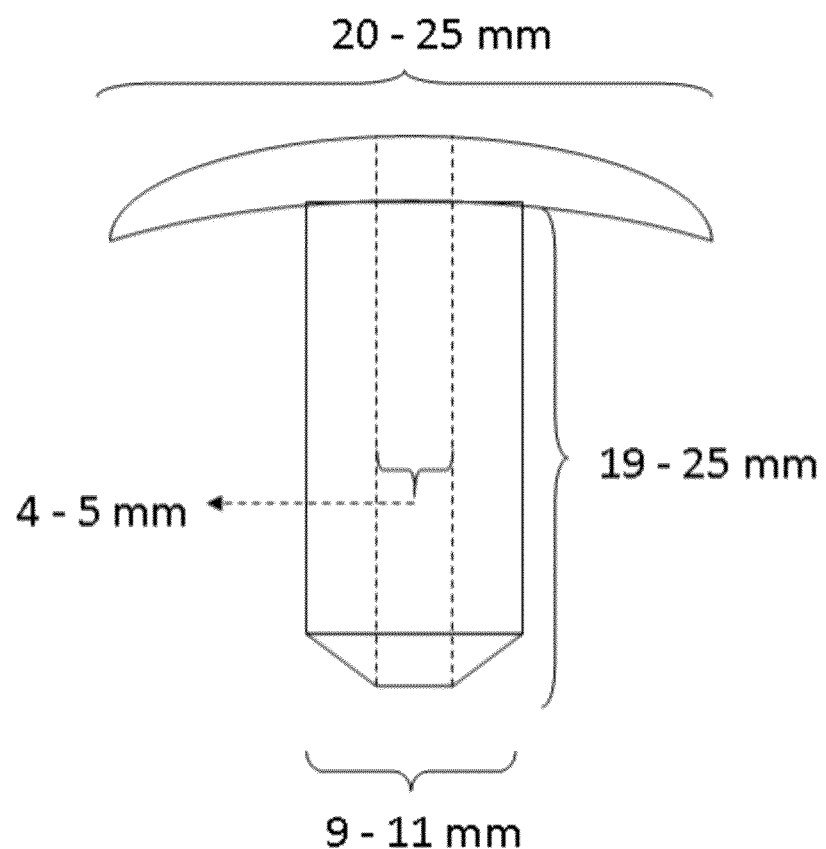

FIG. 31 is a side view of a device for insertion into a cervical canal made in accordance with the presently-disclosed subject matter and depicting exemplary dimensions of features of the device.

Figures 32A, 32B:
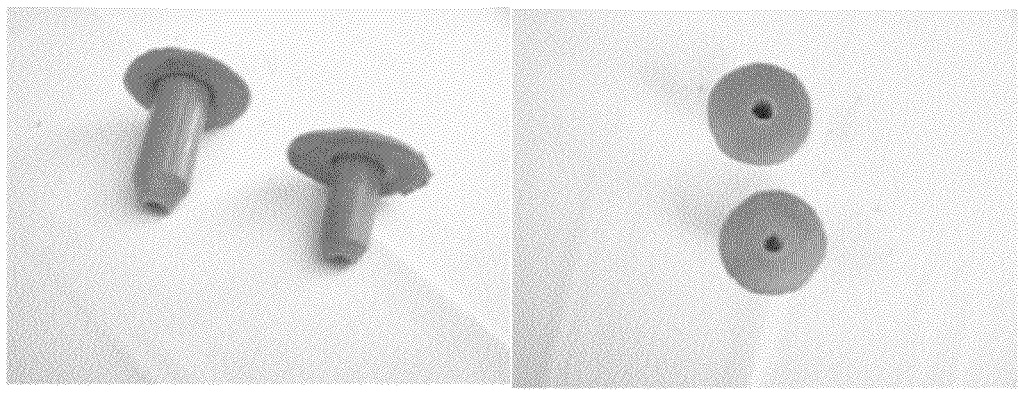
Figures 32C, 32D:

FIG. 32 includes perspective views (FIGS. 32A, 32B, 32C, and 32D) of an exemplary device for cervical insertion.

Figure 33A:
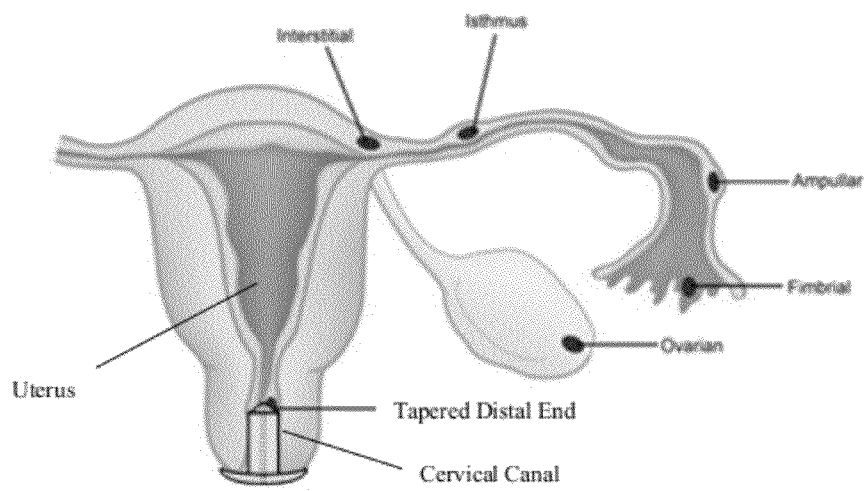
Figure 33B:
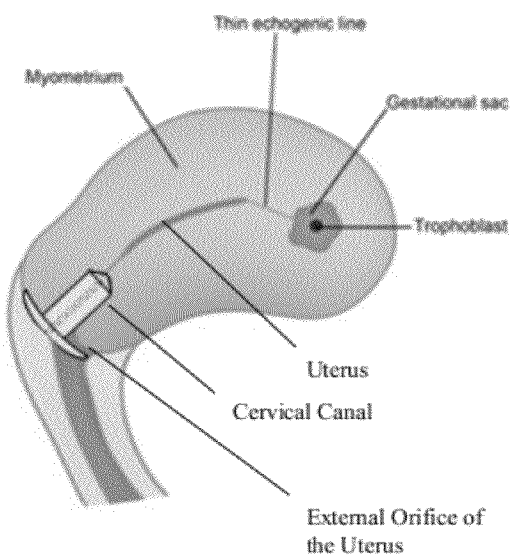

FIG. 33 includes schematic diagrams depicting the placement of an exemplary device for cervical insertion. FIG. 33A is a schematic diagram depicting a front view of an exemplary device and showing the device engaging the walls of a cervical canal and the external orifice of a uterus. FIG. 33B is a schematic diagram depicting a side view of the device and showing the device engaging the walls of a cervical canal and the external orifice of a uterus.

Figure 34A:
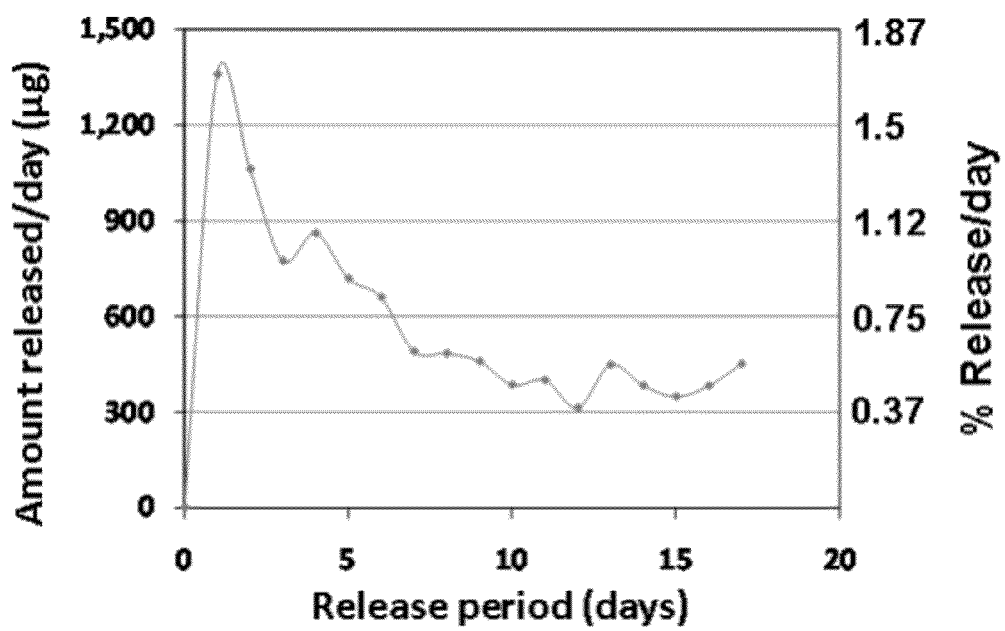
Figure 34B:
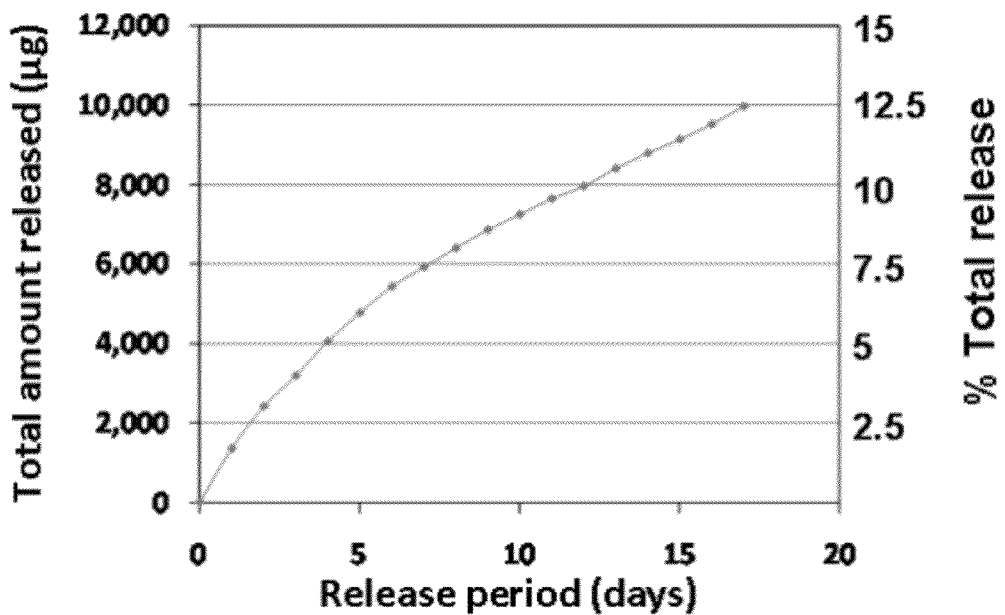

FIG. 34 includes graphs depicting the release of curcumin from an exemplary device for cervical insertion in vitro. FIG. 34A is a graph depicting the daily release of curcumin from an exemplary device for cervical insertion where the amount (μg) of curcumin released per day (y-axis) and the percentage of curcumin released from the device per day (y-axis) are plotted against a release period measured in days (x-axis). FIG. 34B is a graph depicting the cumulative release of curcumin from an exemplary device for cervical insertion where the total amount (μg) of curcumin released from the device (y-axis) and the total percentage of curcumin released from the device (y-axis) are plotted against a release period measured in days (x-axis).

Figure 35:
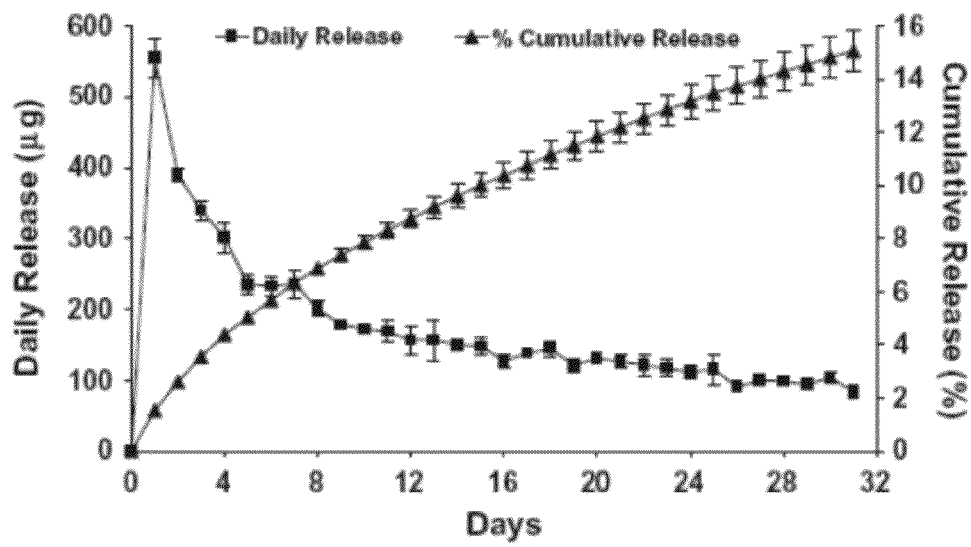

FIG. 35 is a graph depicting the daily and cumulative release of curcumin from a 2-cm biocompatible polymeric matrix composition (20 mg curcumin/cm) under simulated in vitro conditions (n=3), where the polymeric matrix was formed from polycaprolactone-121K and polyethylene glycol-8K in a 65:35 ratio.

Figure 36:
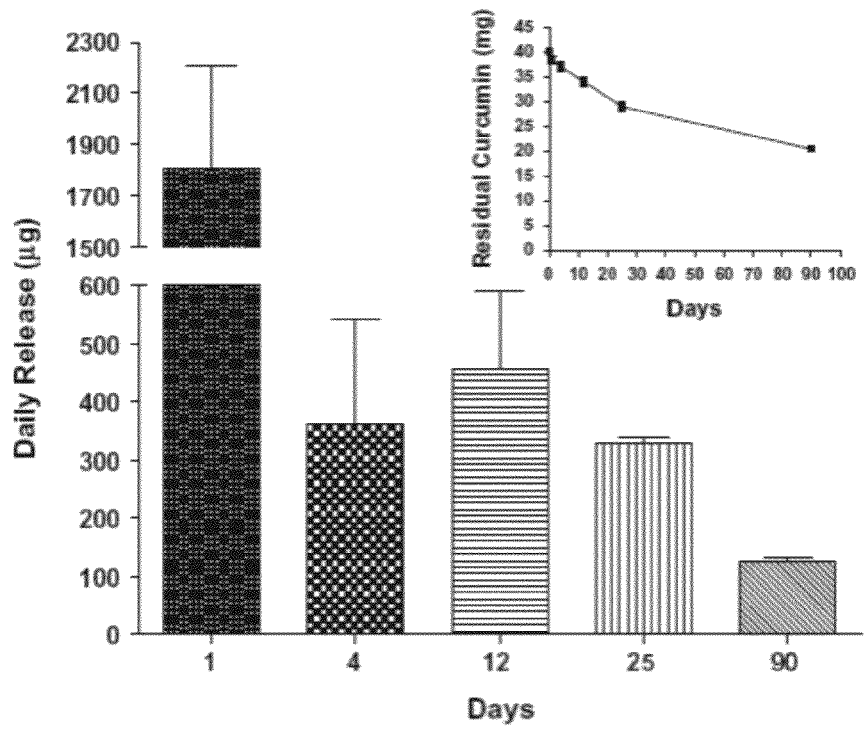

FIG. 36 includes graphs depicting the average daily release of curcumin from a 2-cm biocompatible polymeric matrix incorporating 40 mg of curcumin under in vivo conditions, where the biocompatible polymeric matrix was formed from polycaprolactone-121K and polyethylene glycol-8K in a 65:35 ratio, where the compositions were subcutaneously grafted into the back of the ACI rats and recovered after indicated time intervals, and where residual curcumin (inset graph) was measured to determine cumulative drug release.

Figure 37:
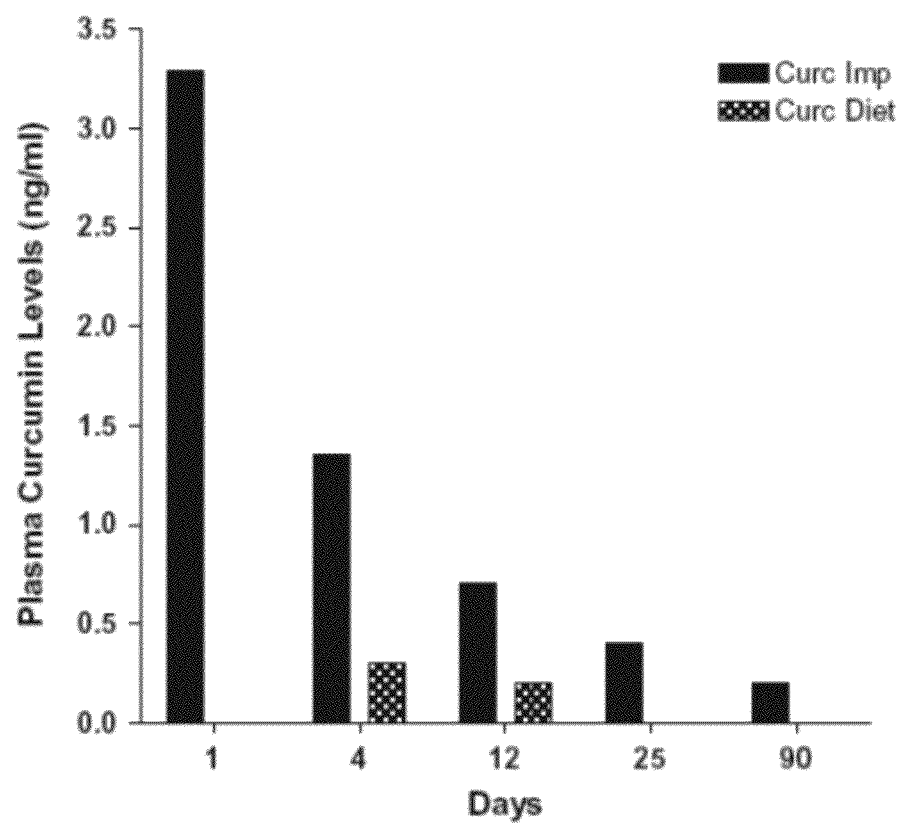

FIG. 37 is a graph depicting curcumin levels in the plasma of ACI rats treated with biocompatible polymeric matrix compositions formed from polycaprolactone-121K and polyethylene glycol-8K in a 65:35 ratio and incorporating curcumin (two 2-cm implants; 20 mg curcumin/cm) or treated with a curcumin diet (1000 ppm), where 1.5 ml plasma was extracted from each time point after pooling and analyzed by HPLC using a fluorescence detector.

Figure 38:
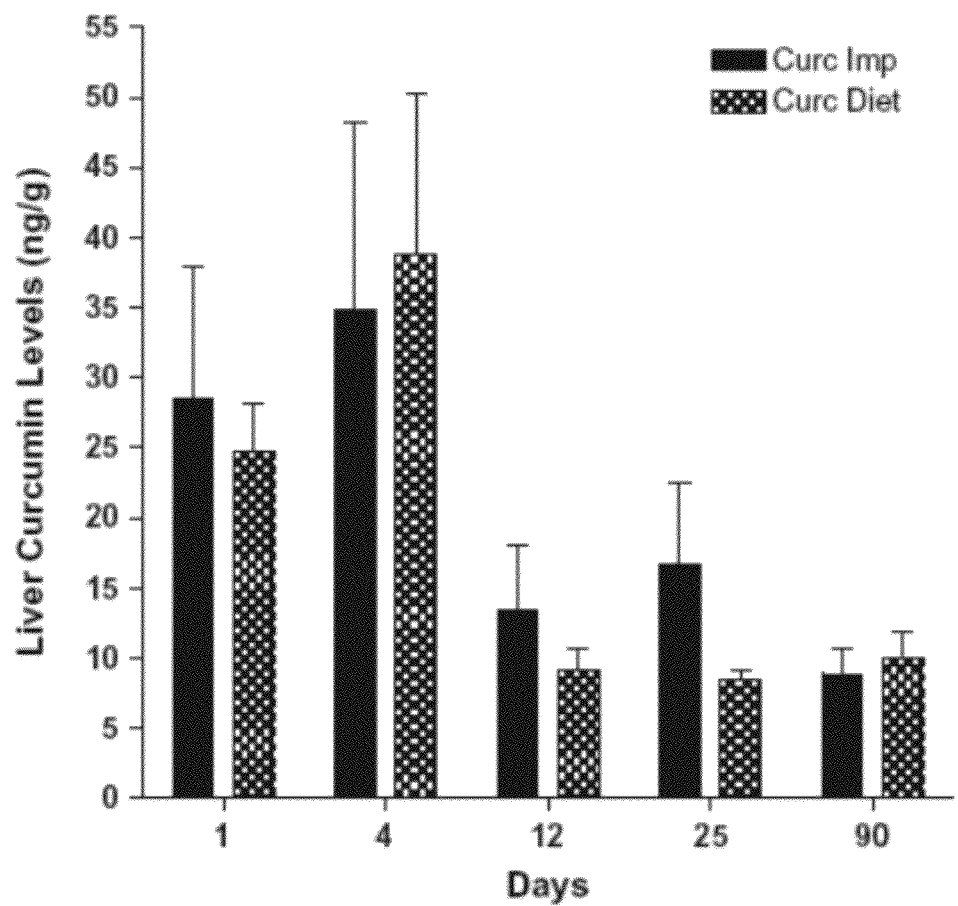

FIG. 38 is a graph depicting liver curcumin levels in ACI rats treated with biocompatible polymeric matrix compositions formed from polycaprolactone-121K and polyethylene glycol-8K in a 65:35 ratio and incorporating curcumin (two 2-cm implants, 20 mg/cm implant) or treated with a curcumin diet (1000 ppm), where, based on about a 10 g daily diet consumption, the total curcumin administered over 90 days corresponded to 900 mg (or approximately 50 mg/kg b.wt.) as opposed to 38 mg delivered by both the implants combined (2.11 mg/kg b.wt.), and where tissues (approximately 500 mg) from individual animals were extracted and analyzed by HPLC coupled with a fluorescence detector.

Figure 39:
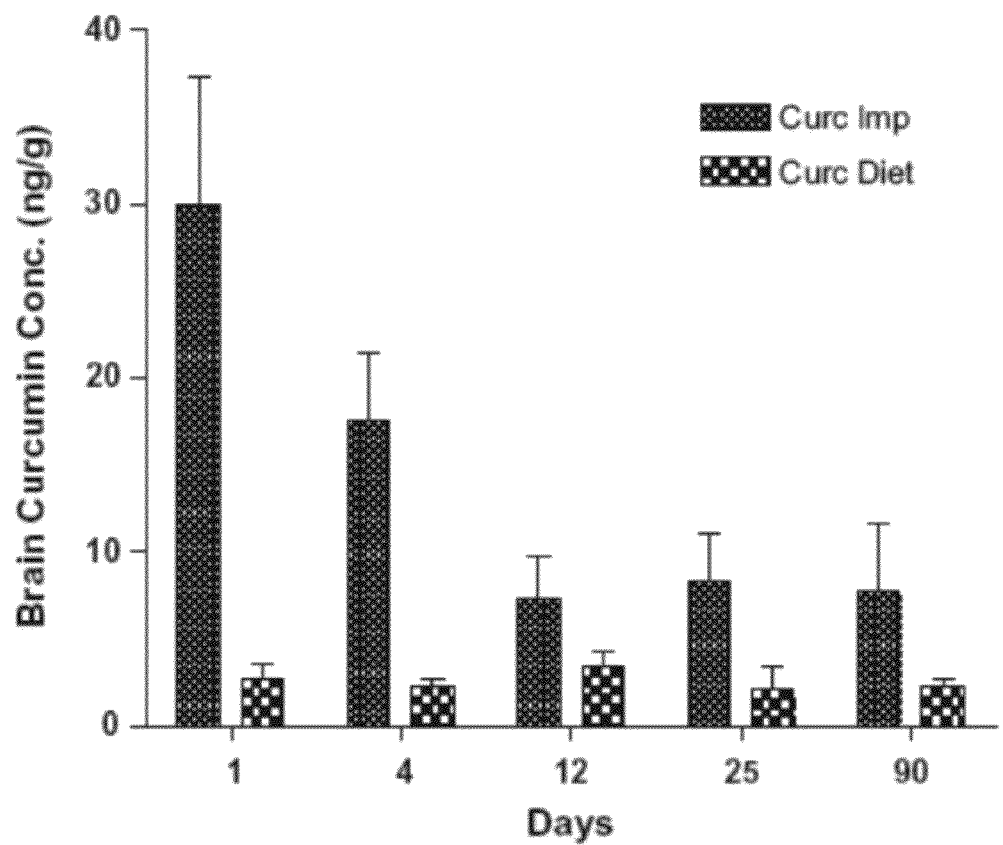

FIG. 39 is a graph depicting brain curcumin levels in ACI rats treated with biocompatible polymeric matrix compositions formed from polycaprolactone-121K and polyethylene glycol-8K in a 65:35 ratio and incorporating curcumin (two 2-cm implants, 20 mg/cm) or treated with dietary curcumin (1000 ppm), where tissues (approximately 500 mg) from individual animals were extracted and analyzed by HPLC coupled with a fluorescence detector.

Figure 40:
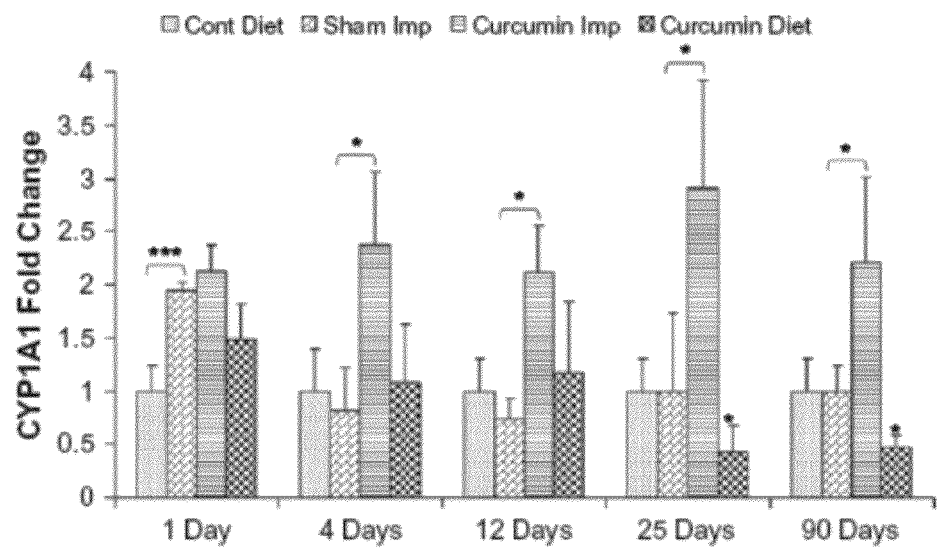

FIG. 40 is a graph depicting the effect of curcumin administered by biocompatible polymeric matrix compositions formed from polycaprolactone-121K and polyethylene glycol-8K in a 65:35 ratio and incorporating curcumin (two 2-cm implants, 20 mg/cm) or by diet (1000 ppm) on CYP1A1 protein expression in hepatic microsomes of ACI rats, where sham implants (blank implants prepared without curcumin) and curcumin diet groups were compared with untreated controls, and where curcumin implants were compared with sham implants for all statistical purposes at a significance level of p value <0.05.

Figure 41:
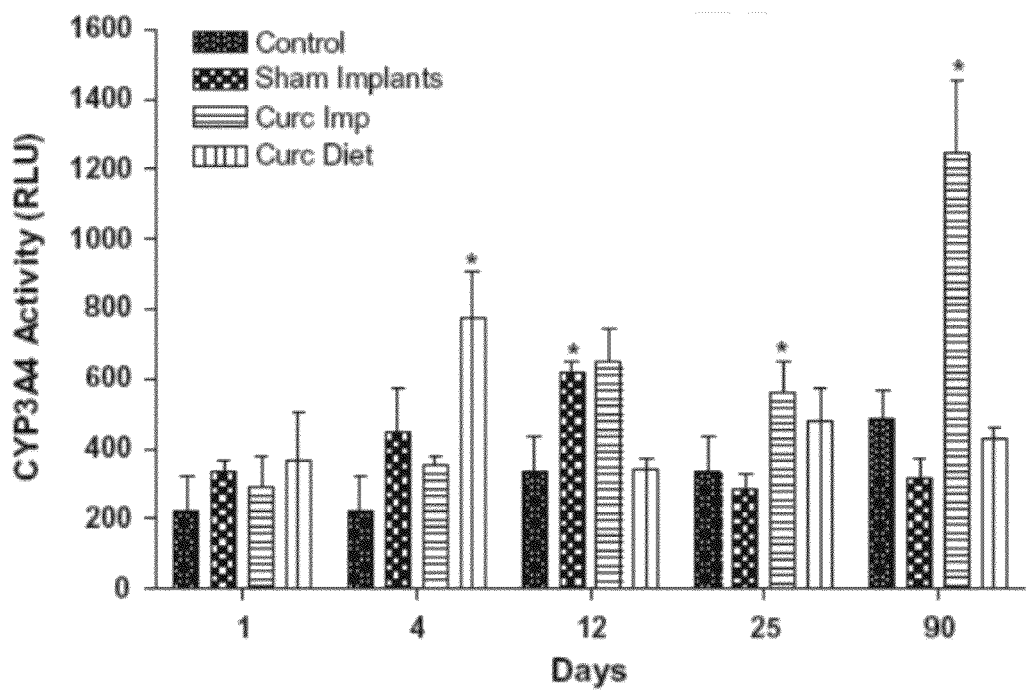

FIG. 41 is a graph showing the effect of curcumin administered by biocompatible polymeric matrix compositions formed from polycaprolactone-121K and polyethylene glycol-8K in a 65:35 ratio and incorporating curcumin (two 2-cm implants, 20 mg/cm) or by diet (1000 ppm) on CYP3A4 activity in hepatic microsomes of ACI rats, where sham implants (blank implants prepared without curcumin) and curcumin diet groups were compared with untreated controls, and where curcumin implants were compared with sham implants for all statistical purposes at a significance level of p value <0.05.

Figure 42:
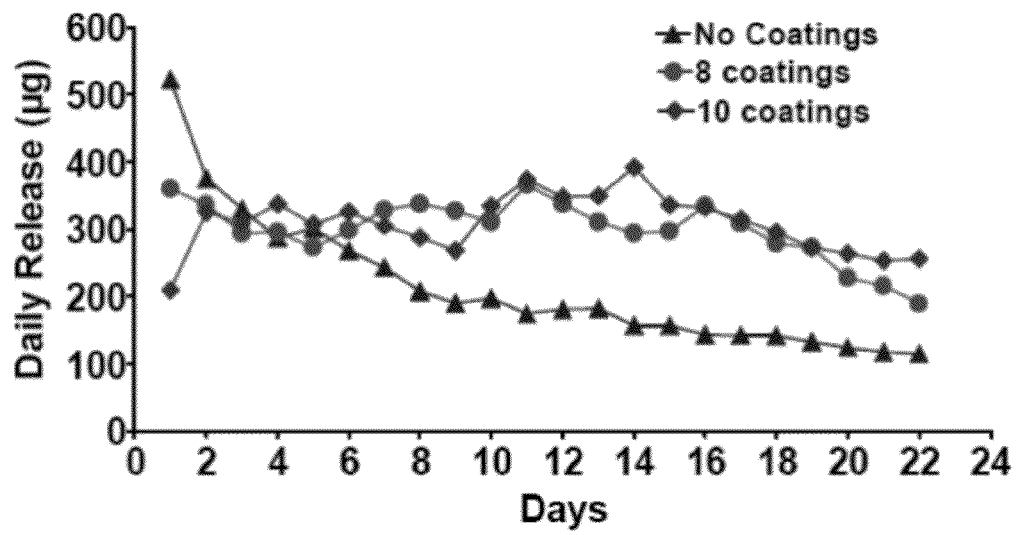

FIG. 42 is a graph showing the effect of coating each biocompatible polymeric matrix composition incorporating curcumin with various numbers of layers of blank polycaprolactone to minimize the initial burst release, where the compositions were coated with a 10% solution of polycaprolactone—80K (mol. wt. 80,000) in dichloromethane with intermittent drying.

Figure 43A:
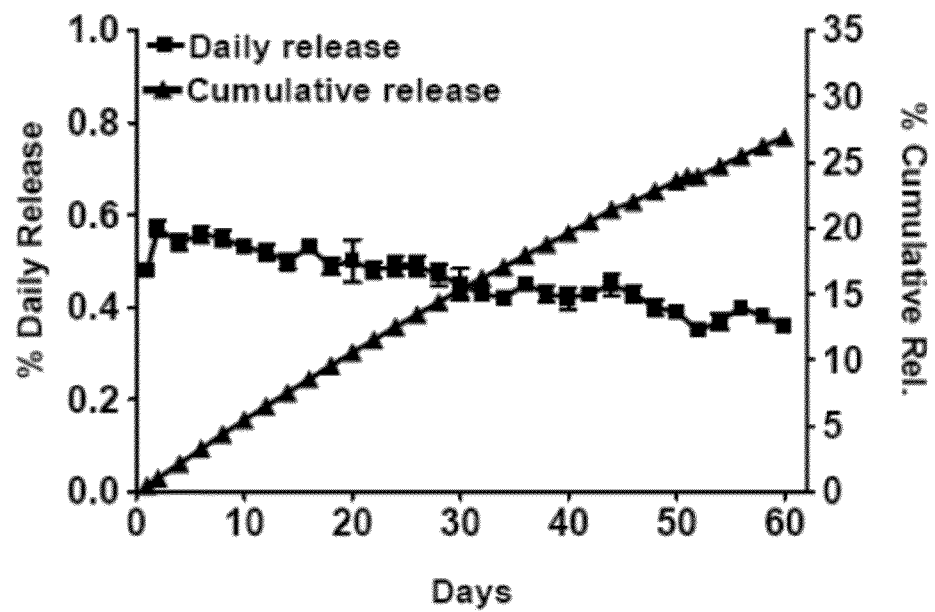
Figure 43B:
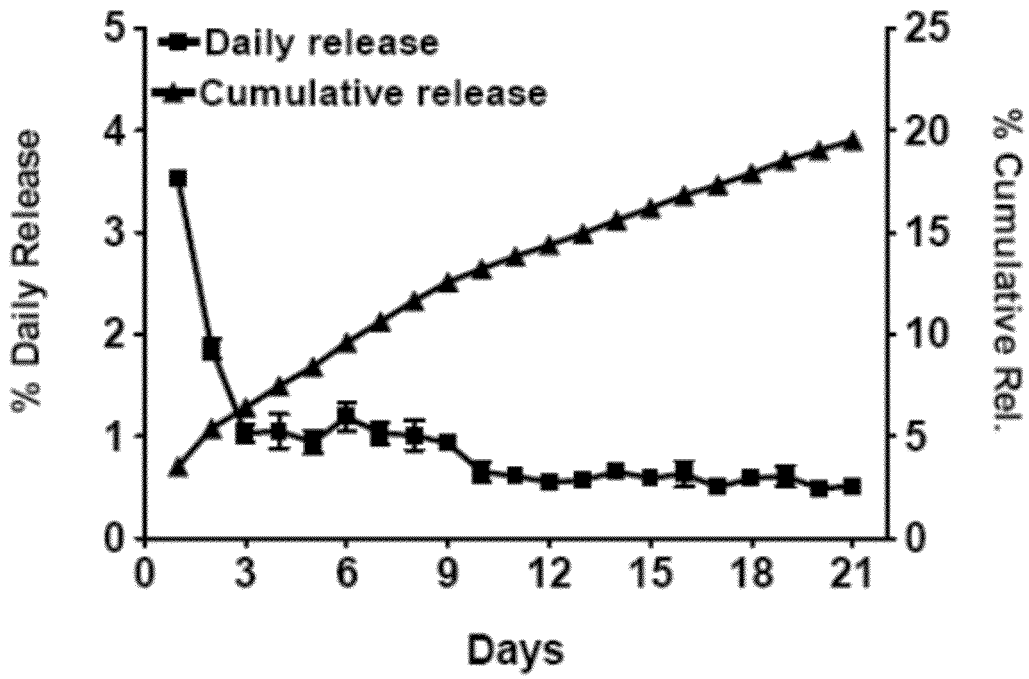
Figure 43C:
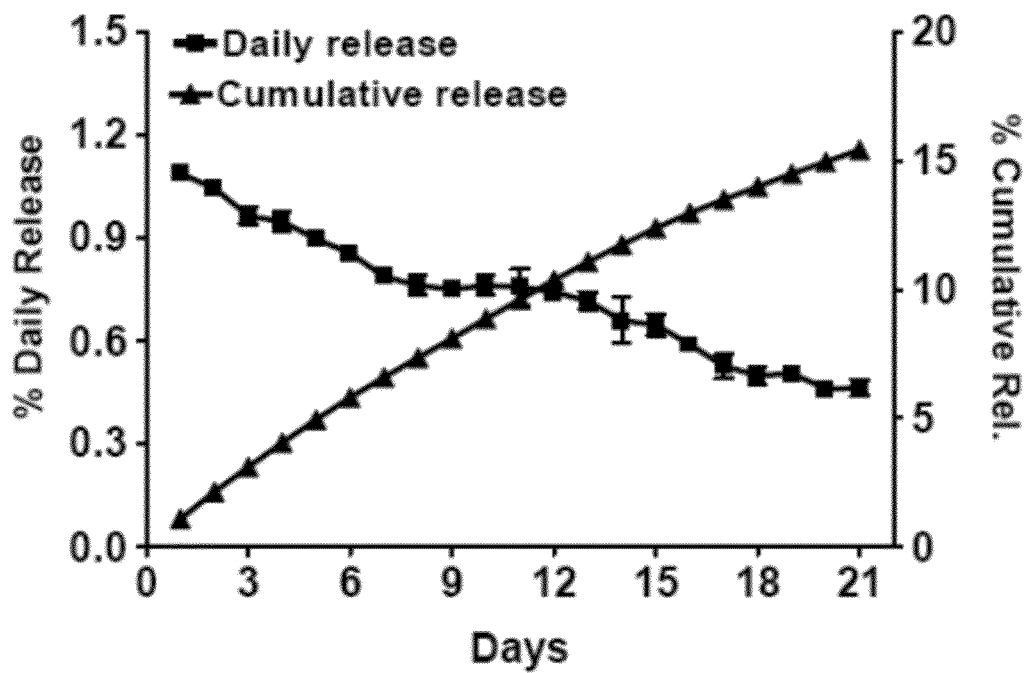

FIG. 43 includes graphs depicting the percent average in vitro daily and cumulative release of oltipraz (FIG. 43A), withaferin A (FIG. 43B), and curcumin (FIG. 43C) from biocompatible polymeric matrices prepared by coating 20 to 30 layers of polycaprolactone incorporating the phytochemical agents (2 cm length, 2.6 mm dia), where the load of phytochemical agent was 20%, except for withaferin A which was 3%, and where the release was measured by agitating the compositions in a shaker incubator in PBS supplemented with 10% bovine serum and the media was changed daily.

FIG. 44 includes graphs depicting the percent average in vitro daily and cumulative release of curcuminoid I (FIG. 44A), curcuminoid II (FIG. 44B), curcuminoid III (FIG. 44C), and mixture of three curcuminoids in natural ratio as presented in curcumin (75:20:5; FIG. 44D) from biocompatible polymeric matrices incorporating the phytochemical agents and prepared by the coating procedure (2 cm length, 2.6 mm dia; 10% drug load), where the compositions were agitated in a shaker incubator in PBS supplemented with 10% bovine serum and the media was changed daily, and where the release was measured spectrophotometrically against the standard curve of individual curcuminoids.

Figure 45A:
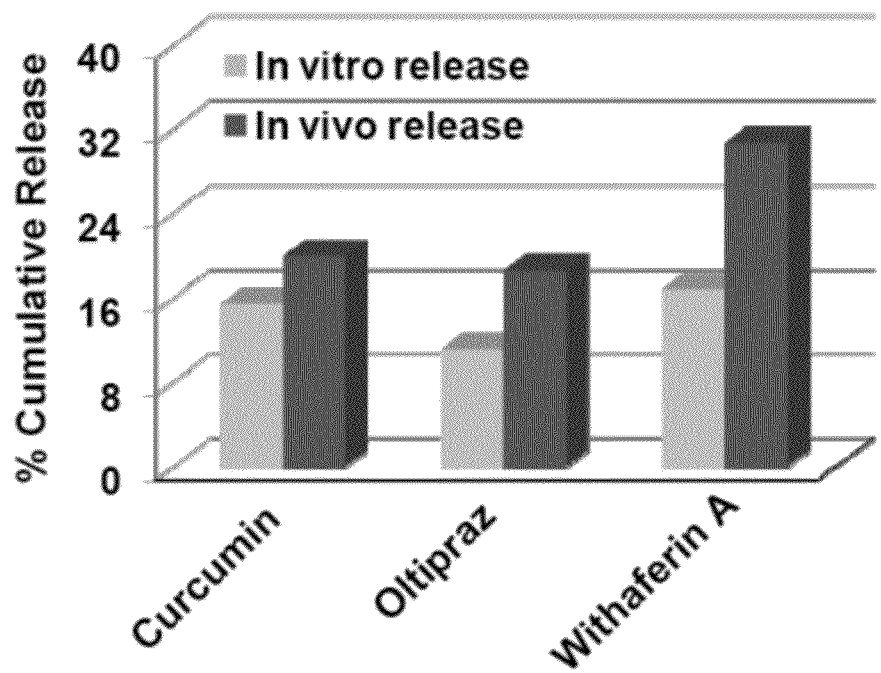
Figure 45B:
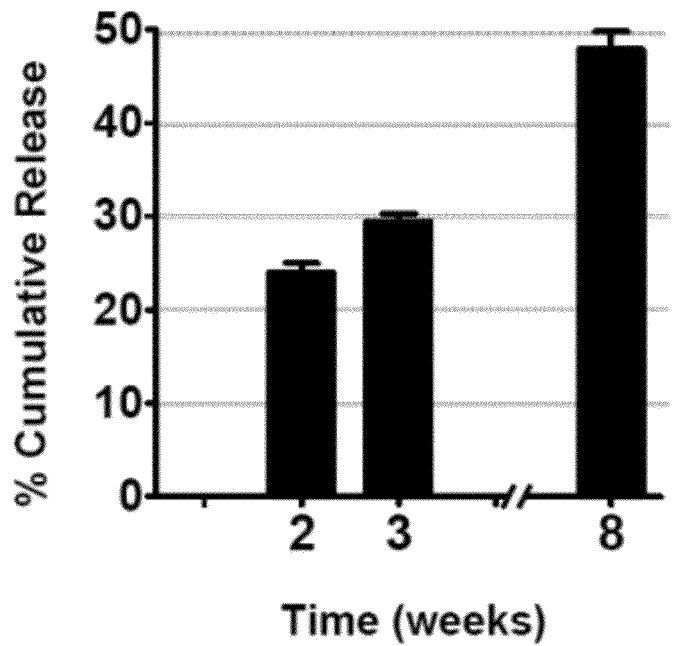

FIG. 45 includes graphs depicting the rate of in vitro and in vivo release of curcumin, oltipraz and withaferin A (FIG. 45A) from coated biocompatible polymeric matrices grafted subcutaneously in female A/J mice where the animals were euthanized after 3 weeks and the implants recovered were solvent extracted to measure the residual amount as described in text, and depicting the in vivo cumulative release of withaferin A (FIG. 45B) from coated biocompatible polymeric matrices (1.5 cm, 5% drug load) grafted subcutaneously in female A/J mice where the animals were euthanized after 3, 5 and 8 weeks and the matrices that were recovered were solvent extracted to measure the residual amount by ultra performance liquid chromatography (UPLC)-UV.

Figure 46A:
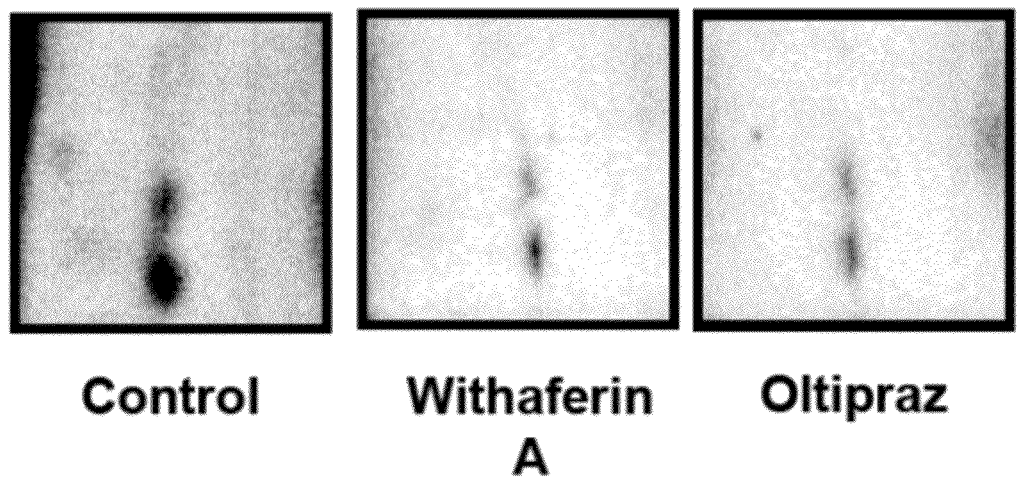
Figure 46B:
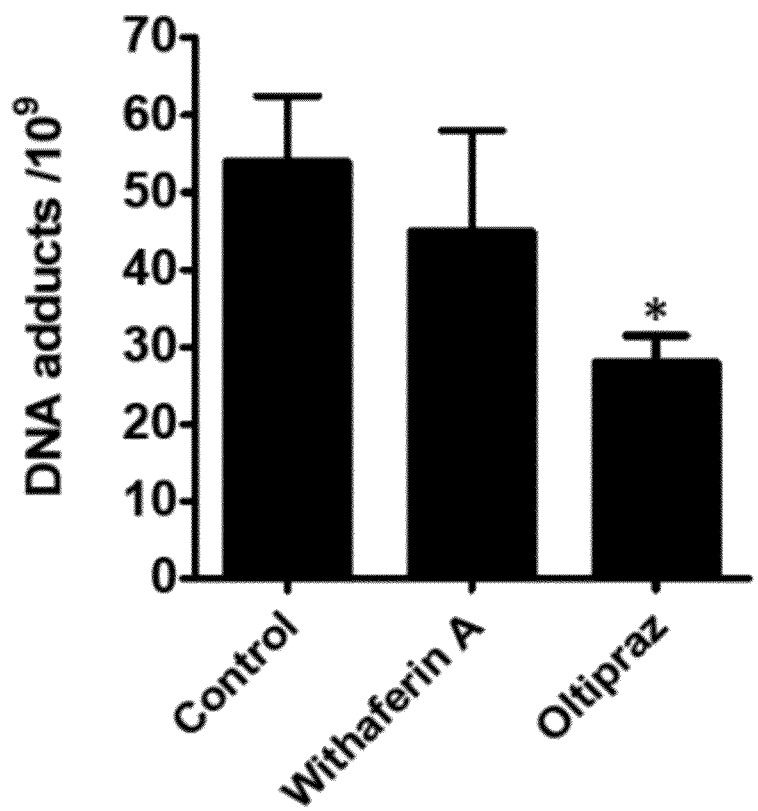

FIG. 46 includes images (FIG. 46A) and a graph (FIG. 46B) depicting the inhibition of dibenzo[a,l]pyrene (DBP)-DNA adducts in lung tissue of female A/J mice by phytochemical agents delivered via biocompatible polymeric matrices of the presently-disclosed subject matter, where animals were treated with DBP by subcutaneous polymeric implants or implants of oltipraz and withaferin A (two 1.5 cm, 2.6 mm dia; 20% and 5% loads, respectively), and where, three weeks later, animals were euthanized and lung DNA adducts were analyzed by $^{32}P$-postlabeling.

Figure 47A:
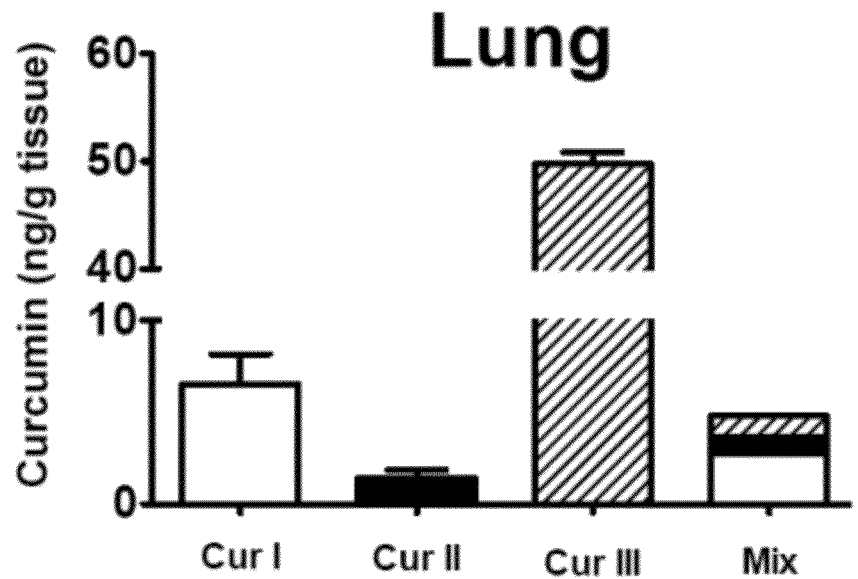
Figure 47B:
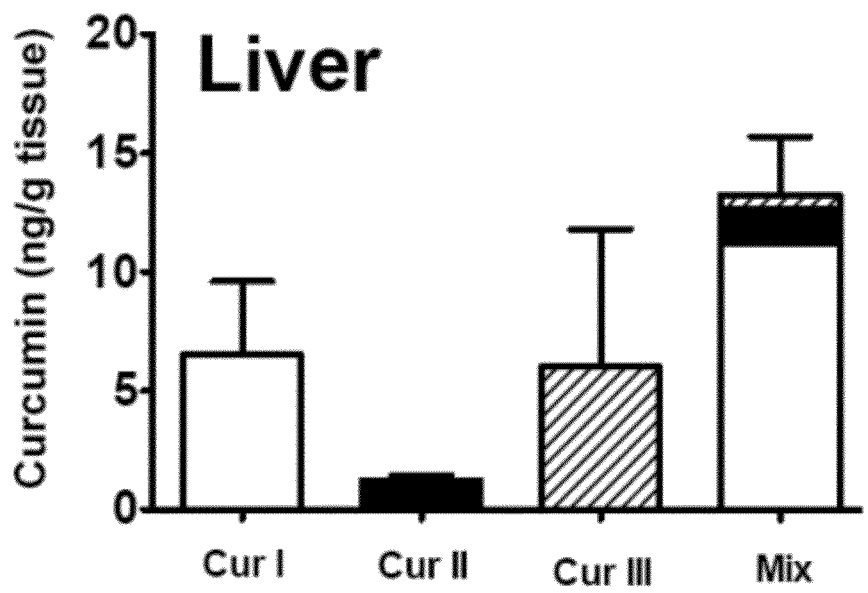
Figure 47C:
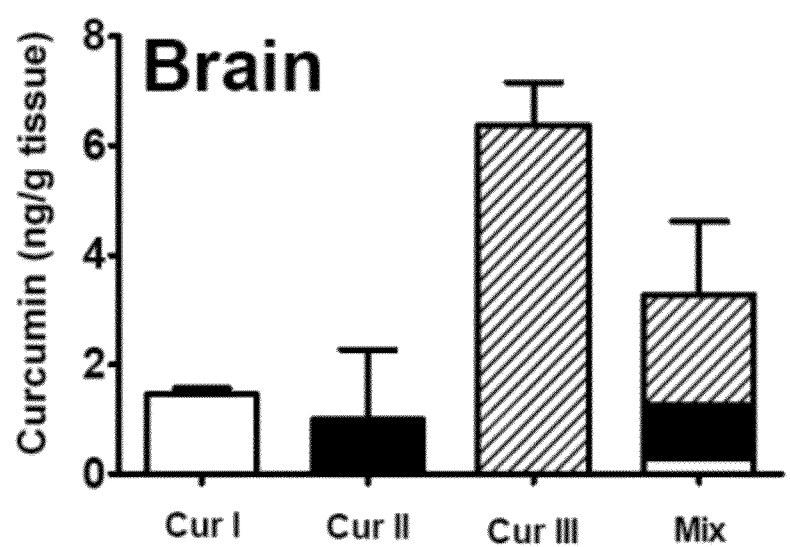

FIG. 47 includes graphs depicting curcuminoid levels in lung (FIG. 47A), liver (FIG. 47B) and brain (FIG. 47C) of female A/J mice treated with curcumin via biocompatible polymeric matrices (two, 1.5-cm implants; 10% drug load) for 21 days, where samples were analyzed by ultra performance liquid chromatography (UPLC).

Figure 48A:
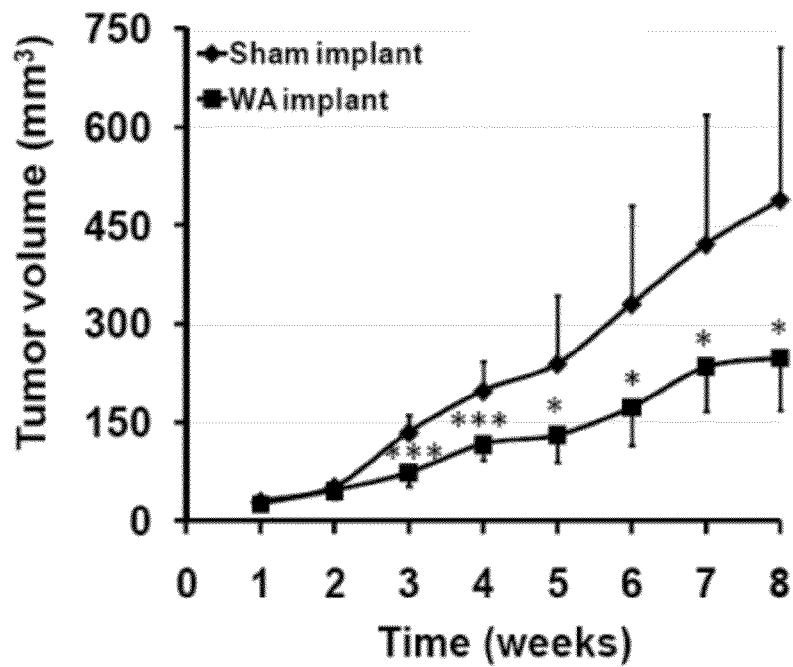
Figure 48B:
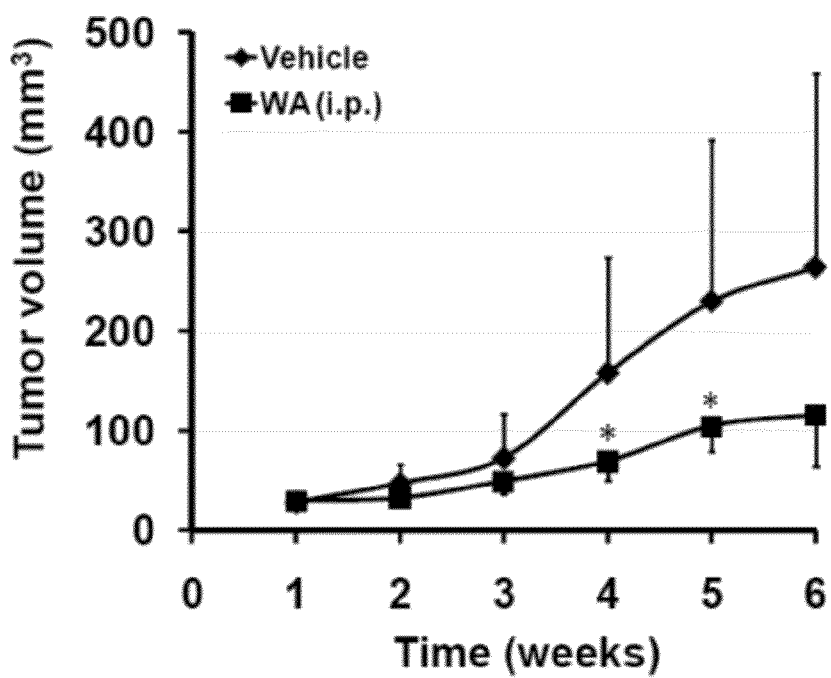
Figure 48C:
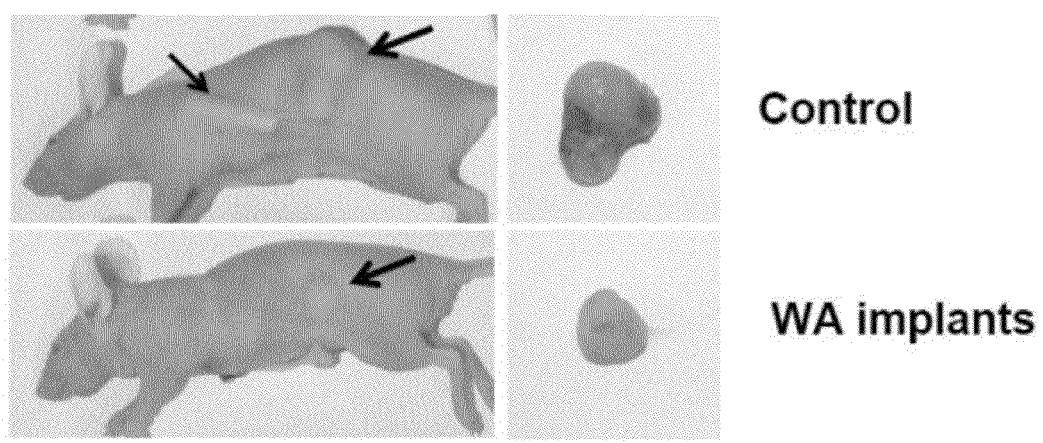

FIG. 48 includes graphs and an image depicting the effects of polymeric implants incorporating withaferin A and prepared by a coating procedure on the inhibition of human lung cancer A549 cell xenografts in nude mice, where, following inoculation with human lung cancer A549 cells ($2.5 \times 10^6$ cells), when tumor xenografts grew to over 50 mm$^3$, animals were grafted with polymeric implants (two 1.5-cm implants, 2.4 mm dia; 5% WA) (FIG. 48A) and two other groups, following inoculation with A549 cells, were treated intraperitoneally (i.p.) on alternate days with vehicle or withaferin A (8 mg/kg) two days after inoculation (FIG. 48B), with representative animals at the time of euthanasia and excised tumors shown in FIG. 48C.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The benefits of phytochemicals as therapeutic agents has been demonstrated in a variety of different physiological contexts and pathological conditions. Recently, epidemiological and experimental data has indicated that many phytochemical agents in fruits and vegetables are capable of lowering cancer risk (Steinmetz & Potter, 1991). β-carotene, for instance has been shown to have anti-oxidant properties and was demonstrated to inhibit carcinogenesis by preventing DNA damage (Sun, 1990), besides having immunomodulatory effects in animal models (Bendich, 1989). Similarly, previous studies have suggested a role for vitamin E in promoting immune function (Weitberg, et al., 1997) and have shown that pre-menopausal women with a family history of breast cancer who consumed a high quantity of vitamin E demonstrated a 43% reduction in breast cancer incidence (Zong, et al., 1999).

While phytochemical agents are known to have many health-promoting properties, including reducing cancer mortality, their application as an effective agent for the prophylaxis and treatment of cancer has been limited by the delivery of these agents orally in a capsule, tablet, or powdered format. In this regard, the biggest drawback of phytochemical agents in the prophylaxis and treatment of cancer is that oral delivery of these agents results in limited bioavailability. Similar to traditional chemotherapeutic agents, when phytochemical agents are administered orally, a large part of the agent is destroyed in the gut and a large portion of the remaining phytochemical agent is detoxified during first pass through the liver. As such, a high oral dose of the phytochemical agent is required to achieve a reasonable therapeutic effect. Systemic delivery overcomes this hurdle, but again, like traditional chemotherapeutic agents, systemic delivery can lead to undesirable dose spikes and potential toxicity. To that end, the presently-disclosed subject matter provides new compositions, and methods of using the same, for administering phytochemical agents in a controlled low dose over a period of time.

In some embodiments of the presently-disclosed subject matter, a composition is provided that comprises a biocompatible polymeric matrix incorporating an effective amount of a phytochemical agent. In some embodiments, the composition is capable of releasing a controlled low dose of the phytochemical agent over a time period. In some embodiments, the time period is at least about 18 months.

The term "biocompatible" is used herein to refer to a composition that is substantially non-toxic in the in vivo environment of its intended use, and that is not substantially rejected by the subject's physiological system (i.e., is non-antigenic). As will be recognized by those of ordinary skill in the art, the biocompatibility of a particular composition can be gauged by the composition's toxicity, infectivity, pyrogenicity, irritation potential, reactivity, hemolytic activity, carcinogenicity, and/or immunogenicity. When introduced into a majority of subjects, a biocompatible composition will not cause an undesirably adverse, long-lived, or escalating biological reaction or response, and is distinguished from a mild, transient inflammation, which typically accompanies surgery or implantation of foreign objects into a living organism.

A biocompatible polymeric matrix of the presently-disclosed subject matter can be fabricated from a variety of polymeric materials. Generally, polymeric materials are broadly classified as synthetic, natural, or blends thereof, and within these broad classes, the polymeric materials can be further classified as biodegradable or biostable. Biodegradable polymers degrade in vivo as a function of chemical composition, method of manufacture, and composition structure. Biostable polymers, on the other hand, remain intact in vivo for extended periods of time ranging from several years to more and include polymers such as ethylene-vinyl acetate copolymers, polyurethanes, polyacrylonitriles, and certain polyphosphazenes.

In some embodiments of the presently-disclosed subject matter, a biocompatible polymeric matrix is provided that is biodegradable. To provide a biocompatible polymeric matrix that is biodegradable, both synthetic and natural polymers can be used, with synthetic polymers being preferred due to a more uniform and reproducible degradation, as well as other physical properties. Examples of synthetic biodegradable polymers capable of being used in accordance with the presently-disclosed subject matter include, but are not limited to, polycaprolactone, polyanhydrides, polyhydroxyacids such as polylactic acid, polyglycolic acids and copolymers thereof, polyesters, polyamides, polyorthoesters, and certain polyphazenes. Examples of naturally-occurring biodegradable polymers capable of being used in accordance with the presently-disclosed subject matter include, but are not limited to, proteins and polysaccharides such as collagen, hylauronic acid, albumin, and gelatin.

In some embodiments, a biocompatible polymeric matrix is provided that is comprised of a polymers selected from polycaprolactone, cyclodextrin, F68, polyethylene glycol, and combinations thereof. In some embodiments, the biocompatible polymeric matrix comprises polycaprolactone in combination with a second polymer. In some embodiments, the polycaprolactone and the second polymer are combined in a ratio of about 4:1 or about 9:1. In some embodiments, the second polymer is selected from cyclodextrin, F68, and polyethylene glycol. In some embodiments, the biocompatible polymeric matrix comprises polycaprolactone and F68 in a ratio of about 4:1. In some embodiments, the biocompatible polymeric matrix comprises polycaprolactone and polyethylene glycol in a ratio of about 65:35 as, in some embodiments, such a combination and/or ratio of polymers is useful for increasing the release of a phytochemical or other therapeutic agent from the biocompatible polymeric matrices of the presently-disclosed subject matter.

A composition of the presently-disclosed subject matter can be formulated by dissolving one or more polymers in an appropriate solvent to initiate the formation of the biocompatible polymeric matrix. One or more phytochemical agents are then dissolved in either the same solvent as the one or more polymers or another appropriate solvent depending on the solubility of the particular phytochemical agent. After mixing the polymer solution and the solution of phytochemical agents, the solvents can then be evaporated under reduced pressure to produce a composition where the phytochemical agents are embedded or entrapped within a polymeric matrix.

As discussed herein above, previously phytochemical agents generally have been delivered orally through the diet of a subject. Indeed, almost all published animal studies to date have used a dietary route for administering phytochemical agents, with the dosages of the phytochemical agents ranging from a 10-1000 mg/kg per day in a given diet. When these dose ranges are extrapolated for use in clinical studies, however, the dosage range becomes alarmingly high and thus imposes a risk of toxicity to the subject. By incorporating the phytochemical agents into a biocompatible polymeric matrix, such as those disclosed herein, the inventors of the presently-disclosed subject matter have discovered a composition that effectively releases phytochemical agents at levels that are significantly lower relative to levels provided by a dietary route (i.e., oral delivery) and furthers provides constant, steady-state dosages of the phytochemical agents over a time period, or in other words, provides a "controlled low dose" of the phytochemical agents. Incorporation of a predetermined-amount of a phytochemical agent into a biocompatible polymeric matrix of the presently-disclosed subject matter allows for similar amounts of the phytochemical agent to be released each day as the agent diffuses from the matrix and the biocompatible polymeric matrix degrades in a uniform manner. As such, the presently-disclosed compositions are capable of lowering the effective dose delivered to a given subject, if desired, to thereby minimize toxicity while also delivering the controlled dose at a constant, steady-state level over extended time periods to increase bioavailability and to elicit a biological response.

In some embodiments, the controlled low dose of the phytochemical agent is released over a time period of at least about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, or about 24 months from the time of administration. In some embodiments, a bolus dose of the phytochemical agent can be released from the biocompatible polymeric matrix over a time period of about 1 to about 2 weeks from the time of administration, and the controlled low dose of the phytochemical agent is released over a time period beginning at about 2 to about 3 weeks after administration and extending to about 4, about 5, about 6, about 7, about 8, about 9, about 10, about 11, about 12, about 13, about 14, about 15, about 16, about 17, about 18, about 19, about 20, about 21, about 22, about 23, or about 24 months from the time of administration. In some embodiments, a composition of the presently-disclosed subject matter is provided that releases a controlled low dose of the phytochemical agent over a time period of at least about 18 months.

As used herein, the term "phytochemical agent" refers to a non-nutritive plant-derived compound, or an analog thereof, that is capable of "treating" a cancer, as defined herein below. Examples of phytochemical agents include, but are not limited to compounds such as monophenols; flavonoids, such as flavonols, flavanones, flavones, flavan-3-ols, anthocyanins, anthocyanidins, isoflavones, dihydroflavonols, chalcones, and coumestans; phenolic acids; hydroxycinnamic acids; lignans; tyrosol esters; stillbenoids; hydrolysable tannins; carotenoids, such as carotenes and xanthophylls; monoterpenes; saponins; lipids, such as phytosterols, tocopherols, and omega-3,6,9 fatty acids; diterpenes; triterpinoids; betalains, such as betacyanins and betaxanthins; dithiolthiones; thiosulphonates; indoles; and glucosinolates. As another example of a phytochemical agent disclosed herein, the phytochemical agent can be an analog of a plant-derived compound, such as oltipraz, which is an analog of 1,2-dithiol-3-thione, a compound that is found in many cruciferous vegetables. Table 1 provides a list of specific phytochemical agents that are exemplary of the broader classes of phytochemical agents described herein above.

TABLE 1

List of Exemplary Phytochemical Agents.

PHENOLIC COMPOUNDS

Monophenols
    Apiole
    Carnosol
    Carvacrol
    Dillapiole
    Rosemarinol
Phenolic acids
    Ellagic acid
    Gallic acid
    Salicylic acid
    Tannic acid
    Vanillin
    Capsaicin
    Curcumin
    Plumbagin
Hydroxycinnamic acids
    Caffeic acid
    Chlorogenic acid
    Cinnamic acid
    Ferulic acid
    Coumarin
Lignans (phytoestrogens)
    Silymarin
    Matairesinol
    Secoisolariciresinol
    Pinoresinol
    Lariciresinol
Tyrosol esters
    Tyrosol
    Hydroxytyrosol
    Oleocanthal
    Oleuropein
Stilbenoids
    Resveratrol
    Pterostilbene
    Piceatannol
Hydrolyzable Tannins
    Punicalagins
Flavonoids (polyphenols)
    Flavonols

TABLE 1-continued

List of Exemplary Phytochemical Agents.

Quercetin
Gingerol
Kaempferol
Myricetin
Rutin
Isorhamnetin
Flavanones
    Hesperidin
    Naringenin
    Silybin
    Eriodictyol
Flavones
    Apigenin
    Tangeritin
    Luteolin
Flavan-3-ols
    Catechins
    Gallocatechin
    Epicatechin
    Epigallocatechin
    Epigallocatechin gallate
    Epicatechin-gallate
    Theaflavin
    Theaflavin-gallate
    Theaflavin-digallate
    Thearubigins
Anthocyanins
& Anthocyanidins
    Pelargonidin
    Peonidin
    Cyanidin
    Delphinidin
    Malvidin
    Petunidin
Isoflavones (phytoestrogens)
    Daidzein
    Genistein
    Equol
    Glycitein
Dihydroflavonols
Chalcones
Coumestans
    Coumestrol
TERPENES

Carotenoids
(tetraterpenoids)
    Carotenes
        α-Carotene
        β-Carotene
        γ-Carotene
        δ-Carotene
    Tocotrienols
    Tocopherols
    Lycopene
    Neurosporene
    Phytofluene
    Phytoene
    Xanthophylls
        Canthaxanthin
        Cryptoxanthin
        Zeaxanthin
        Astaxanthin
        Lutein
        Rubixanthin
Monoterpenes
    Limonene
    Perillyl alcohol
Saponins
Lipids
    Phytosterols
        Campesterol
        β-Sitosterol
        γ-Sitosterol
        Stigmasterol
    Tocopherols
    ω-3,6,9 fatty acids
        γ-linolenic acid
Diterpene
    Withaferins
Triterpenoid
    Oleanolic acid
    Ursolic acid
    Betulinic acid
    Moronic acid
    Curcurbitacins
    Lupeol
BETALAINS

Betalains
    Betacyanins
        Betanin
        Isobetanin
        Probetanin
        Neobetanin
    Betaxanthins
        Indicaxanthin
        Vulgaxanthin
ORGANOSULFIDES

Dithiolthiones
    Sulphoraphane
Thiosulphonates
    Allyl methyl trisulfide
    Dialyl sulfide
INDOLES, GLUCOSINOLATES

Indole-3-carbinol
sulforaphone
3,3'-Diindolylmethane
Sinigrin
Allicin
Alliin
Allyl isothiocyanate
Piperine In some embodiments, the phytochemical agent is selected from curcumin, green tea polyphenols, punicalagin, diindolylmethane, oltipraz, tocotrienol, tocopherol, plumbagin, cyanidin, delphinidin, lycopene, lupeol, curcurbitacin-B, Withaferin A, indole-3-carbinol, genestein, equol, resveratrol, co-enzyme Q-10, ellagic acid, petunidin, malvidin, peonidin, fennel extract, and combinations thereof. In some embodiments, the phytochemical agent is a combination of oltipraz and curcumin; curcumin, ellagic acid, co-enzyme Q-10, and lycopene; curcumin, green tea polyphenols, diindolylmethane, and punicalagin; delphinidin, petunidin, malvidin, peonidin, and cyanidin; or punicalagin and delphinidin.

In some embodiments of the presently-disclosed subject matter, one or more phytochemical agents are incorporated into and a released from a single biocompatible polymeric matrix. In some embodiments, a second biocompatible polymeric matrix can be provided that incorporates at least one phytochemical agent such that multiple biocompatible polymeric matrices are provided, wherein each biocompatible polymeric matrix incorporates at least one phytochemical agent.

In some embodiments, a composition is provided that comprises a biocompatible matrix comprising polycaprolactone and F68 in a ratio of about 4:1 that incorporates an effective amount of curcumin such that the composition releases a controlled low dose of curcumin over a time period.

As described above, various phytochemical agents can be incorporated into and released from the biocompatible polymeric matrices of the presently-disclosed subject matter. In some embodiments, the phytochemical agent comprises about 2% to about 50% of the weight of the one or more polymers comprising the biocompatible polymeric matrix. In some embodiments, the phytochemical agents comprises about 1%, about 2%, about 3%, about 4%, about 5%, about 10%, about 15%, about 18%, about 19%, about 20%, about 21%, about 22%, about 25%, about 30%, about 35%, about 40%, about 45%, about 46%, about 47%, about 48%, about 49%, or about 50% of the weight of the one or more polymers. In some embodiments, the phytochemical agents are added to between about 2% to about 20% of the polymer weight. As will be recognized by those of ordinary skill in the art, the optimum amount of each phytochemical agent that is incorporated into a biocompatible polymeric matrix can vary depending on the particular phytochemical agents used and the desired dosage to be achieved. Determination and adjustment of the amount of a phytochemical agent to be used in a particular composition or application, as well as when and how to make such adjustments, can be ascertained using only routine experimentation.

Any phytochemical agent of the presently-disclosed subject matter can be provided in the form of a pharmaceutically acceptable salt or solvate. A salt can be formed using a suitable acid and/or a suitable base. Suitable acids that are capable of forming salts with the phytochemical agents of the presently disclosed subject matter include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid, or the like. Suitable bases capable of forming salts with the phytochemical agents of the presently disclosed subject matter include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine, and the like), and optionally substituted ethanolamines (e.g. ethanolamine, diethanolamine, and the like).

As used herein, the term "solvate" refers to a complex or aggregate formed by one or more molecules of a solute, e.g. a phytochemical agent or a pharmaceutically-acceptable salt thereof, and one or more molecules of a solvent. Such solvates are typically crystalline solids having a substantially fixed molar ratio of solute and solvent. Representative solvents include, but are not limited to, water, methanol, ethanol, isopropanol, acetic acid, and the like. When the solvent is water, the solvate formed is a hydrate. As such, the term "pharmaceutically-acceptable salt or solvate thereof" is intended to include all permutations of salts and solvates, such as a solvate of a pharmaceutically-acceptable salt of a phytochemical agent.

In some embodiments of the presently-disclosed subject matter, a composition is provided that includes a biocompatible polymeric matrix incorporating an effective amount of a phytochemical agent where the composition further comprises a polymeric coating surrounding the initial composition. In some embodiments, the polymeric coating is comprised of polycaprolactone. In some embodiments, the polymeric coating is comprised of about 5, about 10, about 15, about 20, about 25, about 30, about 35, about 40, about 45, about 50 layers, about 75, about 100, about 125, about 150, about 175, or up to about 200 layers of the polymer around the initial composition. In some embodiments, the polymeric coating is comprised of about 5 to about 40 layers of the polymer around the initial composition. In some embodiments, providing a polymeric coating around the compositions of the presently-disclosed subject matter prevents or reduces an amount of phytochemical agent that is initially released from the compositions in a high concentration (i.e., a burst release) such that the polymeric coating provides a more sustained release and/or prevents toxicity that may otherwise occur as a result of the high initial release of the phytochemical agents from the compositions.

In some embodiments of the presently-disclosed subject matter, the compositions themselves, i.e., the biocompatible matrices incorporating the phytochemical agents, are provided in the form of a coating. For example, in some embodiments of the presently-disclosed subject matter, the compositions can be used to surround or otherwise envelop an additional composition, and thus, act as a coating while still providing a sustained release of the phytochemical agents.

In some embodiments, a composition is provided that further comprises an effective amount of a chemotherapeutic agent that is incorporated into and released from a biocompatible polymeric matrix that also incorporates an effective amount of a phytochemical agent or from a second biocompatible polymeric matrix. Examples of such chemotherapeutic agents include, but are not limited to, platinum coordination compounds such as cisplatin, carboplatin or oxalyplatin; taxane compounds, such as paclitaxel or docetaxel; topoisomerase I inhibitors such as camptothecin compounds for example irinotecan or topotecan; topoisomerase II inhibitors such as anti-tumor podophyllotoxin derivatives for example etoposide or teniposide; anti-tumor vinca alkaloids for example vinblastine, vincristine or vinorelbine; anti-tumor nucleoside derivatives for example 5-fluorouracil, gemcitabine or capecitabine; alkylating agents, such as nitrogen mustard or nitrosourea for example cyclophosphamide, chlorambucil, carmustine or lomustine; anti-tumor anthracycline derivatives for example daunorubicin, doxorubicin, idarubicin or mitoxantrone; HER2 antibodies for example trastuzumab; estrogen receptor antagonists or selective estrogen receptor modulators for example tamoxifen, toremifene, droloxifene, faslodex or raloxifene; aromatase inhibitors, such as exemestane, anastrozole, letrazole and vorozole; differentiating agents such as retinoids, vitamin D and retinoic acid metabolism blocking agents (RAMBA) for example accutane; DNA methyl transferase inhibitors for example azacytidine; kinase inhibitors for example flavoperidol, imatinib mesylate or gefitinib; farnesyltransferase inhibitors; HDAC inhibitors; other inhibitors of the ubiquitin-proteasome pathway for example VELCADE®; or YONDELIS®.

In some embodiments, a composition is provided that further comprises an effective amount of a anti-inflammatory agent that is incorporated into and released from a biocompatible polymeric matrix that also incorporates an effective amount of a phytochemical agents or from a second biocompatible polymeric matrix. Example of anti-inflammatory agents that can be used in accordance with the methods and compositions of the presently-disclosed subject matter include, but are not limited to, non-steroidal anti-inflammatory agents (NSAIDS), such as aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone, acetaminophen, and combinations thereof; COX-2 inhibitors, such as nimesulide, flosulid, celecoxib, rofecoxib, parecoxib sodium, valdecoxib, etoricoxib, etodolac, meloxicam, and combinations thereof; glucocorticoids, such as hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, rapamycin; or others or analogues of these agents or combinations thereof.

Further provided, in some embodiments of the presently-disclosed subject matter are methods for treating a cancer. In some embodiments, a method for treating a cancer is provided that comprises administering to a subject in need thereof an effective amount of a composition of the presently-disclosed subject matter comprising a biocompatible polymeric matrix incorporating a phytochemical agent, wherein the phytochemical agent is incorporated into and released over a time period from the biocompatible polymeric matrix at a controlled low dose of the phytochemical agent.

As used herein, the terms "treating" or "treatment" relate to any treatment of a cancer including, but are not limited to, therapeutic treatment and prophylactic treatment of a cancer. With regard to therapeutic treatment of a cancer, the terms "treating" or "treatment" include, but are not limited to, inhibiting the progression of a cancer, arresting the development of a cancer, reducing the severity of a cancer, ameliorating or relieving one or more symptoms associated with a cancer, and causing a regression or a cancer or one or more symptoms associated with a cancer.

As noted herein above, the terms "treating" or "treatment," as used herein, further include the prophylactic treatment of a cancer including, but not limited to, any action that occurs before the development of a cancer. It is understood that the degree of prophylaxis need not be absolute (e.g. the complete prophylaxis of a cancer such that the subject does not develop a cancer at all), and that intermediate levels of prophylaxis, such as increasing the time required for at least one symptom resulting from a cancer to develop, reducing the severity or spread of a cancer in a subject, or reducing the time that at least one adverse health effect of a cancer is present within a subject, are all examples of prophylactic treatment of a cancer.

As further non-limiting examples of the treatment of a cancer by a composition described herein, treating a cancer can include, but is not limited to, killing cancer cells, inhibiting the development of cancer cells, inducing apoptosis in cancer cells, reducing the growth rate of cancer cells, reducing the incidence or number of metastases, reducing tumor size, inhibiting tumor growth, reducing the available blood supply to a tumor or cancer cells, promoting an immune response against a tumor or cancer cells, reducing or inhibiting the initiation or progression of a cancer, increasing the lifespan of a subject with a cancer, or inhibiting or reducing the formation of DNA adducts by chemical carcinogens.

In some embodiments of the presently-disclosed subject matter, a method for treating a cancer is provided wherein the treating comprises inhibiting or reducing the formation of DNA adducts. The formation of DNA adducts (i.e. carcinogens covalently bound to DNA) is widely considered a prerequisite for the initiation and progression of cancer development. Many carcinogens are known to induce the formation of DNA adducts (Hemminki, 1995) and the presence of DNA adducts in humans has been strongly correlated with an increased risk for cancer development (Santella, 1997). For example, human studies have shown a higher accumulation of tissue DNA adducts in cigarette smokers than in non-smokers or individuals who have never smoked, indicating that DNA adduct formation is a viable target for the treatment of cancer.

As used herein, the term "cancer" refers to all types of cancer, neoplasm, or malignant tumors found in subjects, including leukemias, carcinomas, and sarcomas. Examples of cancers include, but are not limited to, cancer of the brain, bladder, breast, cervix, colon, head and neck, kidney, lung, non-small cell lung, melanoma, mesothelioma, ovary, prostate, sarcoma, stomach, uterus, skin, esophagus, pancreas, and medulloblastoma.

In some embodiments of the presently-disclosed subject matter, the cancer is selected from the group consisting of breast cancer, lung cancer, and cervical cancer. As used herein, the term "breast cancer" is meant to refer to any cancer of the breast and includes, but is not limited to, mammary carcinoma, adenocarcinoma, lobular (small cell) carcinoma, intraductal carcinoma, medullary breast cancer, mucinous breast cancer, tubular breast cancer, papillary breast cancer, Paget's disease, inflammatory breast cancer, and hormone-dependent and hormone-independent tumors of the breast. The term "cervical cancer" is meant to refer to any cancer of the cervix and includes, but is not limited to, squamous cell carcinomas, adenocarcinomas, and adenosquamous carcinomas, or mixed carcinomas. The term "lung cancer" is meant to refer to any cancer of the lung and includes non-small cell lung carcinomas and small cell lung carcinomas. Examples of non-small cell lung carcinomas include, but are not limited to, squamous cell lung carcinomas, adenocarcinomas, bronchio-alveolar carcinomas, adenosquamous carcinomas, papillary adenocarcinomas, mucoepidermoid carcinomas, adenoid cystic carcinomas, large cell carcinomas, and giant cell and spindle cell carcinomas.

In some embodiments of the presently-disclosed methods of treating a cancer, the subject is at an increased risk of developing a primary cancer. In some embodiments, the primary cancer is selected from the group consisting of breast cancer, lung cancer, and cervical cancer.

The phrase "increased risk" is used herein to refer to those subjects whose likelihood of developing a cancer in their lifetime is increased, as compared to a normal subject. Such subjects may be identified by factors that include, but are not limited to: a genetic pre-disposition to certain cancers; life style choices such as tobacco smoking, tobacco chewing, or dietary habits; medical treatments such as immunosuppression; or exposure to carcinogenic agents in the environment, such as viruses, chemicals, medications, and radiation, or age-related factors, such as hormone levels. For example, subjects at an increased risk of developing breast cancer may be identified by factors such as age, gender, early age of menarche, late age of menopause, nulliparity, use of oral contraceptives, prolonged estrogen replacement therapy, breast density, or mutations in two known breast-cancer related genes, BRCA1 and BRCA2. As another example, subjects at risk of developing cervical cancer may be identified by factors such as human papilloma virus (HPV) infection, life style choices such as tobacco smoking or dietary habits, human immunodeficiency virus (HIV) infection, use of oral contraceptives, multiple pregnancies, hormonal therapies, genetic predispositions to cervical cancer, and cervical dysplasia.

As used herein, the term "primary cancer" is meant to refer to an original tumor or cancer cell in a subject. Such primary cancers are usually named for the part of the body in which the primary cancer originates. Furthermore, a "secondary cancer" is used herein to refer to a cancer which has spread, or metastasized, from an initial site (i.e. a primary cancer site) to another site in the body of a subject, a cancer which represents a residual primary cancer, or a cancer that has originated from treatment with an antineoplastic agent(s) or radiation or both. In this regard, the term "secondary cancer" is thus not limited to any one particular type of cancer, including the type of primary cancer from which it derived. In some embodiments of the presently-disclosed subject matter, a method of preventing or treating a cancer is further provided where the subject is at risk of developing a secondary cancer.

As used herein, the term "subject" includes both human and animal subjects. Thus, veterinary therapeutic uses are provided in accordance with the presently disclosed subject matter. As such, the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

For administration of a composition as disclosed herein, conventional methods of extrapolating human dosage based on doses administered to a murine animal model can be carried out using the conversion factor for converting the mouse dosage to human dosage: Dose Human per kg=Dose Mouse per kg×12 (Freireich, et al., (1966) *Cancer Chemother. Rep.* 50:219-244). Drug doses can also be given in milligrams per square meter of body surface area because this method rather than body weight achieves a good correlation to certain metabolic and excretionary functions. Moreover, body surface area can be used as a common denominator for drug dosage in adults and children as well as in different animal species as described by Freireich, et al. (*Cancer Chemother. Rep.* 1996; 50:219-244). Briefly, to express a mg/kg dose in any given species as the equivalent mg/sq m dose, multiply the dose by the appropriate kg factor. In an adult human, 100 mg/kg is equivalent to 100 mg/kg×37 kg/sq m=3700 mg/m$^2$.

In some embodiments of the presently-disclosed subject matter, the phytochemical agent is administered to a subject by subcutaneous implantation of the biocompatible polymeric matrix incorporating the phytochemical agent. In some embodiments, the phytochemical agent is administered to a subject by implantation of a composition of the presently-disclosed subject matter at a site distant from the site of the cancer. For example, a composition of the presently-disclosed subject matter can be implanted subcutaneously in the arm of a subject such that the phytochemical agents, upon their release into systemic circulation, are capable of treating a breast, cervical, or lung cancer, which is located at a site distant from the site of the implantation of the presently-disclosed composition.

In some embodiments, the phytochemical agent is administered to a subject by implantation of the biochemical polymeric matrix incorporating the phytochemical agent at a site of a cancer or at a site suspected of developing a cancer. As an exemplary method of administering a composition of the presently-disclosed subject matter at the site of a cancer, the biocompatible polymeric composition can be implanted at the site of a tumor, either following surgical removal or resection of the tumor, or can be implanted into the surrounding tissue. As another example of administering a composition of the presently-disclosed subject matter at a site of cancer, the composition need not be implanted internally within the body of a subject, but can be implanted into an external orifice of the subject where a cancer is present. For example, a composition of the presently-disclosed subject matter can be implanted into the cervix of a subject by insertion of the biocompatible polymeric matrix incorporating the phytochemical agent into the cervical canal of a subject. Similarly, if a subject is suffering from cervical dysplasia, a biocompatible matrix incorporating a phytochemical agent can be administered to a site suspected of developing a cancer by the inserting the composition into the cervical canal of the subject such that an effective amount of the phytochemical agent is administered to the cervix of the subject.

The term "effective amount" is used herein to refer to an amount of the composition (e.g., a composition comprising a phytochemical agent that is incorporated into and released from a biocompatible polymeric composition) sufficient to produce a measurable biological response (e.g., inhibition of the development of tumor cells or a reduction in the number of tumor cells). Actual dosage levels of active ingredients in a therapeutic composition of the presently-disclosed subject matter can be varied so as to administer an amount of the active compound(s) that is effective to achieve the desired therapeutic response for a particular subject and/or application. The selected dosage level will depend upon a variety of factors including the activity of the therapeutic composition, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of a therapeutically effective dose, as well as evaluation of when and how to make such adjustments, are known to those of ordinary skill in the art of medicine.

For additional guidance regarding formulation and dose, see U.S. Pat. Nos. 5,326,902 and 5,234,933; PCT International Publication No. WO 93/25521; Berkow, et al., (1997) *The Merck Manual of Medical Information*, Home ed. Merck Research Laboratories, Whitehouse Station, N.J.; Goodman, et al., (2006) *Goodman & Gilman's the Pharmacological Basis of Therapeutics,* 11th ed. McGraw-Hill Health Professions Division, New York; Ebadi. (1998) *CRC Desk Reference of Clinical Pharmacology*. CRC Press, Boca Raton, Fla.; Katzung, (2007) *Basic & Clinical Pharmacology*, 10th ed. Lange Medical Books/McGraw-Hill Medical Pub. Division, New York; Remington, et al., (1990) *Remington's Pharmaceutical Sciences,* 18th ed. Mack Pub. Co., Easton, Pa.; Speight, et al., (1997) *Avery's Drug Treatment: A Guide to the Properties, Choice, Therapeutic Use and Economic Value of Drugs in Disease Management,* 4th ed. Adis International, Auckland/Philadelphia; and Duch, et al., (1998) *Toxicol. Lett.* 100-101:255-263.

Still further provided, in some embodiments of the presently-disclosed subject matter, is a device for insertion into a cervical canal. Referring to FIG. 30, in some embodiments of presently-disclosed subject matter, a device 10 for insertion into a cervical canal includes: a substantially cylindrical shaft 20 having a proximal end 22 and a distal end 24, and defining a canal 26 that extends from the proximal end 22 to the distal end 24; and, a cap 30 attached to the proximal end 22 of the cylindrical shaft 20, said cap including a central opening 32 in registry with the canal defined by the shaft.

Referring now to FIG. 33, an exemplary device 10 can be inserted into the cervix of a subject to "treat" a cancer, as defined herein. In some embodiments, a device 10 for insertion into a cervical canal is provided wherein the cylindrical shaft 20 is suitably adapted for engaging the walls of a cervical canal and the bottom surface 34 of the cap 30 is suitably adapted for engaging an external orifice of the uterus. In some embodiments, the bottom surface 34 of the cap 30 has a concave shape such that the bottom surface 34 of the cap 30 suitably engages the external orifice of the uterus. In some embodiments, a device 10 for insertion into a cervical canal is provided wherein the distal end 24 of the shaft 20 is tapered such that the device 10 is easily inserted into the cervix of a subject. In some embodiments, the canal 26 defined by the shaft 20 allows for the passage of bodily fluids from the uterus.

In some embodiments, the device is designed and fabricated such that the device contacts a transformation zone of a cervix of a subject. As used herein, the term "transformation zone" refers to a region of a cervix that separates the ectocervical region, which is comprised of squamous cells, from the endocervical region, which is comprised of columnar cells. In younger subjects, the transformation zone is typically found on the outside of the external orifice of the uterus. However, as a subject ages, the transformation zone decreases in size and reaches the cervical canal. As such, in some embodiments of the presently-disclosed subject matter, a device for cervical insertion is provided that can be utilized to treat cervical cancer in female subjects of all ages by maintaining contact with the transformation zone.

Referring now to FIG. 31, it is contemplated that an exemplary device for insertion into a cervical canal can be adapted for suitable insertion into the cervix of a human subject. In this regard, in some embodiments of the presently-disclosed device for insertion in a cervical canal, a device is provided wherein the cylindrical shaft is about 19 to about 25 mm in length and about 9 to about 11 mm in diameter, the cap is about 20 to 25 mm in diameter, and the canal is about 4 mm to about 5 mm in diameter.

As shown in FIG. 32A-D, an exemplary device of the presently-disclosed subject matter can be comprised of a biocompatible polymeric matrix incorporating an effective amount of a phytochemical agent, as described herein. For example, an exemplary device can be fabricated by extruding a dissolved mixture of one or more polymers and one or more phytochemical agents through a suitable mold and dried to provide a suitably shaped device. Further shaping of the device can additionally be performed during the drying process. As will be evident to those of ordinary skill in the art, different shaped molds can be provided such that other devices can be fabricated or adapted to provide suitably shaped or sized devices for insertion or implantation at other anatomical locations.

In some embodiments of the device for insertion into a cervical canal, the phytochemical agent is selected from curcumin, green tea polyphenols, punicalagin, diindolylmethane, oltipraz, tocotrienol, tocopherol, plumbagin, cyanidin, delphinidin, lycopene, lupeol, curcurbitacin-B, Withaferin A, indole-3-carbinol, genestein, equol, resveratrol, co-enzyme Q-10, ellagic acid, petunidin, malvidin, peonidin, fennel extract, and combinations thereof. In some embodiments, the phytochemical agent comprises about 2% to about 50% of the polymer weight.

In some embodiments, a device for cervical insertion is provided where the biocompatible polymeric matrix is comprised of polymers selected from polycaprolactone, cyclodextrin, F68, polyethylene glycol, and combinations thereof. In some embodiments, the biocompatible polymeric matrix comprises polycaprolactone in combination with a second polymer that, in certain embodiments, can be selected from cyclodextrin, F68, and polyethylene glycol. In some embodiments the polycaprolactone and the second polymer are combined in a ratio of about 4:1 or about 9:1. In some embodiments, the biocompatible matrix comprises polycaprolactone and F68 in a ratio of about 4:1 and, in some embodiments, the phytochemical agent comprises curcumin. In some embodiments, the biocompatible polymeric matrix is biodegradable.

The presently-disclosed subject matter is further illustrated by the following specific but non-limiting examples. Some of the following examples are prophetic, notwithstanding the numerical values, results and/or data referred to and contained in the examples. Additionally, the following examples may include compilations of data that are representative of data gathered at various times during the course of development and experimentation related to the present invention.

EXAMPLES

Example 1

Formulation of Compositions

Compositions were prepared by first dissolving two polymers in an appropriate solvent: e.g. a water-insoluble, biodegradable, and biocompatible polycaprolactone (MW 65,000) and a water-soluble cyclodextrin. Polycaprolactone and cyclodextrin (in a 4:1 or 9:1 ratio) were dissolved in 2-5 volumes of dichloromethane (g/ml). Some preparations comprising polycaprolactone as a first polymer included either F68 or polyethylene glycol instead of cyclodextrin. Desired phytochemical agent(s), approximately 2% to 20% or more of the polymer weight, were then dissolved either in the same solvent as the polymer or another appropriate solvent (e.g., ethanol, acetone, tetrahydrofuran), depending upon the phytochemical agent's solubility. Typically, the amounts of phytochemicals incorporated into a biocompatible polymeric matrix ranged from less than 2 mg to as much as 20 mg of phytochemical agent per 100 mg of polymer. Depending on the particular phytochemical agent employed, however, it was possible to incorporate as much as 50 mg or more of the phytochemical agent per 100 mg of polymer.

Figure 1:
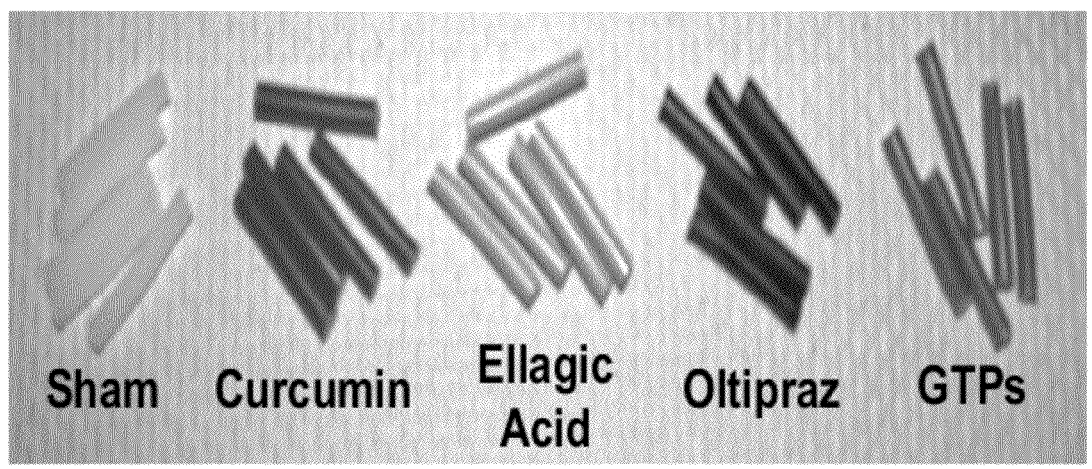
FIG. 1 is a picture of exemplary compositions of the presently-disclosed subject matter, and including an image of a biocompatible polymeric matrix without the incorporation of a phytochemical agent (Sham) and images of biocompatible polymeric matrices incorporating various phytochemical agents including curcumin, ellagic acid, oltipraz, and green tea polyphenols (GTPs).
Figure 2A:
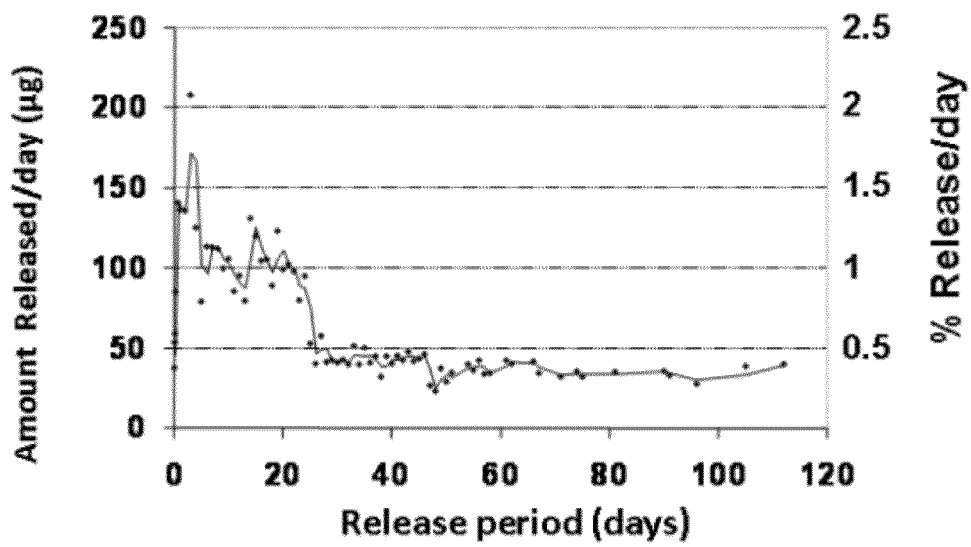
FIG. 2A is a graph depicting the daily release of curcumin from a biocompatible polymeric matrix where the amount (µg) of curcumin released per day (y-axis) and the percentage of curcumin released from the matrix per day (y-axis) are plotted against a release period measured in days (x-axis).
Figure 2B:
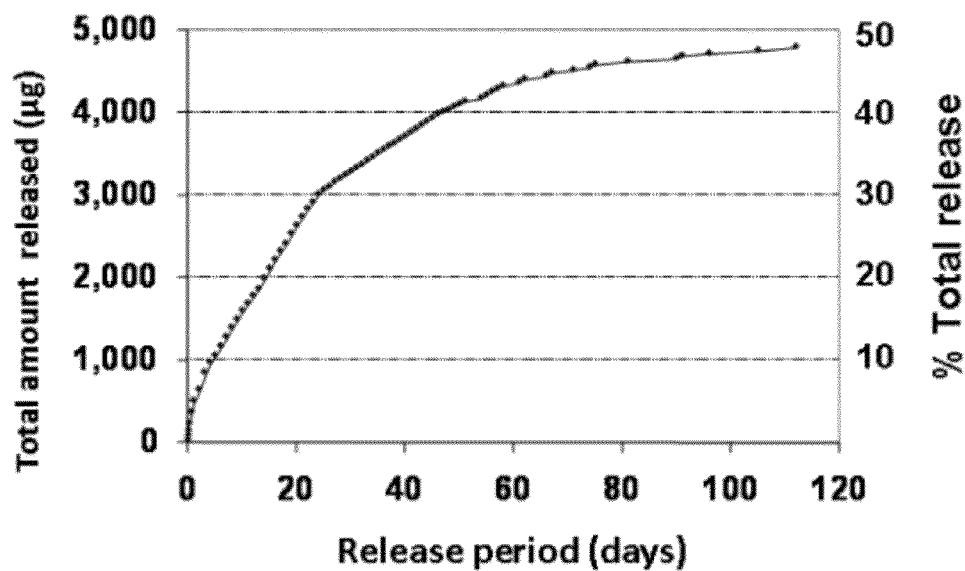
FIG. 2B is a graph depicting the cumulative release of curcumin from a biocompatible polymeric matrix where the total amount (µg) of curcumin released from the matrix (y-axis) and the total percentage of curcumin released from the matrix (y-axis) are plotted against a release period measured in days (x-axis).
Figure 3A:
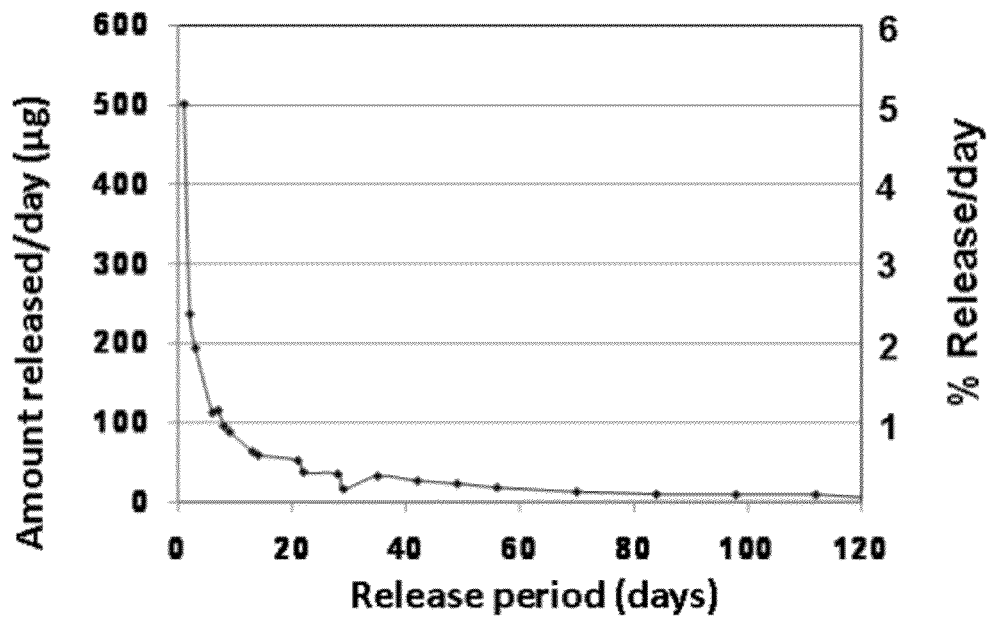
FIG. 3A is a graph depicting the daily release of GTPs from a biocompatible polymeric matrix where the amount (µg) of GTPs released per day (y-axis) and the percentage of GTPs released from the matrix per day (y-axis) are plotted against a release period measured in days (x-axis).
Figure 3B:
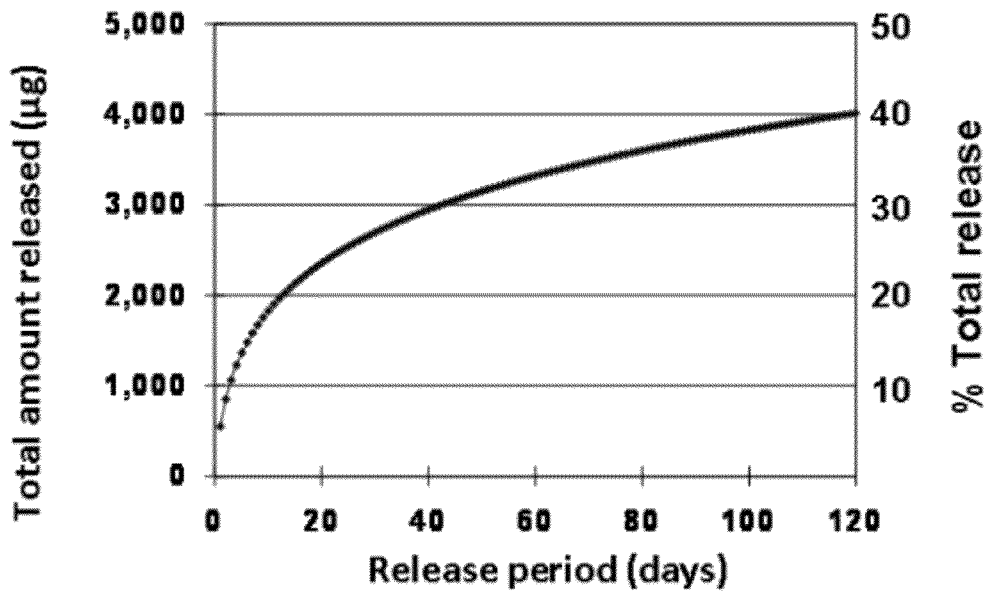
FIG. 3B is a graph depicting the cumulative release of GTPs from a biocompatible polymeric matrix where the total amount (μg) of GTPs released from the matrix (y-axis) and the total percentage of GTPs released from the matrix (y-axis) are plotted against a release period measured in days (x-axis).
Figure 4A:
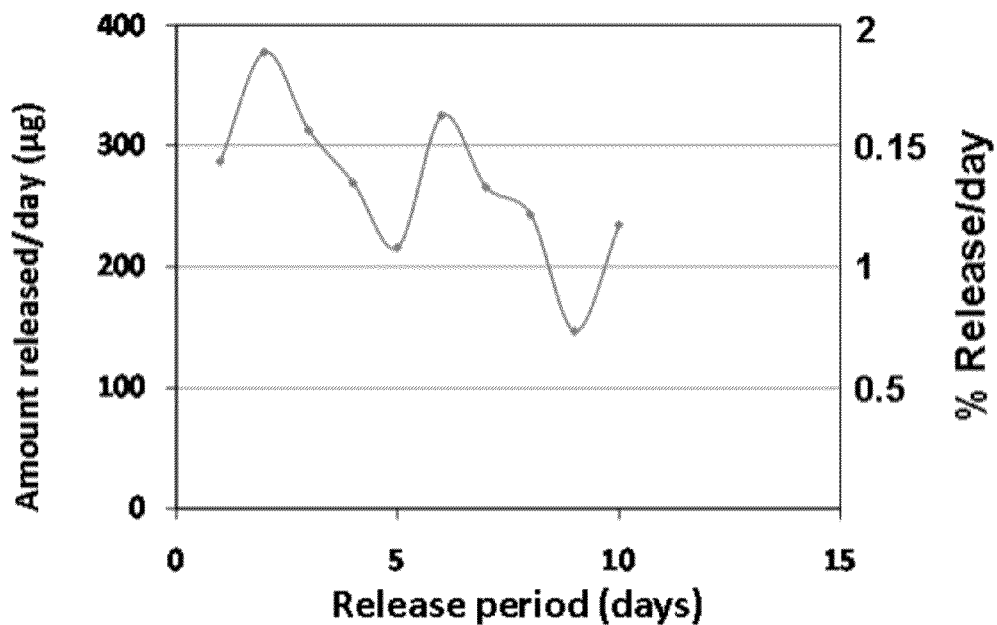
FIG. 4A is a graph depicting the daily release of DIM from a biocompatible polymeric matrix where the amount (μg) of DIM released per day (y-axis) and the percentage of DIM released from the matrix per day (y-axis) are plotted against a release period measured in days (x-axis).
Figure 4B:
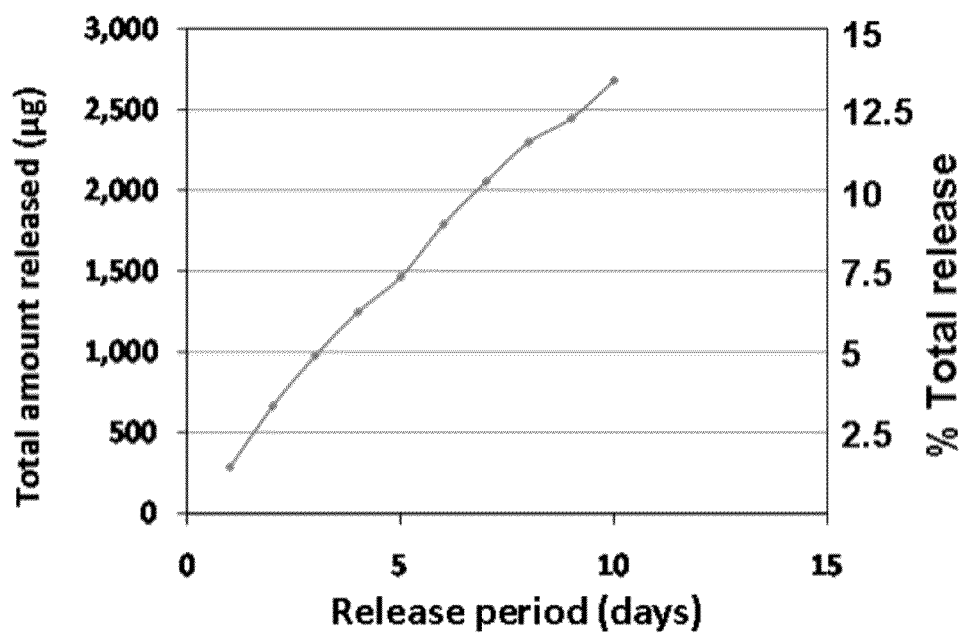
FIG. 4B is a graph depicting the cumulative release of DIM from a biocompatible polymeric matrix where the total amount (μg) of DIM released from the matrix (y-axis) and the total percentage of DIM released from the matrix (y-axis) are plotted against a release period measured in days (x-axis).
Figure 5A:
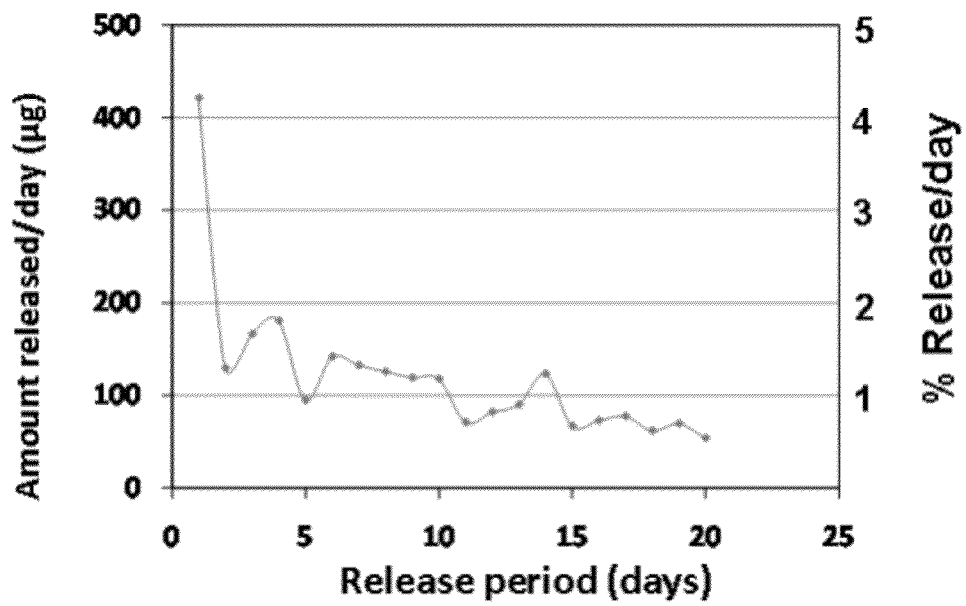
FIG. 5A is a graph depicting the daily release of punicalagins from a biocompatible polymeric matrix where the amount (μg) of punicalagins released per day (y-axis) and the percentage of punicalagins released from the matrix per day (y-axis) are plotted against a release period measured in days (x-axis).
Figure 5B:
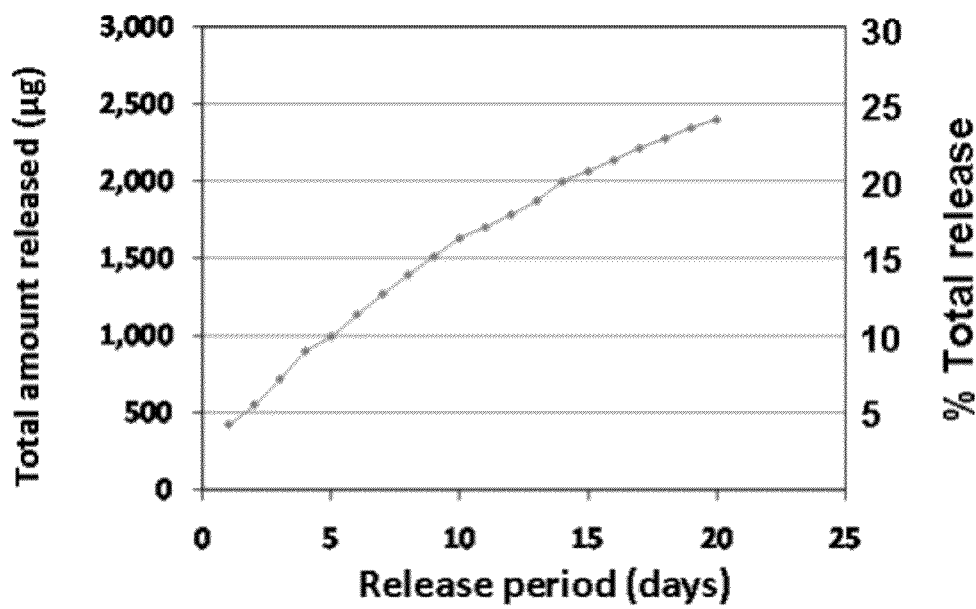
FIG. 5B is a graph depicting the cumulative release of punicalagins from a biocompatible polymeric matrix where the total amount (μg) of punicalagins released from the matrix (y-axis) and the total percentage of punicalagins released from the matrix (y-axis) are plotted against a release period measured in days (x-axis).
Figure 6A:
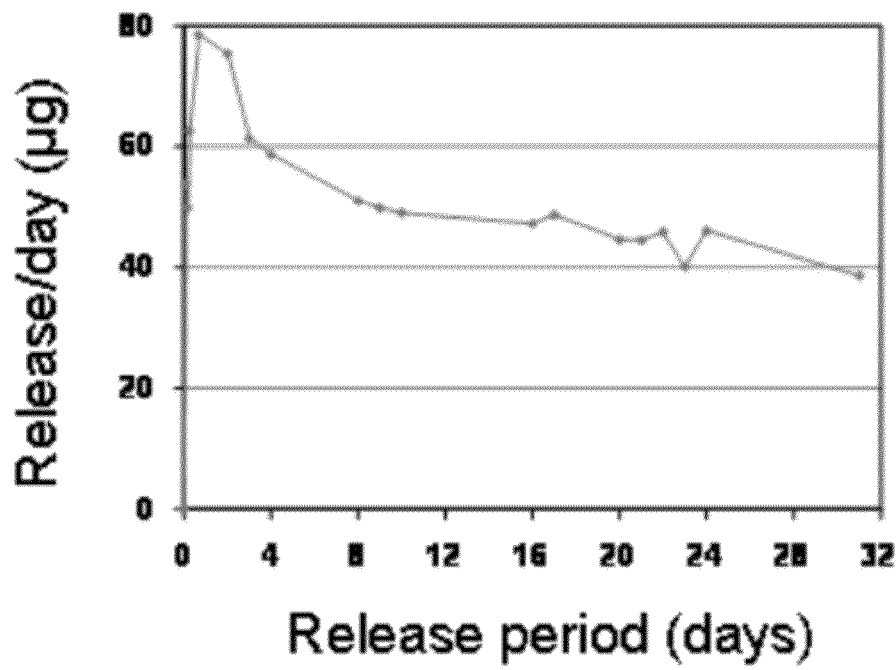
FIG. 6A is a graph depicting the daily release of oltipraz from a biocompatible polymeric matrix where the amount (μg) of oltipraz released per day (y-axis) is plotted against a release period measured in days (x-axis).
Figure 6B:
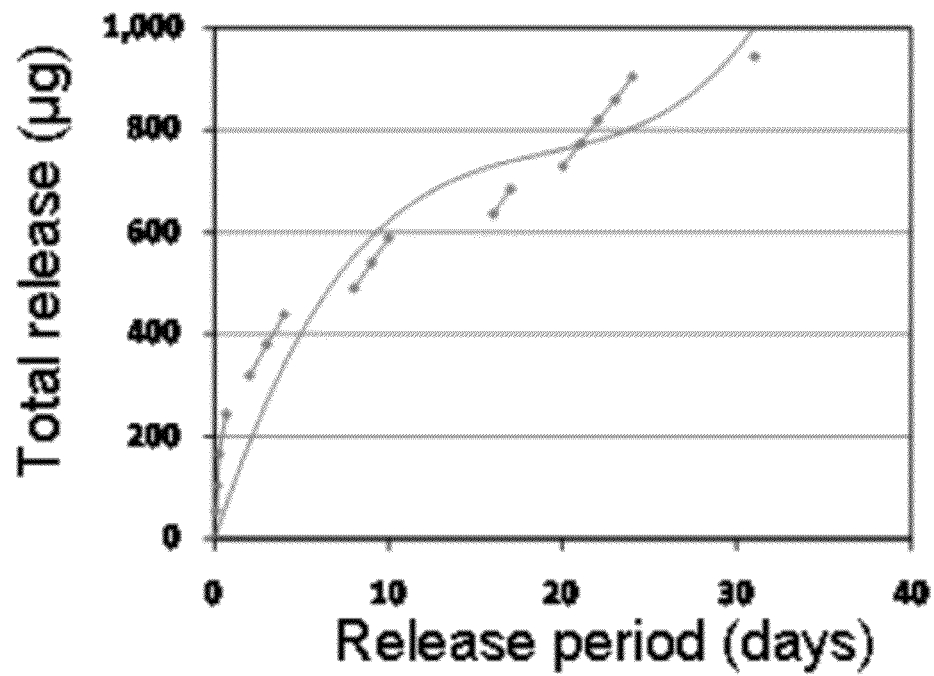
FIG. 6B is a graph depicting the cumulative release of oltipraz from a biocompatible polymeric matrix where the total amount (μg) of oltipraz released from the matrix (y-axis) is plotted against a release period measured in days (x-axis).
Figure 7A:
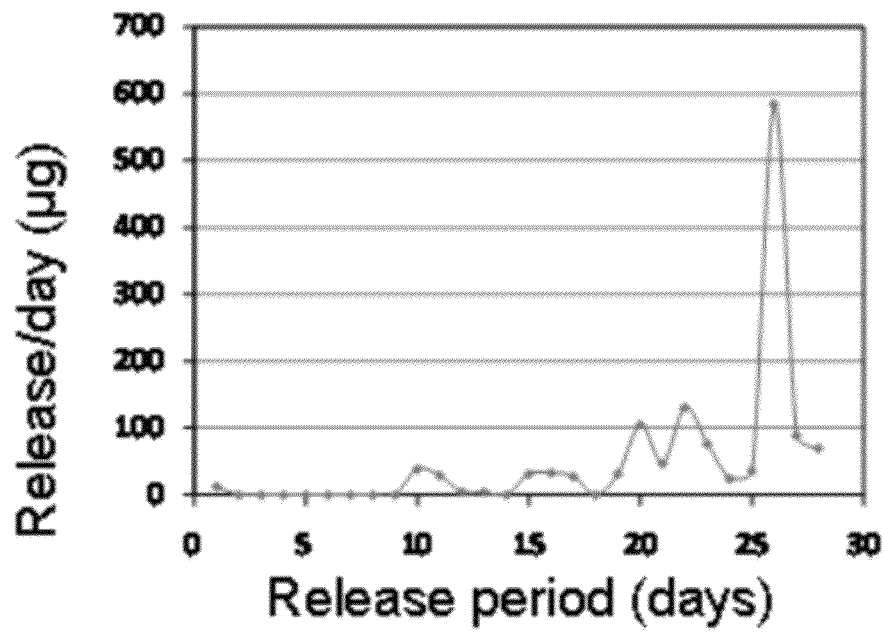
FIG. 7A is a graph depicting the daily release of lycopene from a biocompatible polymeric matrix where the amount (μg) of lycopene released per day (y-axis) is plotted against a release period measured in days (x-axis).
Figure 7B:
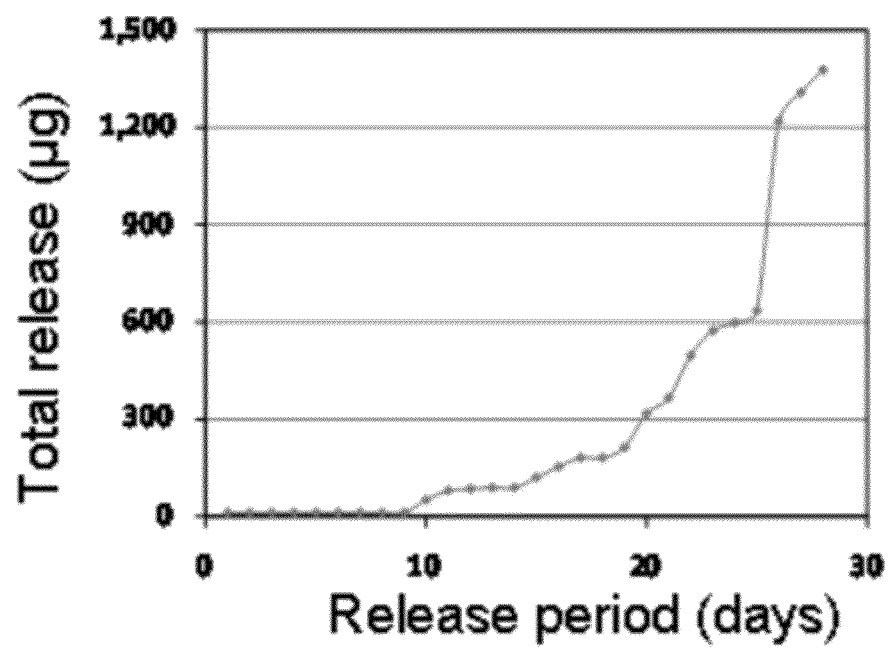
FIG. 7B is a graph depicting the cumulative release of lycopene from a biocompatible polymeric matrix where the total amount (μg) of lycopene released from the matrix (y-axis) is plotted against a release period measured in days (x-axis).

After the phytochemical agent and the polymers were dissolved in appropriate solvents, the polymer solution and the phytochemical agent solution were mixed in a 100-200 ml glass beaker, and the solvents were evaporated under reduced pressure. The resulting composition was a polymeric material incorporating a phytochemical agent in a matrix, which was then cut into small pieces and filled in a syringe attached to a silastic tubing (4-6 cm long and 2.2 mm diameter). This entire assembly was then placed at 70-80° C. for several minutes to facilitate the extrusion of a molten polymeric material/phytochemical agent into the silastic tubing. After an appropriate amount of time had passed, the molten polymeric material/phytochemical agent was extruded into the silastic tubing and a few minutes after cooling at room temperature, the solid compositions were removed from the tubing and cut to produce solid, cylindrical compositions that were approximately 1 mm to 2.2 mm in diameter and approximately 1 cm to 3 cm in length. Exemplary compositions comprising a biocompatible polymeric matrix by itself (sham) or incorporating curcumin, ellagic acid, oltipraz, or green tea polyphenols (GTPs) are shown in FIG. 1.

Example 2

In Vitro Release of Phytochemical Agents

To determine daily release of the phytochemical agents in vitro, compositions, which were approximately 1 cm in length and approximately 1 mm to 2.2 mm in diameter, comprising a biocompatible polymeric matrix incorporating a desired phytochemical agent (20% w/w) were placed in a release medium (5-20 ml phosphate-buffered-saline (pH 7.4) containing 10% bovine serum) at 37° C. with constant agitation in a water bath to simulate an in vivo scenario. The medium was replaced daily and the amount of phytochemical agents released from the compositions per day was measured spectrophotometrically against a standard curve and expressed as micrograms per day.

Figure 8A:
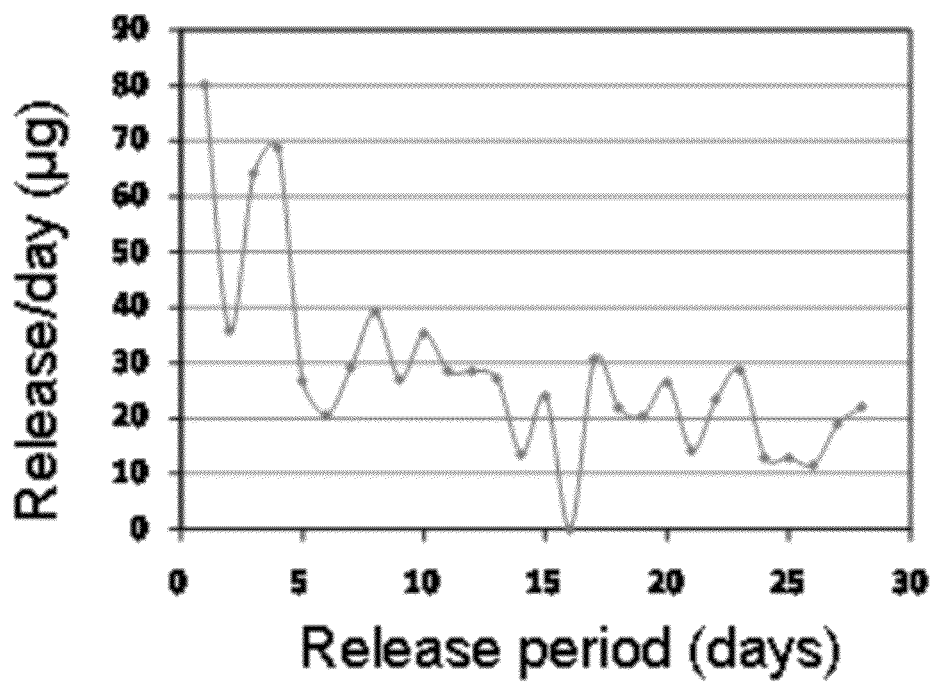
FIG. 8A is a graph depicting the daily release of resveratrol from a biocompatible polymeric matrix where the amount (μg) of resveratrol released per day (y-axis) is plotted against a release period measured in days (x-axis).
Figure 8B:
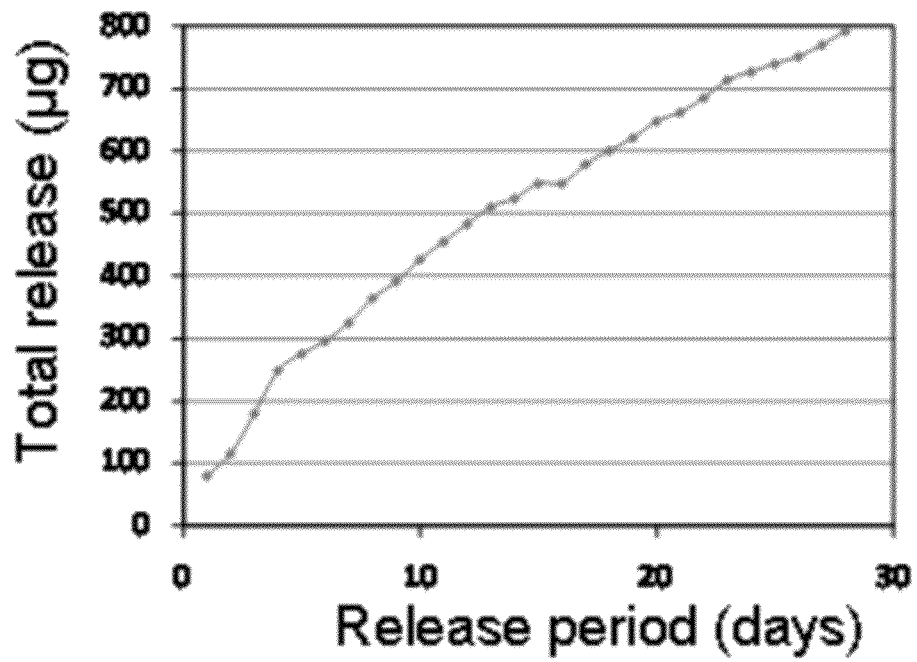
FIG. 8B is a graph depicting the cumulative release of resveratrol from a biocompatible polymeric matrix where the total amount (μg) of resveratrol released from the matrix (y-axis) is plotted against a release period measured in days (x-axis).

FIGS. 2 to 8 show the amount of exemplary phytochemical agents released per day and the total amount of phytochemical agents released from a biocompatible polymeric matrix of the presently-disclosed subject matter over a particular time period, including data for curcumin (FIGS. 2A and 2B), GTPs (FIGS. 3A and 3B), diindolylmethane (DIM, FIGS. 4A and 4B), punicalagins (FIGS. 5A and 5B), oltipraz (FIGS. 6A and 6B), lycopene (FIGS. 7A and 7B) and resveratrol (FIGS. 8A and 8B). From this in vitro data, it can be seen that for a typical phytochemical agent approximately 4% to 10% of the phytochemical agent is released during the first week, followed by 2% to 5% per week for the following 2 to 3 weeks, and then after 3 weeks approximately 0.2 to 0.5% per week for periods up to several months. Without wishing to be bound by any particular theory, it is believed that the amount of phytochemical agents released from each biocompatible polymeric matrix is dependent on the lipophilicity of the phytochemical agent, with a higher initial release for highly water-soluble compounds (e.g. green tea polyphenols) and a somewhat lower release for more lipophilic agents (e.g. curcumin).

Example 3

Effect of Phytochemical Agent Load on In Vitro Release of Phytochemicals from a Biocompatible Polymeric Matrix To determine the effect of incorporating various amounts of phytochemical agents into a biocompatible polymeric matrix on the in vitro release of the agents, 2% w/w, 5% w/w, and 20% w/w of curcumin were incorporated into separate biocompatible polymeric matrices and placed in a release medium (5-20 ml phosphate-buffered-saline (pH 7.4) containing 10% bovine serum) at 37° C. with constant agitation in a water bath to simulate an in vivo scenario. The medium was replaced daily and the amount of curcumin released from each composition per day was measured spectrophotometrically against a standard curve and expressed as μg/day.

Figure 9A:
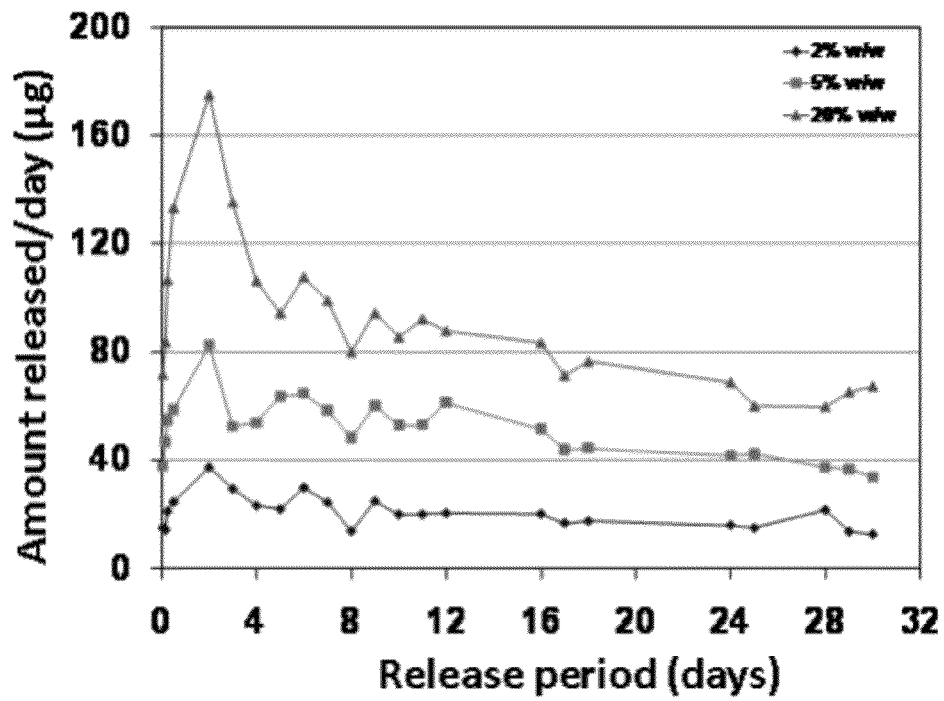
FIG. 9A is a graph depicting the daily release of curcumin from each of the biocompatible polymeric matrices where the amount (μg) of curcumin released per day (y-axis) from each biocompatible polymeric matrix is plotted against a release period measured in days (x-axis).
Figure 9B:
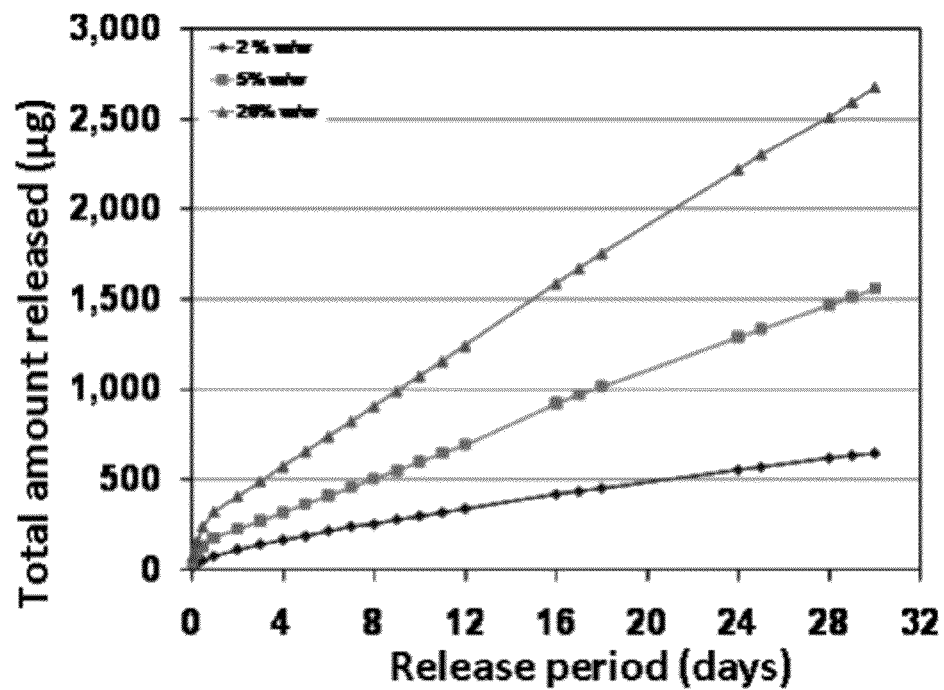
FIG. 9B is a graph depicting the cumulative release of curcumin from each biocompatible polymeric matrix where the total amount (μg) of curcumin released from each matrix (y-axis) is plotted against a release period measured in days (x-axis).

As shown in FIG. 9, the amount of curcumin released from the composition per day (FIG. 9A) and the total amount of curcumin released from the composition (FIG. 9B) varied proportionally with the amount of curcumin incorporated into each biocompatible polymeric matrix. Similar to the results described in Example 2, a greater amount of curcumin was released during the first week after placing the composition into the medium. Following the first week, however, amounts of curcumin released from each composition approached steady-state levels where a similar amount of phytochemical agent was released from each composition per day, indicating that increasing the amount of phytochemical agent that is incorporated into each matrix is an effective way to increase the bioavailability of the phytochemical agent without adversely effecting the release of the agent from the matrix.

Figure 10A:
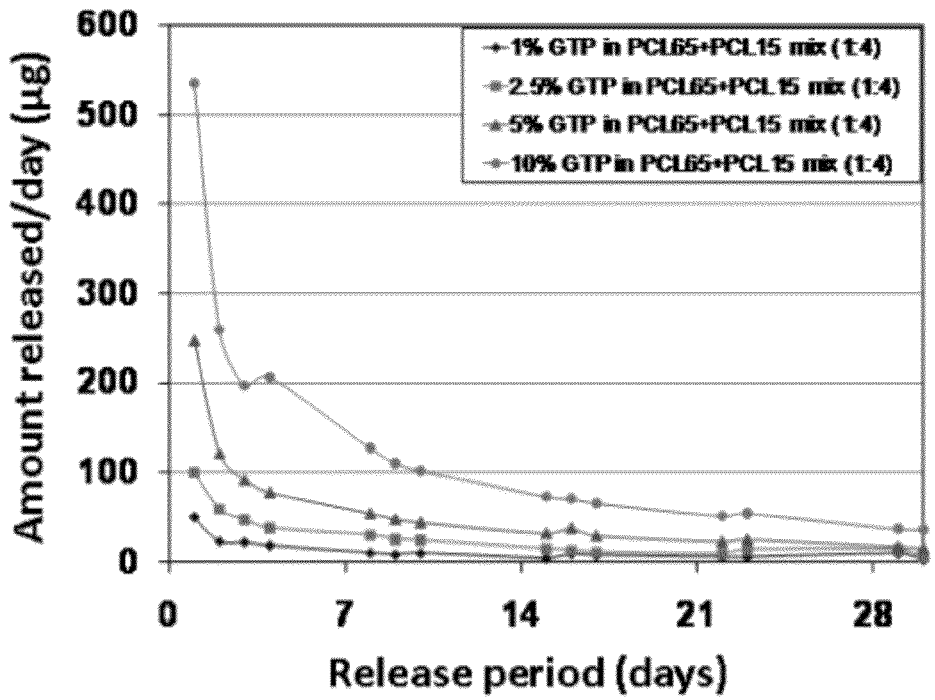
FIG. 10A is a graph depicting the daily release of GTPs from each of the biocompatible polymeric matrices where the amount (μg) of GTPs released per day (y-axis) from each biocompatible polymeric matrix is plotted against a release period measured in days (x-axis).
Figure 10B:
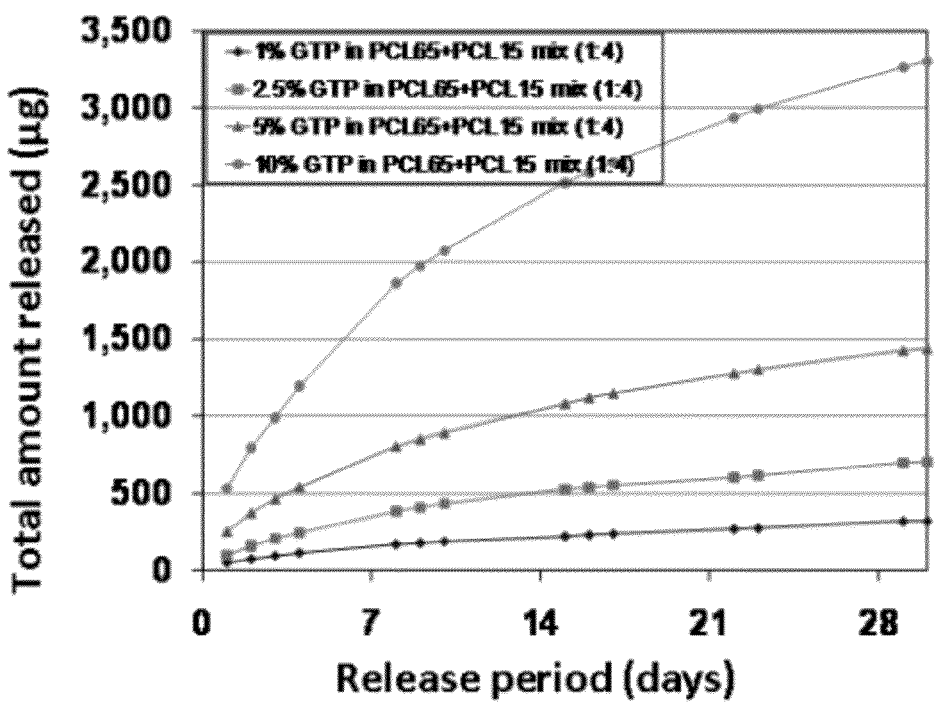
FIG. 10B is a graph depicting the cumulative release of GTPs from each biocompatible polymeric matrix where the total amount (μg) of GTPs released from each matrix (y-axis) is plotted against a release period measured in days (x-axis).

A similar experiment was also performed to examine the effect of incorporating various amounts of GTPs into a biocompatible polymeric matrix on the in vitro release of the agents. Briefly, 1% w/w, 2.5% w/w, 5% w/w, and 10% w/w GTPs were incorporated into a biocompatible polymeric matrix, comprised of polycaprolactone, MW 65K and polycaprolactone, MW 15K combined in a 1:4 ratio, and placed in a release medium (phosphate-buffered-saline (pH 7.4) containing 10% bovine serum) at 37° C. with constant agitation in a water bath. As shown in FIG. 10, the amount of GTPs released from the composition per day (FIG. 10A) and the total amount of GTPs released from the composition (FIG. 10B) varied proportionally with the amount of GTPs incorporated into each biocompatible polymeric matrix, again indicating that the amount of phytochemical agent incorporated into each matrix is an effective way to increase the bioavailability of the phytochemical agent without adversely effecting the release of the agent from the matrix.

Example 4

Short Term In Vivo Release of Curcumin from a Biocompatible Polymeric Matrix

Figure 11:
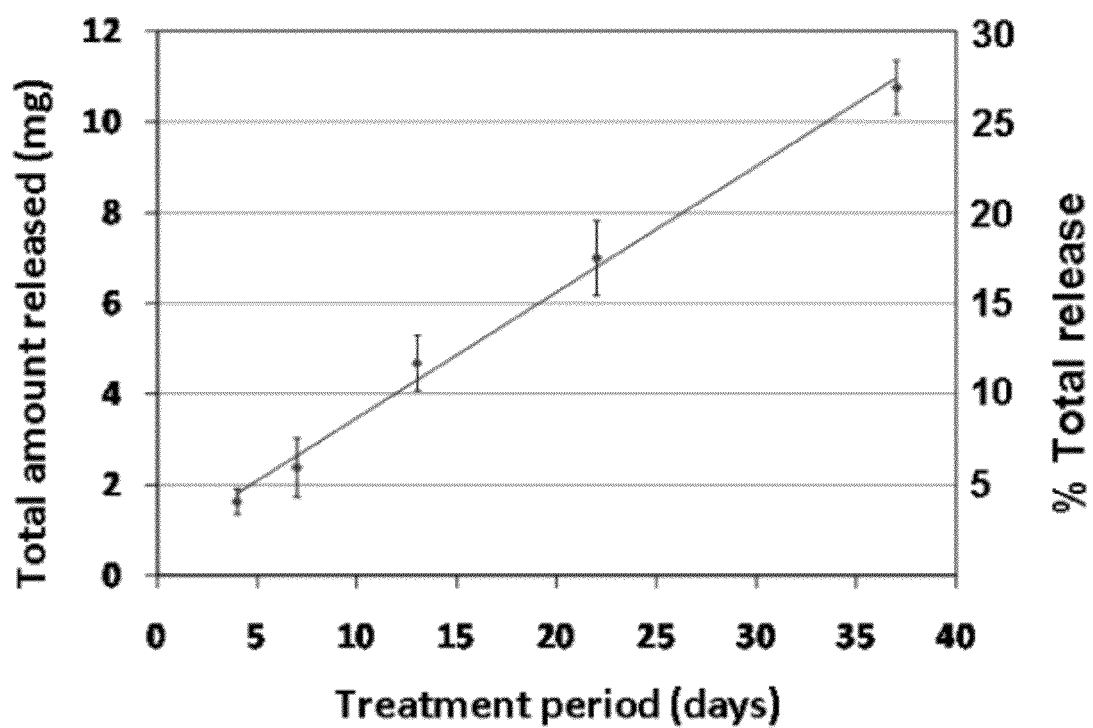
FIG. 11 is a graph depicting the short-term in vivo release of curcumin from a biocompatible polymeric matrix where the total amount (mg) of curcumin released (y-axis) and the total percentage of curcumin released (y-axis) from the matrix are plotted against a release period measured in days (x-axis).

To measure the average daily release of a phytochemical in vivo over a short time period in whole animals, two 2-cm biocompatible polymeric matrices incorporating 20% w/w of curcumin were implanted subcutaneously in the back of Sprague-Dawley rats. At predetermined time intervals, the animals were euthanized and the compositions were removed from the animals. The residual curcumin remaining in each matrix was then measured by solvent extraction and spectrophotometry. The total amount released at each time interval was determined by subtracting the unreleased amount of curcumin remaining in the matrix from the initial amount implanted into the rats, and this amount was divided by the initial amount implanted into the rats to determine the total percentage of curcumin released from the matrix at each time interval. As shown in FIG. 11, the total amount of curcumin (mg) released from the matrix and the total percentage of curcumin released from the matrix over the 40 day treatment period increased at each time interval indicating that a phytochemical agent can be effectively released from a biocompatible polymeric matrix in vivo and that this release is similar to the release kinetics observed for a phytochemical agent in vitro.

Figure 12A:
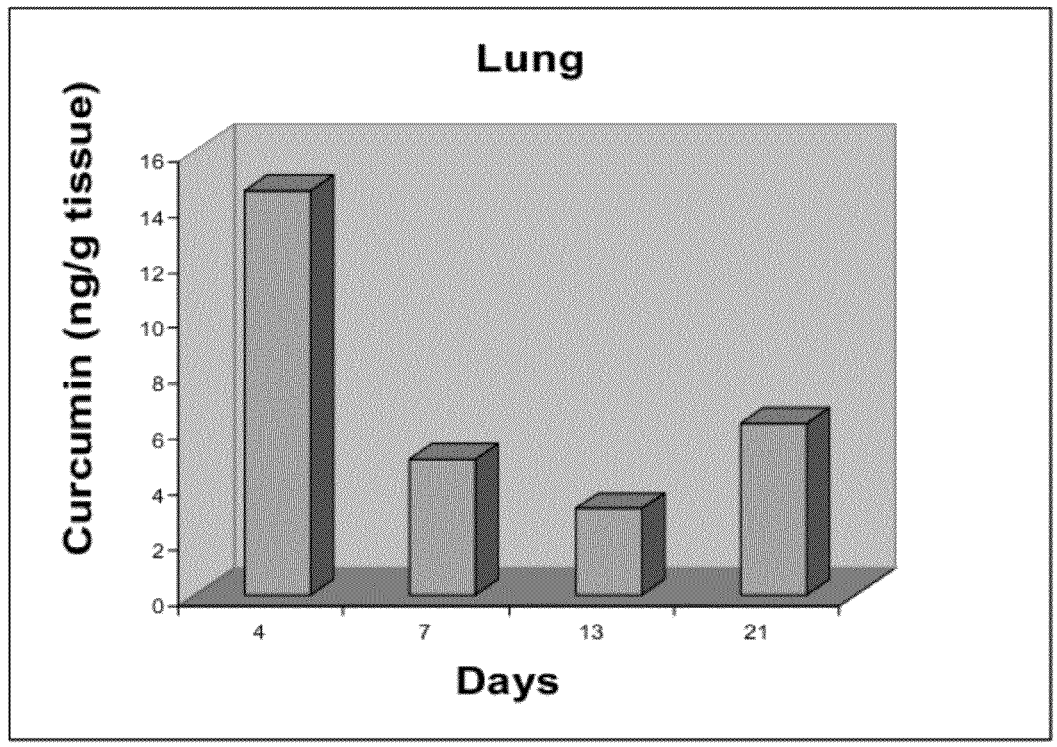
FIG. 12 includes graphs depicting the levels of curcumin (ng/g) in lung tissue (FIG. 12A) and liver tissue (FIG. 12B) of rats (y-axis) at different time intervals (x-axis), where the rats were treated with a composition comprising a biocompatible matrix incorporating 20% w/w curcumin.
Figure 12B:
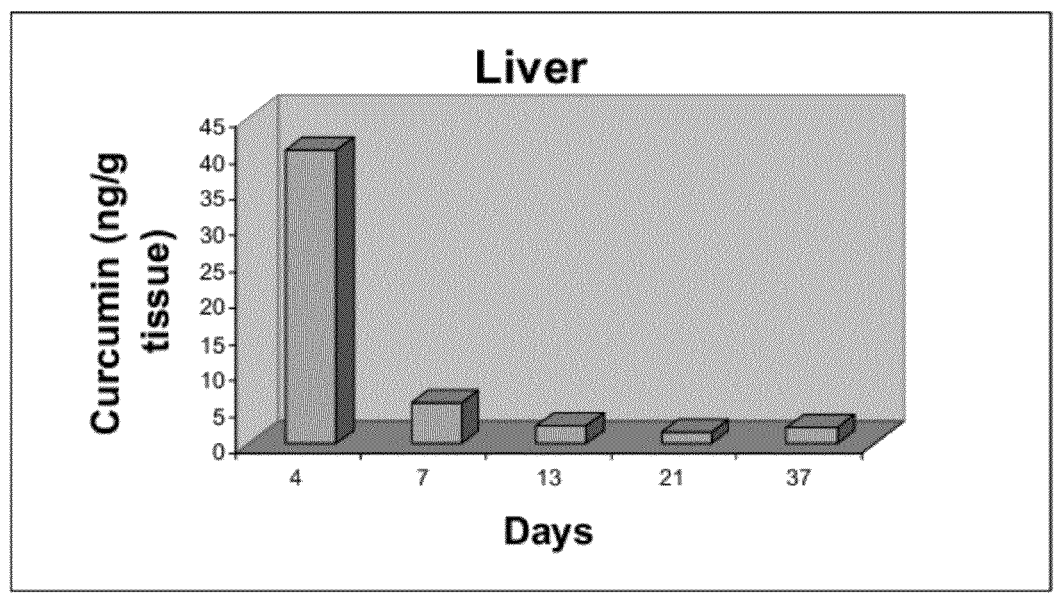
Figure 13A:
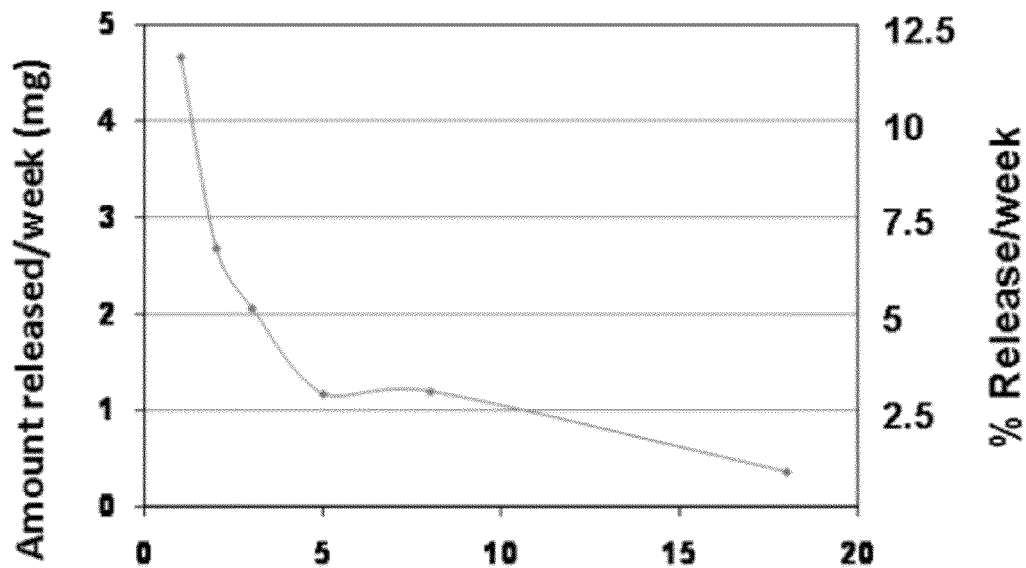
FIG. 13A is a graph depicting the daily release of curcumin from a biocompatible polymeric matrix where the total amount (mg) of curcumin released per week (y-axis) and the total percentage of curcumin released per week (y-axis) from the matrix are plotted against a treatment period measured in weeks (x-axis).
Figure 13B:
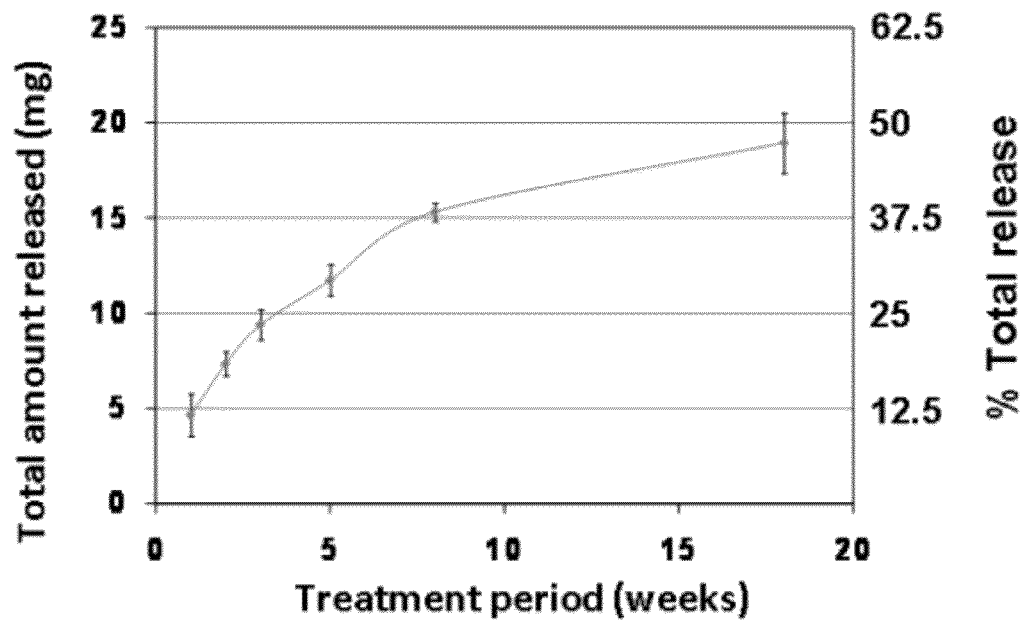
FIG. 13B is a graph depicting the cumulative release of curcumin from a biocompatible polymeric matrix where the total amount (mg) of curcumin released (y-axis) and the total percentage of curcumin released (y-axis) are plotted against a treatment period measured in weeks (x-axis).
Figure 14A:
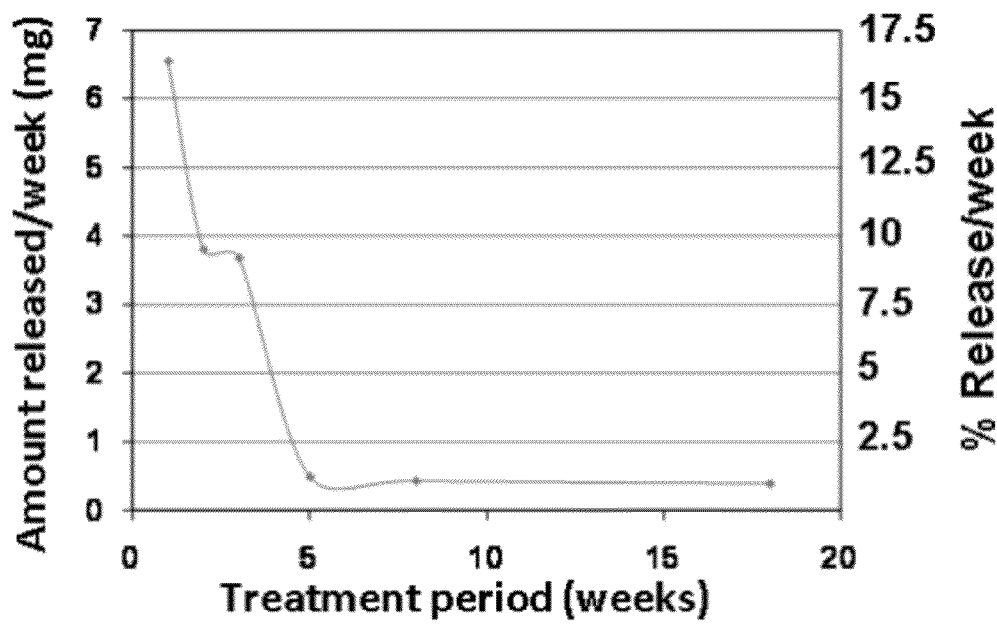
FIG. 14A is a graph depicting the daily release of GTPs from a biocompatible polymeric matrix where the total amount (mg) of GTPs released per week (y-axis) and the total percentage of GTPs released per week (y-axis) from the matrix are plotted against a treatment period measured in weeks (x-axis).
Figure 14B:
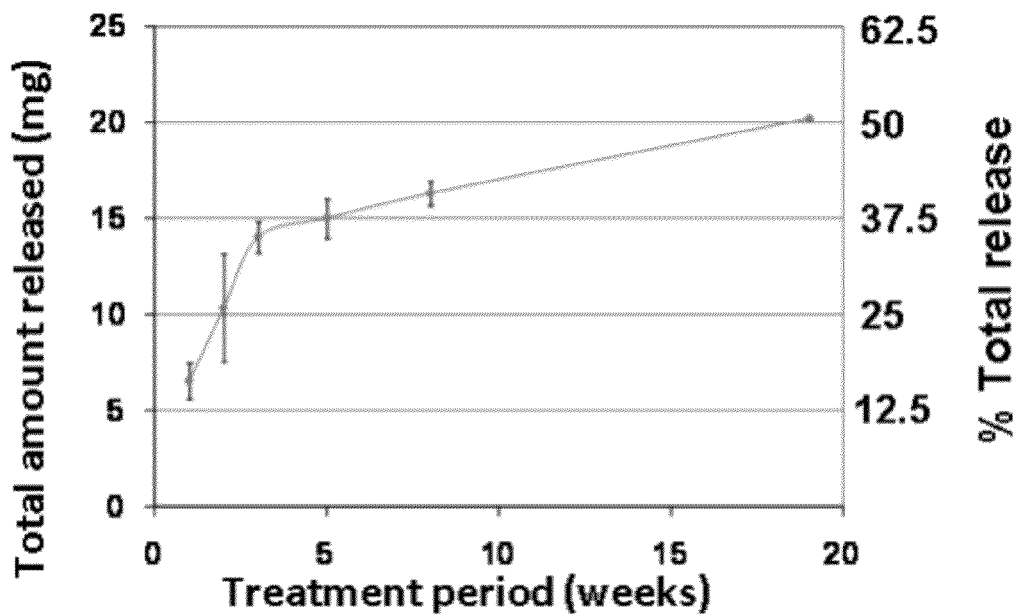
FIG. 14B is a graph depicting the cumulative release of GTPs from a biocompatible polymeric matrix where the total amount (mg) of GTPs released (y-axis) and the total percentage of GTPs released (y-axis) are plotted against a treatment period measured in weeks (x-axis).
Figure 15A:
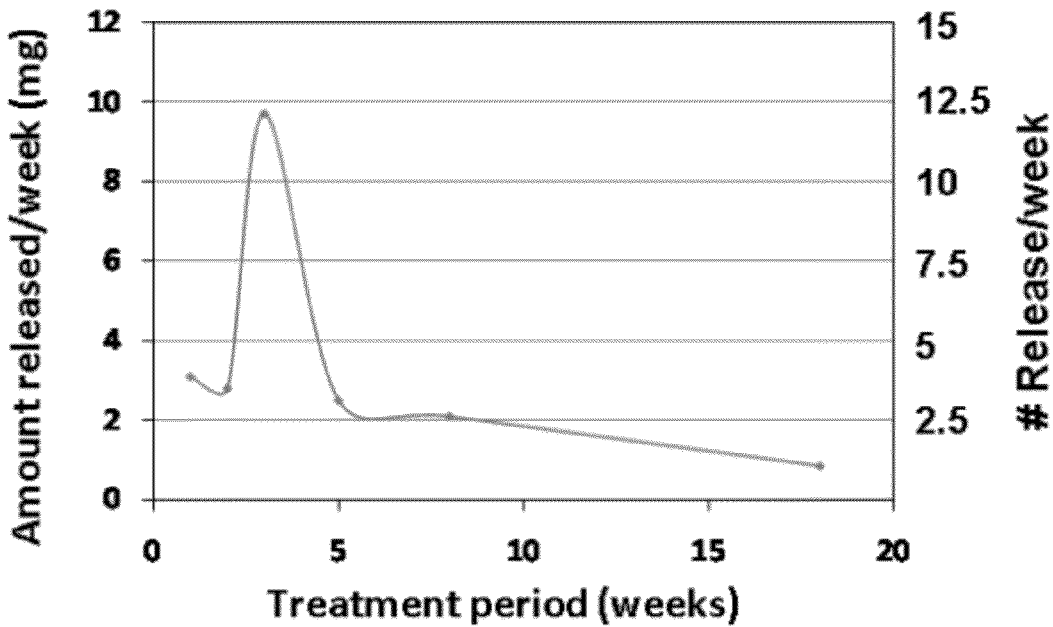
FIG. 15A is a graph depicting the daily release of DIM from a biocompatible polymeric matrix where the total amount (mg) of DIM released per week (y-axis) and the total percentage of DIM released per week (y-axis) from the matrix are plotted against a treatment period measured in weeks (x-axis). FIG.
Figure 15B:
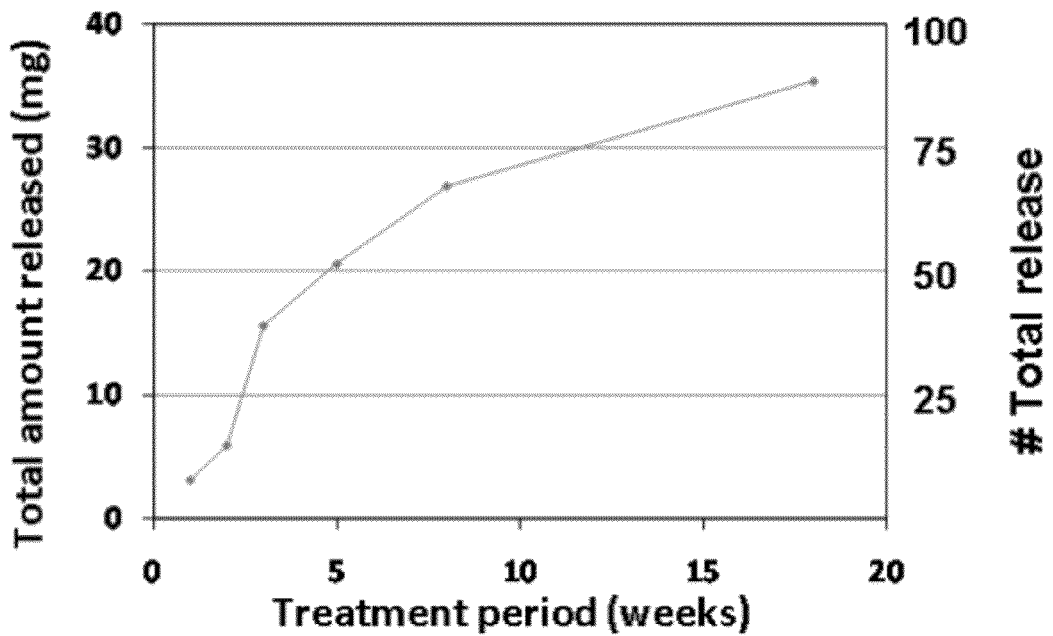
FIG. 15 includes graphs depicting the long-term in vivo release of DIM from a biocompatible polymeric matrix.

To determine the levels of curcumin released systemically into the rats treated with a biocompatible polymeric matrix incorporating 20% w/w curcumin, lung and liver tissues from each rat were removed after euthanizing the animals at 4, 7, 13, and 21 days after subcutaneous implantation of the compositions. Curcumin levels were measured in 0.5 g of tissue, either pooled from three rats randomly (lung) or analyzed from individual rats (liver), by solvent extraction and high-performance liquid chromatography (HPLC) in conjunction with a fluorescence detector and were expressed as nanograms (ng) of curcumin per gram (g) of tissue. As shown in FIG. 12A, curcumin was present at 4 days in lung tissue of treated rats at levels of approximately 15 ng/g. However, after 7 days these levels dropped to approximately 5 ng/g and this lower level of curcumin was maintained in the lung tissue at 13 days and 21 days post-implantation with only slight variation, indicating that a controlled low dose of curcumin can be sustained in tissue of subjects administered a biocompatible polymeric matrix incorporating a phytochemical agent by subcutaneous implantation. Similarly, in the liver tissue (FIG. 12B), curcumin was present at a level of approximately 40 ng/g at 4 days. The levels of curcumin in liver tissue dropped to about 5 ng/g at 7 days and then the levels remained constant at about 2.5 ng/g during the next 30 days.

Example 5

Long Term In Vivo Release of Phytochemicals from a Biocompatible Polymeric Matrix To measure the release of a phytochemical agent from a biocompatible polymeric matrix in vivo over an extended time period, four 2-cm implants, one each of curcumin (20% w/w), GTPs (20% w/w), DIM (20% w/w), and punicalagins (20% w/w) were implanted simultaneously into the back of female ACI rats. At predetermined time intervals, the animals were euthanized and the compositions were removed from the animals. The residual phytochemicals remaining in each matrix were then measured by solvent extraction and spectrophotometry. The total amount released at each time interval was determined by subtracting the unreleased amount of the phytochemical remaining in each matrix from the initial amount implanted into the rats, and this amount was divided by the initial amount implanted into the rats to determine the total percentage of the phytochemical released from the matrix at each time interval.

FIGS. 13 to 16 show the amount of exemplary phytochemical agents released per day and the total amount of phytochemical agents released from a biocompatible polymeric matrix of the presently-disclosed subject matter in vivo over an extended time period of 18 weeks, including data for the long-term release of curcumin (FIGS. 13A and 13B), GTPs (FIGS. 14A and 14B), diindolylmethane (DIM, FIGS. 15A and 15B), and punicalagins (FIGS. 16A and 16B). As shown in FIGS. 13 to 16, a greater amount of each phytochemical was initially released from the biocompatible polymeric matrix in the first few weeks following implantation. However, after approximately five weeks post-implantation, the phytochemical agents were released at consistently lower levels indicating that a controlled low dose of the phytochemical agents can be sustainably released from a biocompatible polymeric matrix incorporating a phytochemical reagent following subcutaneous implantation of the compositions. This greater initial release of the phytochemical agent, followed by a sustained lower release, is consistent with the in vitro data depicted in FIGS. 2 to 5.

Example 6

Effect of Chemotherapeutic Compositions on Inhibition of Tissue DNA Adducts Treated with a Single Bolus Dose of a Carcinogen Intervention with phytochemical agents is a useful strategy to inhibit or reduce cancer development. However, phytochemical agents must generally be administered in the diet at high doses in order to achieve effective plasma concentration and increased bioavailability. To reduce the effective dose of phytochemical agents compared to a dietary route, increase the bioavailability and minimize the toxicity of these phytochemical agents, the ability of a biocompatible matrix incorporating a phytochemical agent to inhibit the formation of DNA adducts after a single bolus dose of a carcinogen was determined. Briefly, female Sprague-Dawley rats were pretreated with curcumin either by diet (400 ppm, w/w) or by subcutaneous implantation of a 1 cm polycaprolactone (PCL) biocompatible polymeric matrix incorporating 20 mg of curcumin. Two weeks later, animals were challenged with a single intraperitoneal injection of benzo[a]pyrene (B[a]P) (50 mg/kg in dimethyl sulfoxide). The animals were then euthanized at predetermined time intervals, and liver and lung tissue samples were collected and analyzed for the formation of DNA adducts (FIG. 17). Analysis of the lung and liver DNA adducts by $^{32}$P-postlabeling (Gupta R C, 1996) showed that dietary curcumin inhibited the B[a]P-induced DNA adducts by 45% and 83% in the lung and liver (65±53 and 74±110 adducts/$10^9$ nucleotides), respectively compared with sham treatment (117±35 and 432±118 adducts/$10^9$ nucleotides). The adduct inhibition also occurred in animals that received curcumin via a biocompatible polymeric matrix, except that the degree of inhibition was 1.6 to 1.7 fold (17% and 48%, respectively) lower than the dietary administration. The total amount of curcumin administered via the polymeric matrix (less than 2 mg) was substantially lower than the amount administered by diet (about 120 mg), indicating a reduction of about 60-fold.

The lesser effectiveness of the curcumin administered via the biocompatible polymeric matrix was believed to stem from the low dose of curcumin, delivered by the implant, (approximately 80 µg/rat/day) that was available to combat against the bolus dose of B[a]P. To test this hypothesis, animals pretreated with curcumin implants for two weeks were further treated with a sustained, low dose of B[a]P incorporated into a polycaprolactone biocompatible polymeric matrix (1 cm incorporating 10 mg B[a]P). Analysis of tissue DNA adducts by $^{32}$P-postlabeling 30 days post B[a]P treatment showed 65% and 83% inhibition of adducts in the lung and liver (9±5 and 4±0.7 adducts/$10^9$ nucleotides), respectively compared with sham treatment (26±5 and 23±12 adducts/$10^9$ nucleotides). The average dose of curcumin over the duration of the study was approximately 110 µg/rat/day based on the amount left in the implants recovered from animals.

To determine the ability of further phytochemical agents incorporated into a biocompatible matrix to inhibit the formation of DNA adducts after a single bolus dose of a carcinogen, similar experiments were performed with biocompatible matrices incorporating either oltipraz or GTPs. Briefly, 10% w/w of oltipraz or GTPs was incorporated into a 2 cm polycaprolactone (MW 65K): cyclodextrin (combined in a 9:1 ratio) biocompatible polymeric matrix and subcutaneously implanted into female Sprague-Dawley rats. Eleven days later, the animals were treated with a bolus dose of dibenzo [a,1]pyrene. The animals were then euthanized 5 days after the carcinogen treatment and liver samples were collected. Analysis of DNA adducts in the liver of these rats by $^{32}$P-postlabeling revealed that treatment with both oltipraz (FIG. 18) and GTPs (FIG. 19) reduced the amount of B[a]P-induced DNA adducts when these phytochemicals were administered via their incorporation into a biocompatible polymeric implant.

Example 7

Effect of Chemotherapeutic Compositions on Inhibition of Tissue DNA Adducts in Subjects Treated with a Sustained Low Dose of a Carcinogen Unlike bolus dose animal studies, humans are generally exposed to steady, low doses of carcinogens via the diet, smoking, occupation, etc. To determine the ability of the presently-disclosed compositions to inhibit tissue DNA adducts in subjects treated with sustained low carcinogen doses, biocompatible polymeric matrices comprised of polycaprolactone and incorporating benzo[a]pyrene (B[a]P) were first prepared by dissolving both B[a]P and polycaprolactone in an appropriate solvent, melting the polymer following removal of the solvent, and extruding the molten material through a mold.

To compare the effect of a bolus dose versus sustained low doses, female Sprague-Dawley rats were then treated with B[a]P either by a single intraperitoneal injection (10 mg in 500 µl sunflower oil) or by a subcutaneous PCL implant (1 cm containing 10 mg B[a]P). One group received sham treatment. Animals were euthanized after 6, 15, and 30 days, and different tissues were collected. Analysis of lung, liver and mammary DNA by $^{32}$P-postlabeling showed two distinct adducts. Total DNA adduction (in adducts/$10^9$ nucleotides) in the lung, liver and mammary tissues by bolus-dose regimen occurred after 6 days (117±35, 432±118, and 104±5, respectively), followed by a gradual decline after 15 days (88±13, 279±36 and 50±15, respectively) and 30 days (60±10, 156±28 and 53±8 respectively). In contrast, the B[a]P—PCL implant resulted initially in low adduct level in the lung (13±3) but the levels increased progressively after 15 days (23±12) and 30 days (26±5), indicating that animals were exposed to B[a]P continuously. Adducts were also detected in the liver (11±2, 21±6 and 23±4, respectively) and mammary tissue (16±2, 18±5, 23±5, respectively) and increased steadily with time. Measurement of the residual B[a]P in implants recovered from the animals showed that <1 mg of total B[a]P was released over 30 days. This release was consistent with an average daily release of 26±9 µg B[a]P when implants were stirred at 37° C. in phosphate-buffered-saline, pH 7.4 containing 10% serum. Notably, the sustained, low-doses of B[a]P resulted in a similar degree of DNA adduct accumulation in all of the three tissues analyzed as compared with the bolus-dose, which resulted in higher adduct accumulation in the liver. This data shows that the polymer-based delivery system is an effective means to study sustained, low-dose carcinogenesis.

Following the establishment of the presently-disclosed compositions as an effective means to study sustained, low-dose carcinogenesis, the ability of the presently-disclosed compositions to inhibit tissue DNA adducts in subjects treated with sustained low carcinogen doses was determined by examining the effect of curcumin administered via a biocompatible polymeric matrix on the inhibition of tissue DNA adduct formation induced by a sustained low dose of B[a]P. Briefly, one group of Sprague-Dawley rats received a 1 cm biocompatible polymeric matrix incorporating 20% w/w of curcumin, while a second group of rats received a sham biocompatible polymeric matrix that did not incorporate an agent. Both groups were maintained on a control diet. Two weeks later, the two groups of animals received a 1 cm biocompatible polymeric matrix incorporating B[a]P (10% carcinogen load) subcutaneously. The animals were then euthanized after 30 days and tissue DNA adducts were analyzed by a $^{32}$P-postlabeling assay. Analysis of DNA adducts in liver and lung tissue showed that curcumin administered via a biocompatible polymeric matrix inhibited the B[a]P-induced DNA adducts in both the liver and lung, as compared with the animals receiving a sham implant (FIG. 20).

A similar experiment was performed to determine the ability of GTPs administered via a biocompatible polymeric matrix to inhibit tissue DNA adducts in subjects treated with sustained low carcinogen doses. Briefly, one group of Sprague-Dawley rats subcutaneously received two 2-cm biocompatible polymeric matrices incorporating 10% w/w of GTPs, while a second group of rats received a sham biocompatible polymeric matrix that did not incorporate a phytochemical agent. At the same time the animals were receiving the biocompatible polymeric matrices incorporating GTPs, both groups of animals also received a 1 cm biocompatible polymeric matrix incorporating B[a]P (10% carcinogen load) subcutaneously. The animals were then euthanized 6 days after implantation of the matrices and tissue DNA adducts were analyzed by a $^{32}$P-postlabeling assay. Similar to the experiments described above with curcumin, analysis of DNA adducts in liver tissue of these animals showed that GTPs administered via a biocompatible polymeric matrix inhibited the formation of B[a]P-induced DNA adducts, as compared with the animals receiving a sham implant (FIG. 21).

Example 8

Effect of Green Tea Polyphenols on Cytochrome P450 Expression

Cytochrome P450 proteins are a diverse family of hemoproteins and are widely regarded as an important enzyme in the metabolism and formation of carcinogens. To determine the effect of GTPs administered via subcutaneous implantation of a biocompatible polymeric matrix incorporating the GTPs on cytochrome P450 1A1 and 1B1 mRNA expression, liver tissue was collected from Sprague-Dawley rats that subcutaneously received a 1 cm biocompatible polymeric matrix incorporating B[a]P (10% carcinogen load) and either a 1 cm biocompatible polymeric matrix incorporating 10% w/w of GTPs or a sham biocompatible polymeric matrix that did not incorporate a phytochemical agent, as described in Example 7. Analysis of the fold change in mRNA expression revealed that CYP 1A1 expression was not significantly affected by the administration of GTPs via a biocompatible polymeric matrix (FIG. 22A), but revealed that CYP 1B1 expression was reduced by the administration of the GTPs (FIG. 22B). Taken together, these results indicate that by reducing cytochrome P450 mRNA levels, the administration of a biocompatible polymeric matrix incorporating an effective amount of a phytochemical agent can be an effective means to lower the production of DNA-reactive metabolites of B[a]P and thus lower DNA adduct levels.

Example 9

Effect of Individual Phytochemical Agents on Mammary Carcinogenesis

Cancer chemoprevention approaches have been used to manipulate tumorigenesis and reduce the transformation of normal/pre-cancerous cells to malignancy. Many compounds that have worked in cell culture studies though have failed in animal models and clinical trials due to lack of bioavailability. Additionally, the high doses required to elicit biological response can be toxic. The following experiments were designed to test the hypothesis that the effective dose of phytochemical agents, administered systemically via implantation of a silastic implant incorporating the agents, can be reduced substantially compared with the traditional dietary route and were also designed to determine the effect of individual phytochemical agents on mammary carcinogenesis. The silastic implants used in the experiments described below were fabricated by filling silastic tubing with a desired agent. Although the silastic implants are not biodegradable like compositions disclosed herein comprising biocompatible polymeric matrices, the silastic implants provide proof of concept that a reduced dose of phytochemical agents administered systemically can be effective in inhibiting mammary carcinogenesis.

Initially, an experiment was performed by subcutaneously implanting individual phytochemical agents using a large number of animals per group (n=17-19). Briefly, four groups of ACI rats received either a biocompatible silastic implant with no phytochemical agent or a 3 cm biocompatible silastic implant incorporating either ellagic acid, lycopene, or curcumin (27 mg phytochemical agent per implant). Two weeks later, all groups received 3 cm biocompatible silastic implants incorporating 27 mg of 17β-estradiol. Six months later, after all animals had developed mammary tumors, the animals were euthanized and the mammary tumors were counted and their size measured. Tumor incidence or multiplicity, as measured by the number of mammary tumors, was not significantly reduced by any of the phytochemical agents (FIG. 23B). However, 30-55% reductions were found in the tumor burden with all test agents (FIG. 23A) as measured by tumor volume, with ellagic acid resulting in the most significant reduction in tumor burden (55%). The foregoing results thus support the effectiveness of ellagic acid, a significant component in certain berries, as an exemplary phytochemical compound that can be administered via a biocompatible silastic implant to inhibit or reduce estrogen-induced ACI rat mammary carcinogenicity.

To further evaluate the effectiveness of ellagic acid in estrogen-induced mammary carcinogenicity and to determine whether the effective dose of ellagic acid administered systemically via a biocompatible silastic implant can be reduced substantially compared with the traditional dietary route, ellagic acid was administered either in the diet (400 ppm) or by subcutaneous implantation of a biocompatible silastic implant incorporating an effective amount of ellagic acid (27 mg/implant, 4 implants). Two weeks later, all animals were treated with 17β-estradiol (9 mg) by a subcutaneous implantation of a biocompatible silastic implant incorporating the 17β-estradiol. All groups received diet and water ad libitum. The body weight and diet consumption were recorded weekly. The animals were palpated for mammary tumors, and were euthanized when the largest tumor reached >1 cm. The first tumor in the control group appeared after nearly 84 days. However, the first tumor appearance with ellagic acid implants or ellagic acid-supplemented diet was somewhat delayed by 2 and 3 weeks, respectively. The control group reached 100% tumor incidence after 26 wks, but only 75% or 69% of the animals developed palpable tumors in the groups that received ellagic acid by implants or diet, respectively. Ellagic acid also reduced the tumor burden (FIG. 24B) with both the implant (slow release, 454±105 mm$^3$) and dietary (269±61 mm$^3$) routes, as compared with the control group (787±170 mm$^3$). Similar reductions were also observed in the tumor multiplicity (4.00±0.63 and 4.80±0.4 tumors/rat with implant and diet, respectively versus 6.77±0.87 in the control group) (FIG. 24A).

The total amount of ellagic acid administered during the entire duration of the study by diet was 800 mg/rat while the subcutaneous implantation of the biocompatible silastic implant incorporating ellagic acid delivered only 1.48±0.87 mg per implant, as determined by HPLC measurement of the material left in implants recovered after termination. Thus, with 4 implants per animal, an approximately 135-fold reduction of the ellagic acid dose produced similar biological responses when delivered by the slow release system. This approach thus opens new avenues for phytochemical agents whose use has been discontinued for therapeutic purposes, either due to lack of bioavailability or toxicity due to high doses.

To further determine the effects of phytochemical agents on mammary cell proliferation, an additional in vivo experiment was performed. Briefly, six week-old female ACI rats were divided in five groups (six per group). Animals received either purified (AIN-93M) control diet (Groups A-C) or diet supplemented with 2.5% cumin (Group D) or 2.5% fennel (Group E). Group C received implants of aqueous and non-aqueous extracts of fennel. The extracts were prepared from 1 g each of fennel. Concentrated aqueous and non-aqueous extracts were incorporated respectively in two 3-cm biocompatible silastic implants, and, thus, each animal received four implants, equivalent to 2 g fennel. Ten days later, all but Group A received a 1.2 cm implant of 17β-estradiol (9 mg) incorporated into a biocompatible silastic implant; Group A received sham implants. Experimental diets were continued until termination of the experiment. Diet and water were provided ad libitum. Animals were weighed and diet consumption recorded frequently. All animals were euthanized 20 days after estrogen treatment, blood and mammary and other organs were collected, and the tissues were weighed.

The sham-treated rat mammary tissues showed normal morphology. All rats treated with estrogen showed mild to moderate marked lobular hyperplasia with occasional dilate ducts filled with secretions. However, groups receiving intervention were less cellular than control group. Slides stained for Proliferating Cell Nuclear Antigen (PCNA) and Ki-67, cellular markers of proliferation, were scored by two experienced cytotechnologists to account for inter-observer variability and averages of the two were considered in interpretation of the data.

Analysis of PCNA staining in mammary tissues from rats without estrogen treatment showed essentially the same percentage of cells with moderate staining (41%) as with estrogen treatment, with (37-41%) or without (38%) phytochemical intervention. However, as shown in FIG. 25, the percentage of cells with intense staining for PCNA increased significantly with estrogen treatment, from 8% to 27%. This increase was significantly offset by intervention with the phytochemicals, with the percentage of cells with intense staining being decreased by 22% with dietary cumin (p=0.28), 40% (p=0.03) with dietary fennel, and 43% (p=0.005) with fennel extract implants. This conclusion was seconded by analysis of Ki-67, another marker for cell proliferation. These data show cumin and fennel phytochemicals have anti-proliferative activity and demonstrates that these phytochemicals administered by a slow-release system elicited the same efficacy as dietary route.

Example 10

Inhibition of Mammary Cell Carcinogenesis by Combined Administration of Phytochemical Agents To determine the effect of utilizing a combination of phytochemical agents in inhibiting mammary cell carcinogenesis, female ACI rats were divided into Groups A-C (8 animals/group). Group A subcutaneously received sham implants (e.g., biocompatible silastic implants without a phytochemical agent) while groups B and C received implants of 3 cm biocompatible silastic implants incorporating various phytochemical agents. Group B received one implant each of oltipraz and curcumin, and Group C received one implant each of curcumin, ellagic acid, co-enzyme-Q10, and lycopene. Two weeks later, all groups received implants of 17β-estradiol implants comprised of a biocompatible silastic implant incorporating the 17β-estradiol. Animals received standard rodent chow diet and water ad libitum. Six months later, animals were euthanized and mammary tumors were counted and their sizes were measured with a caliper. Comparison of the groups showed no difference in the tumor incidence, but the tumor multiplicity (FIG. 26B) in the groups receiving phytochemical agents, Group B (3.4±1.3; p=0.01) and Group C (6.3±3.8; p=0.34), was lower as compared with the control group, Group A (8.25±3.4). The tumor volume (in $mm^3$/rat) was also reduced by both the combination of phytochemical agents (FIG. 26A), from 2,283±2,061 (Group A) to 447±429 (p=0.08) (Group B) and 124±76 (p=0.03) (Group C). Although the reductions in tumor burden in Group B and tumor multiplicity in Group C were insignificant, presumably due to the small sample size, the data indicate that the slow-release composition is effective in eliciting a biological response and in inhibiting mammary cell carcinogenesis.

Example 11

Inhibition of Mammary Cell Proliferation by Combined Administration of Phytochemical Agents To determine the effect of administering a combination of phytochemical agents in inhibiting mammary cell proliferation, four 2-cm biocompatible polymeric matrices, one each incorporating curcumin (20% w/w), GTPs (20% w/w), DIM (20% w/w), and punicalagin (20% w/w) were implanted subcutaneously in the back of female ACI rats. Two weeks later, the animals received either an empty biocompatible polymeric matrix or a biocompatible polymeric matrix incorporating 17β-estradiol (9 mg/1.2 cm implant).

Three weeks later, animals were euthanized and mammary cell proliferation was measured by immunohistochemistry by staining for the cell proliferation marker PCNA. As shown in FIG. 27, analysis of the results showed that at three weeks post-implantation, the estrogen-treated animals that were administered the combination of phytochemical agents exhibited a significantly lower percentage of PCNA-positive cells, as compared to the estrogen treated animals that were not administered a phytochemical agent. These data thus indicate that a combination of phytochemical agents administered via the polymeric matrix is highly effective in inhibiting mammary cell proliferation.

Example 12

Synergistic Activity of Phytochemical Agents in Treating Lung Cancer

Increased cellular proliferation is an integral part of the cancer phenotype and agents that have the potential to slow the growth of these phenotypes are often considered prophylactic (Dorai T & Aggarwal B B, 2004). To determine whether phytochemical agents administered in combination would display synergistic activity as compared with phytochemical agents administered individually, human lung cancer cells (H1299) were incubated with vehicle only, with phytochemical agents individually, or with a combination of phytochemical agents. Following incubation for 1-3 days, the cells were incubated with 3-(4,5-dimethylthiazol-2-yl)-2,5-diphenyltetrazolium bromide (MTT). The resultant formazan product was solubilized in dimethyl sulfoxide and the absorbance was measured at 540 nm to determine the extent of cellular proliferation. As shown in FIG. 28, incubation of the H1299 cells with a mixture of delphinidin, petunidin, malvidin, peonidin, and cyanidin inhibited the growth of H1299 cells at a much lower concentration as compared to phytochemical agents administered individually. These data thus indicate that a combination of phytochemical agents can act synergistically in inhibiting the growth of lung cancer cells.

The effect of phytochemical agents on cell growth and proliferation can be explained by their ability to alter the expression of cell-cycle related proteins leading to the induction of cell cycle arrest and apoptosis Inhibition of cell proliferation and/or induction of apoptosis are highly correlated with the activation of a variety of intracellular signaling pathways leading to the arrest of the cell cycle in a particular phase (Yun J M, et al., 2009). To further examine the synergistic activity of combinations of phytochemical agents in treating lung cancer, H1299 cells were incubated for 48 hours with a vehicle (dimethyl sulfoxide) only, with individual phytochemical agents, or with a combination of phytochemical agents. Following harvesting of the cells, the cell pellet was washed with phosphate-buffered saline and fixed in 70% ethanol. To measure the percentage of cells undergoing apoptosis, the cells were then treated with RNase A and propridium iodide, and analyzed using a FACS-420 Flow Cytometry Analyzer. The treatment of cells with growth-suppressive concentrations of phytochemicals resulted in significant accumulation of cells in G2/M and G0/G1 phases of the cell cycle. An increase in the fraction of cells with sub-G0/G1 DNA content subsequent to the treatment of the cells with phytochemical agents was also observed in the analysis of cell cycle distribution and this sub-G0/G1 fraction was considered the apoptotic fraction. As shown in FIG. 29, incubation of the cells with a mixture of delphinidin, cyanidin, malvidin, peonidin, and petunidin, or a mixture of punicalagins and delphinidin resulted in a marked increase in the number of H1299 cells undergoing apoptosis, thus indicating that the a combination of phytochemical agents can act synergistically in inducing apoptosis in lung cancer cells.

Example 13

Formulation and Use of Device for Cervical Insertion

A device for cervical insertion (FIG. 30) was made of biodegradable polymers (polycaprolactone: F68 in a 4:1 ratio) incorporating a desired phytochemical agent (see, e.g., FIGS. 32A-32D showing perspective view of an exemplary device for cervical insertion comprising a biocompatible polymeric matrix incorporating curcumin). The device was capable of incorporating a phytochemical agent load of 0.5% to as much as 20% or more and was prepared by extruding a molten polymer formulation through a plastic mold made of a polypropylene transfer pipet, a round spoon and a 10-ml plastic syringe. The cut-piece of the pipet mold was narrow on one end and broad on the other end. The narrow part of this cut-pipet was attached to the syringe, while the broader part was held against the spoon to allow the molten material to pass through the pipet mold onto the spoon. Once the pipet mold was filled, the molten material started to collect in the spoon. The assembly was then detached from syringe and the material on the spoon was flattened manually to provide a round shape. After drying, a 3-5 mm hole was drilled lengthwise through the device. Following this fabrication protocol, the typical device weighed approximately 2.5 to 4 g, depending upon the size of the mold.

The device for cervical insertion is capable of delivering phytochemical agents to uterine cervix locally. As shown in FIGS. 33A and 33B, the device can be inserted into a cervix such that the shaft of the device engages the walls of the cervical canal and the bottom surface of the cap engages the external orifice of the uterus. As such, the device is capable of delivering an effective amount of a phytochemical agent locally to a cervix or the device can also be used to deliver phytochemical agents via systemic delivery to other organs like the uterus and ovary or to an organ more distant from the site of insertion such as the lungs.

An exemplary device for cervical insertion is relatively non-invasive and can include a tapered distal end to allow for easy insertion into a cervix as well as a canal through the device to allow for the passage of normal bodily fluids from the uterus. As shown in FIG. 31, an exemplary device for cervical insertion can be fabricated such that the cylindrical shaft is about 19 to about 25 mm in length and about 9 to about 11 mm in diameter, the cap is about 20 to about 25 mm in diameter, and the canal is about 4 mm to about 5 mm in diameter. Without wishing to be bound by any particular theory, it is believed that by fabricating the device in the foregoing dimensions, the device correlates to the dimensions of the human anatomy that it engages such that the device can engage the surrounding tissue and effectively deliver a phytochemical agent.

Example 14

In Vitro Release of Curcumin from an Exemplary Device for Cervical Insertion

To determine daily release of a phytochemical agent from a device for cervical insertion in vitro, a cervical insertion device comprising a biocompatible polymeric matrix incorporating curcumin was placed in a release medium (phosphate-buffered-saline (pH 7.4) containing 10% bovine serum) at 37° C. with constant agitation in a water bath to simulate an in vivo scenario. The medium was replaced daily and the amount of curcumin released from the compositions per day was measured spectrophotometrically against a standard curve and expressed as micrograms per day.

FIGS. 34A and 34B show the amount of curcumin released per day and the total amount of curcumin released from an exemplary device for cervical insertion over a release period of 18 days. This data, which is similar to the data described herein for the in vitro and in vivo release of phytochemical agents, shows that over the initial five days following the placement of the device into the release medium a greater amount of curcumin is released from the device. However, after approximately 5 days in the release medium, the amount of curcumin being released decreased and approached lower steady-state levels indicating that an exemplary device for cervical insertion can effectively be used to release a controlled low dose of a phytochemical agent over a time period.

Example 15

Efficacy of Compositions in Inhibiting Growth of Human Cancer Cells in a Nude Mouse Model To determine whether phytochemical agents inhibit tumor growth in a dose dependent manner and to determine whether the effective dose of the phytochemical agents is substantially lower than doses delivered by traditional oral administration, the ability of the presently-described compositions to inhibit growth of human lung, breast, and cervical cancer cells in a dose dependent manner is examined using a nude-mouse model. Briefly, nude mice are injected with 1-10 million tumor cells (lung, breast or cervical tumor cells) subcutaneously on the dorsal flank in 50-100 μl of PBS or growth media according to established protocols (Morton C L & Houghton P J, 2007). The mice also receive a 2 cm biocompatible polymeric matrix incorporating 2-20% (w/w) of a phytochemical agent as a subcutaneous implant. Tumors start appearing at the site of implantation after approximately 2-4 weeks. The tumor growth is then monitored twice a week and is measured using a digital caliper. Once the tumor has reached approximately 1.5 cm in diameter in the control group, all of the animals are euthanized and the tumor tissue is isolated for examination of biochemical and molecular parameters. Different phytochemical agents are examined for their antitumor efficacy and the efficacy of combinations of different phytochemical agents are also examined by administering the combinations as a single implant or in multiple implants. Analysis of tumor tissue also reveals the mechanism by which the phytochemical agents are able to exert their effects. As compared with animals receiving sham implants, a reduction in tumor volume is observed in mice receiving biocompatible polymeric implants incorporating an effective amount of a phytochemical agent, indicating that a composition and method that includes or makes use of a biocompatible polymeric matrix incorporating an effective amount of a phytochemical agent is useful for treating breast, lung, and cervical cancer.

16—Efficacy of Compositions Used in Combination with Chemotherapeutic Agents and Anti-Inflammatory Agents Phytochemical agents are often used in adjuvant therapy with conventional chemotherapeutic drugs to enhance their therapeutic efficacy and are recommended in adjuvant therapy with selective Cox-2 inhibitors (like celecoxib) for adenomatous polyposis. Selective Cox-2 inhibitors often leave other critical carcinogenic pathways unaltered, however, and phytochemicals can augment their activity by inhibiting such alternative pathways involved in carcinogenesis. Previous studies have found that silibinin sensitizes the hormone refractory DU145 prostate carcinoma cells to cisplatin and carboplatin-induced cell growth inhibition and apoptotic death, and can be combined to enhance the therapeutic efficacy of these compounds. Moreover, certain chemotherapeutics like paclitaxel induce expression of antiapoptotic (XIAP, IAP-1, IAP-2, Bcl-2, and Bcl-xL), proliferative (cyclooxygenase 2, c-Myc, and cyclin D1) and metastatic proteins (vascular endothelial growth factor, matrix metalloproteinase-9, and intercellular adhesion molecule-1) which can be inhibited by addition of phytochemical agents like curcumin. Additionally, certain agents like linalool moderately inhibit cell proliferation, but are known to exert synergistic effects with chemotherapeutics like doxorubicin by potentiating the cytotoxicity and proapoptotic effects of doxorubicin. Previous studies have shown that linalool increases doxorubicin accumulation and decrease Bcl-xL levels which results in its higher cytotoxicity for malignant cells. Phytochemical agents like licochalcone and licorice were also found to inhibit cisplatin induced hepatotoxicity and nephrotoxicity. In this regard, repeated oral administration of licochalcone prior to cisplatin has been found to exert a preventive effect by blunting the cisplatin induced increase in serum nitric oxide and tissue lipid peroxidation levels and be increasing the glutathione levels in the tissues. (Lee C K, et al., 2008).

To determine whether the presently-described biocompatible polymeric matrix can effectively be used in adjuvant therapy to administer a phytochemical agent with a chemotherapeutic agent and/or an anti-inflammatory agent, either in the same implant or in separate implants, and to mitigate the toxicity, increase the efficacy, or both of chemotherapeutic agents, a nude mouse model is utilized. Briefly, nude mice are injected with 1-10 million tumor cells (lung, breast or cervical tumor cells) subcutaneously on the dorsal flank in 50-100 μl of PBS or growth media according to established protocols (Morton C L & Houghton P J, 2007). When the tumors start appearing at the site of injection (approximately 2-4 weeks), the mice then receive a 2 cm biocompatible polymeric matrix incorporating 2-20% (w/w) of a phytochemical agent and a chemotherapeutic agent and/or anti-inflammatory agents as subcutaneous implant(s). The biocompatible polymeric matrix incorporating the chemotherapeutic agent and/or anti-inflammatory agents is prepared by the same method that is used to prepare the biocompatible polymeric matrices incorporating an effective amount of a phytochemical agent, which is described herein above in Example 1. The tumor growth is monitored twice a week and is measured using a digital caliper. The tumor is allowed to reach approximately 1.5 cm in diameter in the control group. At this point, all the animals are euthanized and the tumor tissue is isolated for the examination of biochemical and molecular parameters. Analysis of the results reveals that a lower dose of the chemotherapeutic agent is required to inhibit tumor growth when adjuvant therapy using natural phytochemical agent is used, indicating that a composition and method that includes or makes use of a biocompatible polymeric matrix incorporating an effective amount of a phytochemical agent and a chemotherapeutic agent is useful for treating lung, cervical, and breast cancer, and that by incorporating a chemotherapeutic agent in a biocompatible matrix a lower dose of the chemotherapeutic agent can be used to treat cancer. Furthermore, when an anti-inflammatory agent is also incorporated into a biocompatible polymeric matrix, and is administered in conjunction with a biocompatible polymeric matrix incorporating a phytochemical agent and a chemotherapeutic agent, a reduction in the local inflammatory reaction to the chemotherapeutic agent is observed, indicating that the inclusion of an anti-inflammatory agent is useful for overcoming any local inflammatory reaction to the chemotherapeutic agent.

Example 17

Efficacy of Chemotherapeutic Compositions in Inhibiting Growth of Chemically Induced Breast or Lung Tumors To determine whether breast and lung tumors induced by selected carcinogens can be inhibited in the host environment by the administration of a biocompatible polymeric implant incorporating an effective amount of a phytochemical agent, and to determine whether the requisite effective dose of the phytochemical agents can be lowered as compared with the traditional oral route, a rodent model is used.

To determine the effect of a biocompatible polymeric matrix incorporating a phytochemical agent on inhibiting chemically-induced lung tumors, female A/J mice (4-5 weeks old) receive either a sham implant or a biocompatible polymeric matrix implant incorporating 2-20% (w/w) of one or more phytochemical agents. Two weeks after receiving the implants, the mice receive 11.65 mg/kg body weight of 4-(methylnitrosamino)-1-(3-pyridyl)-1-butanone (NNK) by gavage three times a week for 10 weeks. Six mice are then euthanatized at 5-weeks after the first carcinogen treatment and 1-week after the last carcinogen treatment (11 weeks) for intermediate biomarker analysis. Six weeks after the last carcinogen treatment (16 weeks), all mice are euthanatized, lung tissue is removed, surface adenomas are counted, and tissue is serially sectioned to count internal tumors. Part of the lung is also snap frozen for biomarker analysis. A reduction in the tumor multiplicity, both on the surface of the lung and internally, and a reduction in the conversion of adenomas to carcinomas is observed in the group receiving a biocompatible polymeric matrix incorporating one or more phytochemical agents, indicating that the presently-disclosed compositions are useful for treating chemically-induced lung tumors.

To determine the effect of a biocompatible polymeric matrix incorporating a phytochemical agent on inhibiting chemically-induced breast tumors, a first group of female Sprague-Dawley rats are injected intra-peritoneally with 50 mg of 1-methyl-1-nitrosourea (MNU) per kg body weight at 21 days of age. The first palpable tumor, histologically classified as an adenocarcinoma, starts appearing around 30 days post-carcinogen administration and at the end of 35 days post MNU administration, the cumulative incidence of palpable carcinomas is around 60-90%. A second group of rats receives an estradiol implant (1.2 cm silastic implant containing 9 mg) that is implanted subcutaneously on the back of ACI rats at 8-9 weeks of age. In the group of rats receiving an estradiol implant, the first palpable tumor appears around 3-4 months and nearly 100% of the rats develop palpable mammary tumors by 8 months. In both of these models, one or more phytochemical agents are delivered via a biocompatible polymeric matrix two weeks before the chemical carcinogen treatment. The rats are monitored weekly for palpable tumors. As compared to control groups, postponement of the appearance of the first tumor by approximately 3 to 5 weeks, as well as a reduction in tumor multiplicity and burden by 50-80 percent, is observed in rats receiving a biocompatible polymeric matrix incorporating one or more phytochemical agents, indicating that a composition and method that includes or makes use of a biocompatible polymeric matrix incorporating an effective amount of a phytochemical agent is useful for inhibiting the growth of chemically-induced breast tumors.

Example 18

Analysis of Release Kinetics and Availability of Compounds as Compared to Oral Administration To further evaluate and compare the compositions of the presently-disclosed subject matter, which incorporate an effective amount of a phytochemical agent into a biocompatible polymeric matrix, studies where undertaken to assess tissue levels of curcumin achieved via the polymeric matrices as compared with the delivery of cucrumin via the traditional dietary route. The biochemical efficacy of curcumin to alter expression and/or activity of various hepatic xenobiotic-metabolizing enzymes was also determined and compared with the different delivery routes.

Briefly, to produce the biocompatible polymeric matrices incorporating curcumin, medical grade poly ($\epsilon$-caprolactone) 121,000 molecular weight (PCL-121) was purchased from SurModics Pharmaceuticals (Birmingham, Ala.), dichloromethane, acetonitrile, anhydrous citric acid and phosphate-buffered-saline (PBS) were from Sigma-Aldrich (St. Louis, Mo.), polyethylene glycol of 8000 molecular weight (PEG-8K) from Fisher Scientific (Fair Lawn, N.J.), ethanol from Pharmco-AAPER (Louisville, Ky.), bovine calf serum (BCS) from Hyclone (Logan, Utah) and silastic tubing (3.4 mm internal diameter) from Allied Biomedical (Ventura, Calif.). Curcumin (C-3 complex) extracted under GMP conditions was a generous gift from Sabinsa Corporation (East Windsor, N.J.). All the materials were used as received without any further analysis.

The curcumin implants (i.e., the biocompatible polymeric matrices incorporating curcumin) were then prepared by first dissolving curcumin (20% w/w) in ethanol, and the polymers (PCL-121K and PEG-8K in 65:35 ratios) in dichloromethane. Both solutions were then mixed together to prepare a homogenous solution of drug and polymers. The solvents were evaporated on a water bath maintained at 65° C. followed by overnight drying under vacuum at 65° C. to remove residual solvents to prepare an amorphous molecular dispersion of drug in polymer. The dried molten polymer was then extruded through silastic tubing mold (internal diameter 3.4 mm) attached to a syringe. After a few minutes, the cylindrical implants were removed from the tubing and excised into desired lengths (2.0 cm, 200 mg containing 40 mg drug) and stored at −20° C. under argon until used.

The in vitro release of curcumin from the implants was studied under simulated conditions by using 10 ml (PBS) (pH 7.4) supplemented with 10% (v/v) bovine calf serum (BCS) in amber-colored vials to reduce light- and pH-mediated degradation. PBS was supplemented with BCS (10% v/v) to mimic extracellular fluid composition and to simulate the in vivo situation. Amber-colored vials (n=3) containing a 2-cm implant each were incubated at 37±0.5° C. in a reciprocating (150 rpm) shaker water bath (Julabo S W23, Seelbach, Germany), and the release medium was changed after every 24 h. To the collected medium, 1 ml ethanol was added to solubilize any precipitated drug, and curcumin concentration was measured spectrophotometrically at 430 nm using SpectraMax M2 Microplate Reader (Molecular Devices, Sunnyvale, Calif.).

The in vivo cumulative release was studied in female Augustus Copenhagen Irish (ACI) rats following an approved protocol from an Institutional Animal Care and Use Committee (IACUC). All the animals were randomized into four groups as: (1) untreated (no intervention, provided with control diet; AIN-93 M), (2) sham implants treated (two 2-cm blank implants prepared without curcumin), (3) two 2-cm curcumin implants and (4) curcumin diet. Curcumin diet was prepared and supplied as pellets by Harlan Laboratories, by mixing curcumin (at 1000 ppm). All the animals were provided food and water ad libitum. Sham and curcumin implants were subcutaneously grafted at the back of the rats and were monitored for their diet intake and body weight. Animals were euthanized at different time intervals by asphyxiation to collect blood, liver, brain, local tissues and implants. All the tissues were snap frozen in liquid nitrogen and stored at −80° C. until further analysis. Implants were dried overnight under vacuum, weighed and stored at −80° C. until analysis of the residual curcumin content.

Initial and residual curcumin content in the implants was also analyzed to determine the cumulative drug release. Implants recovered from animals were dissolved in 5 ml dichloromethane. Once the implants were dissolved, 5 ml ethanol was added to completely dissolve the curcumin. The solution was then diluted suitably (400-fold) with ethanol. Drug concentration was measured by UV spectrophotometer at 430 nm to calculate the amount of curcumin released in vivo using following equation:

$$\text{Average daily release} = (\text{residual amount at } T_n - \text{Residual amount at } T_{n-1})/T_n - T_{n-1}(\text{Days})$$

where $T_1, T_2, T_3, \ldots T_n$ are different time intervals.

Plasma pooled from all the animals (1.5 ml) was mixed with 200 μA of 0.5 M sodium acetate to reduce the pH to 5. Plasma was then extracted three times with 3 ml ethyl acetate. Ethyl acetate extracts were pooled and dried under vacuum. The dried residue was reconstituted in 100 μl of acetonitrile, and one-half of the solution was analyzed by HPLC. Similarly, liver or brain tissue (approximately 500 mg) from each animal was homogenized in 3 ml PBS (pH 7.4) containing 200 μl sodium acetate (0.5 M). The homogenate was then extracted twice with two volumes of ethyl acetate. After evaporation of ethyl acetate under vacuum, the residue was reconstituted in 1 ml acetonitrile. The solution was filtered through 0.45 μm glass-microfiber filter and evaporated again under vacuum. The residue was finally reconstituted in 100 μl acetonitrile, and one-half of it was analyzed by HPLC using a Shimadzu liquid chromatography system equipped with LC-10ADVP pump, RF-10AXL fluorescence detector and a Shimadzu $C_{18}$ column of 5 μm particles (250×4.6 mm). The three curcuminoids were separated by using acetonitrile and 1% citric acid (adjusted to pH 2.5) at a flow rate of 1 ml/min with a gradient elution in which acetonitrile concentration was increased from 0% to 30% in first 5 min, followed by an increase to 45% in next 5-20 min. Acetonitrile was then maintained at this ratio till 36 min. Curcuminoids were detected using 410 and 500 nm as excitation and emission maxima, respectively, in the fluorescence detector.

To evaluate the xenobiotic-metabolizing enzymes, liver samples from the animals (approximately 100 mg) were homogenized in 0.25 M sucrose buffer (pH 7.4) at 3000 rpm with Polytron. The homogenate was centrifuged at 3000 g for 20 min at 4° C. to separate the nuclear content, and the supernatant was then collected and again centrifuged at 11,000 g for 20 min at 4° C. to separate the mitochondria. The post-mitochondrial supernatant was then transferred to ultra-centrifuge tubes and finally centrifuged at 100,000 g for 1 h at 4° C. to separate the microsomes. The pellet was suspended in 1 ml sucrose buffer, aliquoted and stored at −80° C. until use.

Microsomal proteins were subsequently quantified using a bicinchoninic acid (BCA) method and a BCA™ Protein Assay kit (Thermo Scientific, Rockford, Ill.) and were resolved by sodium dodecyl sulfatepolyacrylamide gel electrophoresis (SDS-PAGE) on a 10% gel. Protein bands were then transferred to polyvinylidene diflouride (PVDF) membrane, which was incubated with 5% non-fat dried milk in Tris-buffered-saline for 1 h at room temperature (25° C.) to block the non-specific binding sites. The membrane was then incubated with primary antibodies for CYP1A1 and GSTM, followed by horseradish peroxidase-conjugated secondary antibody. The bands were detected by enhanced chemiluminescence using Pierce® ECL Western-Blotting Substrate (Thermo Scientific, Rockford, Ill.) and quantified using VersaDoc Imaging System (BioRad Laboratories, Hercules, Calif.).

Upon completion of the foregoing experiments, it was observed that the further optimization studies showed that replacement of F-68 (10% w/w) with polyethylene glycol-8K (35% w/w) significantly enhanced drug release both during an initial burst phase as well as during a controlled release phase. Furthermore, these implants were found to be safe and biocompatible for at least a period of 3 months without any effects on physical well-being of the animals, as the curcumin doses administered by the implants were safe and did not induce any biochemical changes in liver and kidney function. As such, the further study was designed in continuation to above-described experiments (i) to analyze the in vivo release from these implants, (ii) to compare the tissue distribution of curcumin delivered via these implants with curcumin delivered via diet, and finally (iii) to compare the efficacy of curcumin delivered via both routes.

The in vitro release studies described above were performed under simulated conditions using 10 ml PBS supplemented with 10% bovine calf serum to mimic extracellular fluid composition (FIG. 35). Curcumin release was measured in whole release media by replacing it with fresh media after every 24 h. These implants were found to exhibit diffusionmediated Higuchi kinetics ($r^2>0.97$) with biphasic release pattern under in vitro conditions. An initial burst phase was observed for the first 7-8 days with a release of approximately 570 μg of curcumin on day 1 that decreased rapidly to approximately 390 μg on day 2 to approximately 200 μg/day after 1 week. A controlled release was observed in the 2nd phase, where rate of drop in drug release was relatively lower, and release was approximately 120 μg/day even after 31 days (FIG. 35). This initial burst release was due to rapid dissolution of surface bound phytochemical agent into the release media, and once the agent release started from inner layers of polymeric matrix, a more controlled release was observed in the 2nd phase. Furthermore, cumulative release was found to be approximately 15% of total agent load (40 mg per implant) after 1 month.

As also described above, cumulative in vivo release was determined by measuring the residual drug content in implants grafted and recovered from ACI rats after specific time intervals (FIG. 36). The in vivo release was observed to mimic the in vitro release with a burst release of approximately 1800 μg on day 1 which rapidly declined to approximately 380 μg on day 4 after which more stable release kinetics were observed. Drug release was found to be 300-350 μg/day for over a period of 1 month and then reduced to approximately 130 μg/day after 3 months. Cumulative in vivo release was approximately 30% after 1 month which was approximately 1.8- to 2-fold higher than in vitro release suggesting a good correlation between simulated in vitro and in vivo conditions. Furthermore, only 47% (19 mg of 40 mg) drug was found to be released from these implants over a period of 3 months showing their potential to deliver curcumin for extended periods of time (perhaps a year or longer).

Moreover, this release was higher than with PCL implants containing 10% (w/w) either F-68 or polyethylene glycol-8K. Without wishing to be bound by any particular theory, it was believed that this higher release was due to inclusion of 35% polyethylene glycol-8K which, being water soluble, not only provides a more porous microstructure but also increases the hydrophilicity of the polymeric matrix. Weight loss studies showed that these implants lost a weight of approximately 36.3 mg after 1 day of implantation. Since PCL is a semi-crystalline polymer with long half-life of degradation (2-3 years), this weight loss was assumed to be due to release of PEG (34.5 mg) and curcumin (1.8 mg) (PEG-8000 release was measured by subtracting the amount of released curcumin and weight of dried implant recovered from animals from initial weight of the implants).

During in vivo release, extracellular fluid from the site of implantation enters into the polymeric matrix, dissolves the drug and diffuses out into the surrounding tissue. Curcumin from surrounding tissues then enters into the systemic circulation and is distributed to different tissues. Therefore, tissue concentrations of curcumin delivered via both diet and via implants was further measured in plasma, liver and brain. As noted above, curcumin was extracted from the tissues using solvent extraction and analyzed using HPLC coupled with a fluorescence detector with an extraction efficiency of approximately 90% from plasma and approximately 70% from tissues (liver and brain). Fluorescence detector was used due to very high fluorescence of curcumin, which not only increased the specificity of curcumin detection but also increased the sensitivity by at least 4- to 5-fold. The lower limit of detection in plasma was found to be 125 pg (340 pM), and limit of quantification was approximately 200 pg (540 pM) by this method.

When approximately 500 μl of plasma from each individual animal was extracted and analyzed by HPLC, the levels were found to be very low and were below the quantification limit of the method. Therefore, to increase the specificity and reliability of quantification, the extraction was performed with 1.5 ml plasma by pooling 250-350 μl of plasma from all the animals (4-6 in each group) (FIG. 37). The plasma curcumin levels from the implants group were found to be 3.3 ng/ml (9 nM) on day 1 which decreased rapidly to 1.4 ng/ml (4 nM) on day 4 after which a slow and steady decrease in plasma concentration was observed reaching ~0.2 ng/ml (543 pM) after 3 months. Curcumin diet on the other hand showed different kinetics in that curcumin was detected only on day 4 at a level of 0.3 ng/ml (815 pM) decreasing to 0.2 ng/ml after 12 days (543 pM) and was undetectable on 25 and 90 days. It was counterintuitive that instead of the fact that curcumin diet consumption was constant at all the time periods, curcumin was not observed on day 1 and a decline in plasma curcumin concentrations was observed after day 4, suggesting time- and exposure-dependent absorption kinetics. Furthermore, curcumin due to its lipophilic nature exhibits biphasic elimination kinetics with rapid equilibration and distribution of plasma curcumin into various tissues. It was, therefore, also possible that due to high tissue distribution of curcumin, initially almost all curcumin equilibrated into tissues and was not observed in plasma on day 1. However, with time, as the lipophilic tissues became saturated, curcumin was observed in plasma after 4 days on dietary administration.

It is known that curcumin possesses poor oral bioavailability owing to its low aqueous solubility and rapid metabolism both in intestine and in liver. Therefore, to further understand the kinetics of curcumin delivered via both the routes, its concentration in the liver was also measured (FIG. 38). Curcumin delivered via both routes was found to be at similar levels in liver and was 25-30 ng on day 1. The levels increased slightly, though insignificant, on day 4 after which the levels declined to 10-15 ng after 12 days. This trend was found to exactly mimic the plasma concentrations suggestive of hepatic regulation of plasma curcumin levels at least via dietary route. Curcumin is known to induce the expression and activity of various enzymes like CYP1A1, GSTM, and CYP3A4, and it appears that significant amounts of curcumin that reaches the liver tissue from days 1 to 4 induce its own metabolism by increasing the expression/activity of these xenobiotic metabolizing enzymes. The levels decreased significantly after 12 days and stayed almost constant afterward. However, the curcumin concentration was 1000 ppm in the diet, which corresponds to around 900 mg delivered over a period of 90 days (or 50 mg/kg b.wt. per day considering an average weight of 200 g per rat) as opposed to only 38 mg delivered by both the implants combined (2.11 mg/kg b.wt.). Furthermore, curcumin concentration was found to be much higher (10- to 20-fold) in the liver as compared to plasma via both routes, again suggestive of its high tissue distribution. High curcumin concentrations in hepatic tissues via dietary administration were expected as most of the orally administered curcumin gets absorbed into the liver, where it undergoes rapid metabolism. However, similar behavior from the implant route was unexpected as it bypasses the hepatic first-pass metabolism and almost all of the administered curcumin directly reaches into the systemic circulation. Therefore, a much higher concentration was expected in plasma from implant route. It appears that such a pharmacokinetic behavior also originated from curcumin's high lipophilicity resulting in high tissue distribution as compared to plasma. Moreover, since physiologically liver is a highly perfused organ and gets around 23% of total cardiac output, it is highly probable that most of the curcumin that reaches into the systemic circulation might get rapidly equilibrated and entrapped into the liver tissue. An almost constant liver concentration of curcumin from 12 to 90 days also suggests tissue binding of this compound.

To further assess the foregoing observations, curcumin concentration in the whole brain tissue was further analyzed as the brain is also one of the highly perfused organs. Brain tissue was also selected because of curcumin's known potent activities against Alzheimer's disease and against brain gliomas, where continuous localized/systemic delivery of this compound could make a significant improvement in the life of such patients.

Analysis of brain tissue showed almost constant levels of curcumin (2-3 ng/g) from dietary administration at all the time points (FIG. 39). Although curcumin was not found in plasma on day 1 in the dietary curcumin group, it was present in brain tissue. This observation further supported the finding that initially all the curcumin that escaped from liver and reached the systemic circulation partitioned into highly lipophilic sites like the liver and other tissues. However, as equilibrium was established between plasma and other organs like the brain (through blood brain barrier), curcumin started to accumulate in plasma and could be detected after 4 days of oral administration. Furthermore, constant curcumin levels in brain tissue were detected even at 90 days again suggesting increased metabolism of curcumin in liver tissues that led to decreased curcumin concentration in liver at 12 days.

On the other hand, curcumin delivery to the brain via implant route showed biphasic kinetics similar to liver. Since drug concentration that reaches a tissue is determined by rate and extent of its perfusion by systemic circulation, the brain showed rather high curcumin levels (30±7.3 ng/g tissue), almost equal to liver concentration on day 1 of implantation. This concentration dropped slowly to around 7.26±2.45 ng/g tissue after 12 days and stayed almost at the same levels even after 90 days. It was noted that the brain concentration was slightly less than the liver concentration from 12 to 90 days (a constant drug concentration period), which may be attributed, physiologically, to the liver receiving approximately 23% of cardiac output and brain receiving slightly less than liver (approximately 18%). This finding again showed that tissue distribution from the implant route was perfusion rate limited and was dictated by cardiac output to that particular organ. It may also be noted that curcumin concentration in the brain tissue was approximately 3.5-fold higher by the implant route.

Analysis of curcumin in different tissues showed that plasma curcumin concentration via dietary administration was regulated by the liver. At high liver concentrations, a fraction of dietary curcumin escaped hepatic first-pass metabolism, entered the systemic circulation and was distributed to other organs. However, this was not the case with the implant route, where plasma was the first site of curcumin absorption and from where it then was simultaneously distributed to all the other tissues. In view of these findings, it was possible that to administer curcumin to other organs like prostate or pancreas, which are not richly supplied with blood, dietary administration might not be an appropriate route. In such cases, it was believed that direct systemic administration either via parenteral routes or via implant route was a better alternative.

Various in vitro and cell culture studies using the presently-described compositions have showed that curcumin's effective concentration is 5-20 µM depending upon the cell line used. Since the plasma and liver concentrations observed in the foregoing in vivo study (78-95 nM) were much below these, it was also determined whether those concentrations were effective to modulate hepatic cytochromes as studies have shown that curcumin is a natural agonist of aryl hydrocarbon receptor (AhR)/pregnane xenobiotic receptor (PXR) pathway and induces the expression of phase I enzymes like CYP1A1 [24] and CYP3A4. Furthermore, curcumin also interacts with the keap1 protein to lower its affinity for nuclear factor (erythroid-derived 2)-like 2 (Nrf2) protein followed by Nrf2 translocation into the nucleus to induce phase II enzymes like glutathione-S-transferase(µ) (GSTM). As such, hepatic microsomes were isolated and analyzed for CYP 1A1 (an inducible cytochrome), and GSTM levels by Western blotting and activity of CYP3A4 (a drug-metabolizing enzyme) after 1, 4, 12, 25 and 90 days of curcumin treatment by both dietary and implant routes.

As evident in FIG. 40, curcumin implants were found to induce expression of CYP1A1 by approximately 2-fold after 4, 12, 25 and 90 days of treatment. Although a 2-fold increase in CYP1A1 was observed on day 1 also, yet the effect was masked by PEG-8000 as a similar effect was also observed in sham implants (blank implants prepared with only PCL-121 and PEG-8 K without any drug) at this time point and this effect from the sham implants was absent at all other time points. This effect from sham implants was presumably due to release of significant amounts of PEG-8000 on the first day (approximately 34.5 mg), which decreased significantly to only 2.2 mg/day from 2 to 4 days (total approximately 6.5 mg over 3 days). Curcumin diet, on the other hand, increased the CYP1A1 levels only slightly on day 1 (1.43-fold), which returned to basal levels after 4 days, and in fact, the levels were downregulated after 25 and 90 days of treatment. Since the hepatic curcumin levels were similar by both the routes tested, such route-dependent differences in induction of CYP1A1 expression were counterintuitive. It is known that various chemopreventives like indole-3-carbinol (13C) are the most effective in inducing CYP1A1 when given orally as compared to when administered systemically. It has been found that polymerization products of indole-3-carbinol like diindolylmethane (DIM) formed under stomach acidic conditions are more effective AhR ligands as compared to the parent compound, thus resulting in higher efficacy of indole-3-carbinol. Curcumin is also known to degrade under slightly basic conditions of intestine forming various active degradation products like ferulic acid and vanillin, and it was possible that one or more of those metabolites might have AhR antagonistic activity resulting in blunting of curcumin's CYP1A1 upregulating activity at initial time points and eventual downregulation after 25 and 90 days of treatment. GSTM, on the other hand, was not found to get modulated via either of the routes.

The effect of curcumin on CYP3A4 activity was also measured as that enzyme was one of the drug-metabolizing enzymes known to get induced by curcumin (FIG. 41). As was observed with CYP1A1 expression, CYP 3A4 activity was also found to be slightly increased by sham implants both at day 1 and day 4 but became significant only after 12 days of treatment, which again dropped to basal levels by 25 days. From the weight loss data, it was evident that from 1-12 days, there was a weight loss of approximately 20 mg out of which 13.4 mg was from loss of PEG-8 K. It appeared that low concentrations of PEG (approximately 1.0 mg/day), which were insufficient to increase CYP1A1 expression after day 1, were sufficient to increase the CYP3A4 activity.

Similar to sham implants, curcumin implants were also found to increase the activity from day 1 to day 12 of treatment as compared to untreated animals; however, this increase became significant only after 25 days when compared with sham implants. This enhanced activity remained consistently upregualated even after 3 months of treatment (in contrast to sham implants) and did not reduce to basal levels after 25 days. On the other hand, curcumin diet showed slightly higher activity on day 1 of treatment, which was significant higher after 4 days as compared to untreated animals and again reduced to basal levels at 12 days of treatment. It thus appeared that continuous delivery of curcumin directly into the systemic circulation by the implant route was more effective in increasing and maintaining the higher CYP3A4 activity as compared to dietary route.

From the foregoing results, it was thus further determined that the biocompatible polymeric matrices of the presently-disclosed subject matter were a viable alternative for the delivery of curcumin and to circumvent its bioavailability issue that are observed when it is adminstered by the traditional oral route. These studies showed that subcutaneous polymeric implants provided a controlled release of curcumin at the local site from which it gets absorbed into the systemic circulation and then is distributed to all the tissues simultaneously, and the implants were found to provide higher curcumin concentrations in plasma, brain and to some extent in liver over a period of 3 months as compared to dietary administration. The higher plasma and tissue levels by the implants were achieved by a reduction of curcumin dose by nearly 20- to 25-fold for over a period of 3 months as compared to the traditional dietary route. Furthermore, curcumin delivered directly into the systemic circulation was found to be more efficacious in inducing CYP1A1 and CYP3A4 enzymes required for its chemopreventive activity against various environmental carcinogens. The presence of significantly higher concentrations of curcumin in tissues like brain showed potential of the presently-described compositions for patients suffering with Alzheimer's disease and/or brain gliomas, where curcumin has shown significant potential in various in situ and cell culture studies.

Example 19

Coating of Composition

Given the observation of the burst effect, which includes the substantial initial release of the therapeutic agent from the biocompatible polymeric matrices of the presently-disclosed subject matter upon administration, studies were undertaken to minimize the effect and provide a more sustained release. In this regard, it was found that coating the biocompatible polymeric compositions with blank polymers (e.g., polycaprolactone that did no include any phytochemical agents mixed in the polymers) significantly minimized and, in some cases, eliminated the burst release effect from standard polycaprolactone implants (implants prepared by extrusion method hereafter called "Extruded implants"). Indeed, several phytochemical agents were found to be released at a much higher rate ("burst" release) in the first several days, followed by a constant decline and, while the burst release phenomenon provided high systemic doses and was useful for some compounds, it was also possible to have local or systemic toxicity for other compounds. Withaferin A, cucurbitacin B are some of the examples which showed burst release phenomenon and sign of local toxicity. It was surprisingly found, however, that the burst release effects could be minimized or eliminated by adding multiple coatings of blank polycaprolactone by dipping and drying extruded implants in a 5-15% solution of PCL in dichloromethane. FIG. 42 shows this effect for extruded implants of curcumin.

Example 20

Analysis of Coated Implant Formulations

The extruded implant formulation described herein above involved a heating step (70° C.) to evaporate the solvent(s) as well as for melting of the polymer matrix containing the desired agent for extruding it into cylindrical implants. As such, in certain embodiments, the technology was not easily adapted for heat-labile compounds. To address this issue, a further polymeric matrices formulation was developed in which blank PCL implants (about 1.2 mm diameter), prepared by the extrusion method, were coated with 20-40 layers of 5-15% solution of PCL in dichloromethane containing a desired amount of a particular agent (e.g., a phytochemical agent) dissolved either in dichloromethane or another appropriate solvent which was miscible with dichloromethane. Briefly, to produce the additional formulation, $\epsilon$-polycaprolactone (mol. wt. 80,000; P-80) was purchased from Sigma-Aldrich (St. Louis, Mo., USA); Pluronic® F68 (F68) was used from BASF Corp. (Florham Park, N.J., USA); silastic tubing (1.4 mm internal dia) was purchased from Allied Biomedical (Ventura, Calif., USA); disposable syringes (5 ml) were purchased from BD Biosciences (Franklin lakes, N.J., USA); penicillin-streptomycin solution was purchased from Invitrogen (Carlsbad, Calif.); amber vials (20 ml) were purchased from National Scientific (Rockwood, Tenn., USA); curcumin and the three curcuminoids, curcuminoid I, curcuminoid II (demethoxycurcumin) and curcuminoid III (bis-demethoxycurcumin) were generous gifts of Sabinsa Corp. (East Windsor, N.J., USA); oltipraz was obtained from the National Cancer Institute chemoprevention branch (Bethesda, Md., USA); withaferin A was isolated from standardized extract of *Withania somnifera* (Sabinsa Corp, East Windsor, N.J., USA); bovine calf serum was purchased from Hyclone (Logan, Utah, USA); dichloromethane (DCM), absolute ethanol and acetonitrile were purchased from BDH chemicals (VWR, West Chester, Pa.), Pharmco-AAPER (Louisville, Ky., USA) and Sigma-Aldrich (St. Louis, Mo., USA), respectively; and phosphate-buffered saline (PBS) pellets and tricaprylin were purchased from Sigma-Aldrich (St. Louis, Mo., USA)

To formulate the "coated" polymeric implants, blank P-80 implants (1.4 mm dia) were then prepared by dissolving P-80:F68 (9:1) in dichloromethane, followed by evaporation of the solvent in a Petri dish under hood and extrusion of the molten polymer through a silastic tubing mold, similar to the methodologies described herein above. Those blank implants were coated with about 20-30 layers of 10% P-80 solution in dichloromethane containing 1.0% oltipraz, curcumin, or individual curcuminoids I, II and III, except for withaferin A which was present at 0.3 and 0.5%. For coating, one end of the blank implant (2.5-3.5 cm) was inserted into a silastic tube plug (6 mm long, 1.4 mm dia) while the other end of the plug was attached with a pipet tip. Coatings were then added by dipping the blank implant into the solution with intermittent drying with cool air using a commercial hair dryer and placing them under hood. Twenty to 30 layers (i.e., dippings) generally resulted in 2.6 mm diameter coated implants as measured by a digital caliper. Implants formulated in this manner had a 10% drug load of the test agents, except for withaferin A which represented 3% and 5% load. The assembly was placed under hood overnight to remove the residual DCM, implants were excised in 1 or 2 cm lengths and stored in amber vials under argon at −20° C. until used.

The rate of in vitro release for the implants was subsequently measured. Briefly, 1-cm implants were placed in 10 ml PBS containing 10% bovine calf serum and 1% penicillin-streptomycin solution in 20-ml amber vials. The vials were placed in a water bath (Julabo S W 23, Seelback, Germany) at 37° C. with constant agitation at 110 rpm. The medium was changed every 24 h. To the release medium collected was added ethanol (10% final conc.) to solubilize the compound, except for withaferin A which was extracted using acetonitrile and chloroform. The release was measured spectrophotometrically using the following absorbance maxima: oltipraz (430 nm), curcumin (430 nm), curcuminoid I (429 nm), curcuminoid II (424 nm), curcuminoid III (419 nm), and withaferin A (215 nm).

To assess the coated implants (i.e., where the compositions were in the form of coatings), in vivo studies were also performed. To analyze the effected of the "coated" implants on DNA adducts, following acclimation, 5-6 week-old female A/J mice (Harlan Laboratories, Indianapolis, Ind.) were treated with sham or coated polymeric implants (two 1.5 cm implants, 60 mg/implant) of oltipraz, curcumin, curcuminoid I, curcuminoid II, curcuminoid III and withaferin A. Drug load in the implants was approximately 10%, except for withaferin A which was approximately 3%. All groups of animals were also treated with dibenzo[a,l]pyrene (DBP) via polymeric implants (1-cm, 1.4 mm dia, 5% DBP load) at the same time. Implants were grafted subcutaneously, and animal were euthanized after 3 weeks. Two additional groups of mice received only withaferin A implants to determine the rate of release in vivo and those animals were euthanized after 2 and 8 weeks. In both cases, animals were euthanized by $CO_2$ asphyxiation and selected tissues (lung, liver and brain) were collected and stored at −80° C. until processing. Implants were also recovered, dried under vacuum and stored in amber vials under argon at 4° C. until analysis.

To assess the toxicity of the implants, blood was collected separately at the time of euthanasia and hematological parameters were analyzed using whole blood by Cell Dyn 3500 hematology analyzer (Abbott laboratories, Santa Clara, Calif.). Serum was used to analyze the liver and kidney function test. An ion selective electrode was used for various electrolytes analysis and in-built spectrophotometric techniques were used for all other biochemical parameters analysis on automated AU640 Chemistry analyzed (Beckman Coulter, Inc., Brea, Calif.).

The measurement of residual oltipraz, curcumin, curcuminoids I, II and III and withaferin A in the implants was performed by dissolving the initial and residual contents of the test agent in implants in 5 ml dichloromethane (DCM), diluted with ethanol (1:1), and finally centrifuged at 12,000 g to discard the polymer pellet. The supernatants were diluted with ethanol:DCM (80:20) and their concentrations were measured spectrophotometrically at maximal absorbance and the concentrations were calculated against standard curves of individual compounds.

To analyze the formation of DNA adducts, DNA was isolated from lung tissue (200 mg) by treatment of the isolated crude nuclei with RNases and proteinase K, followed by extractions with phenol, phenol:Sevag and Sevag. DNA was recovered by ethanol precipitation and its concentration was measured spectrophotometrically considering 1 $A_{260}$ equals 50 μg DNA. DNA adducts were analyzed by nuclease P1-mediated $^{32}$P-postlabeling/TLC assay and expressed as adducts per $10^9$ nucleotides.

To analyze tissue curcumin/curcuminoids levels, tissue levels were measured by solvent extraction, where the eluates were analyzed by ultra performance liquid chromatography (UPLC). Briefly, liver and brain tissues (500 and 400 mg, respectively) from each animal were homogenized in 3 ml PBS (pH 7.4) containing 200 μl of 0.5 M sodium acetate, and extracted with ethyl acetate. After evaporation of the pooled extracts, the residue was reconstituted in 100 μl acetonitrile and analyzed by UPLC using Shimadzu UPLC system (Kyoto, Japan), with a Shim-Pack XR-ODS II reverse phase column (Shimadzu; 150×3.0 mm i.d., 2.2 μm). The three curcuminoids, curcumin, demethoxycurcumin and bis-demethoxycurcumin (75:25:5), were separated by using acetonitrile and 1% citric acid (pH 2.5) at a flow rate of 0.75 ml/min with a linear gradient elution in which acetonitrile concentration was increased from 2 to 30% in first 2 min, followed by an increase to 45% from 2 to 6.4 min; the latter ratio was then maintained till 11.5 min and finally decreased to 2% in 13 min. The curcuminoids were detected using 410 and 500 nm as excitation and emission maxima, respectively, in the fluorescence detector and total curcumin concentration was calculated from standard curves of individual curcuminoids.

As described herein above, biocompatible polymeric matrices incorporating amounts of curcumin, green tea polyphenols and many other chemopreventive phytochemical agents, when grafted subcutaneously in rodents, provide controlled systemic delivery for long durations. That polymeric implant formulation (the "extrusion" method), however, was not readily adaptable to some heat-labile compounds. Further, the implants prepared by those method generally accompanied an initial burst release of the compound. From the foregoing described experiments, however, it has been found that the coated implant formulations circumvent the limitations of the implants formulated by the extrusion method.

As described above, the "coated" polymeric implant formulation was developed using structurally diverse compounds, namely, oltipraz, curcumin and its three constituents, curcuminoids I, II and III, and withaferin A. Oltipraz, an analogue of thiol-3-thione, a constituent of cruciferous vegetables, has been reported as an effective chemopreventive agent in pre-clinical studies, and has been extensively used as an antichistosomal drug in Europe. All previously reported pre-clinical studies with curcumin have been done with commercial curcumin which is a mixture of three curcuminoids. Withaferin A, a triterpenoid, represents a the principal bioactive of the herb *Withania somenifera*, commonly known as "ashwagandha", as part of the 'ayurvedic' folklore medicine in India.

As also noted above, the coated implants were formulated by coating multiple layers of the polymer (P80) solution in dichloromethane, with or without test agents, with intermittent drying with cool air on blank P80 implants (1.4 mm dia). Twenty or 30 coatings of 20% and 10% polymer solution, respectively resulted in cylindrical implants with about 2.6 mm diameter. The number of coatings depended upon the polymer solution concentration which, in turns, depended upon the solubility of test agent in dichloromethane or other appropriate solvent.

When coated implants of oltipraz, curcumin and withaferin A were agitated in PBS alone at 37° C., there was essentially no release. However, the presence of 10% bovine serum in the release medium, which mimics the in vivo scenario of extracellular fluid, showed that all test agents were released from the implants at controlled rates. Oltipraz implants showed essentially zero-order kinetics over a period of 60 days, with a cumulative release of about 12% and 27% after 21 and 60 days, respectively (FIG. 43A). However, withaferin A was released with some initial burst release. The initial burst release phenomenon for this compound lasted for only two days; subsequently, the release was more sustained, with accumulative release of about 20% over 3 weeks (FIG. 43B). On the other hand, withaferin A implants formulated by the extrusion method resulted in a cumulative release of about 35% over 3 weeks, largely because the burst release effect this type of implant formulation was more pronounced and lasted for several days compared with the coated implants. Curcumin implants did not show any initial burst release but the rate of release declined gradually, resulting in a cumulative release of about 20% over 3 weeks (FIG. 43C).

Figure 44A:
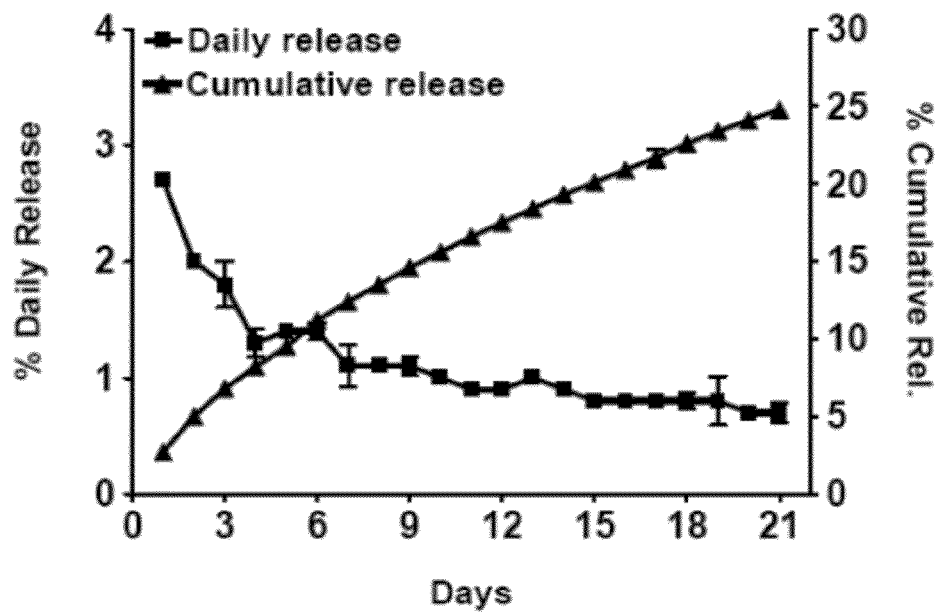
Figure 44B:
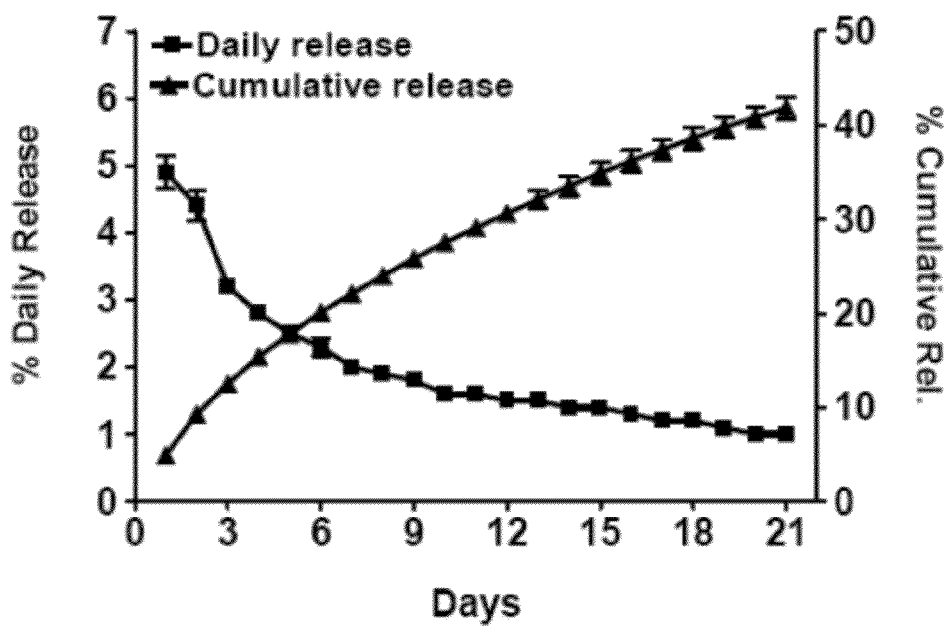
Figure 44C:
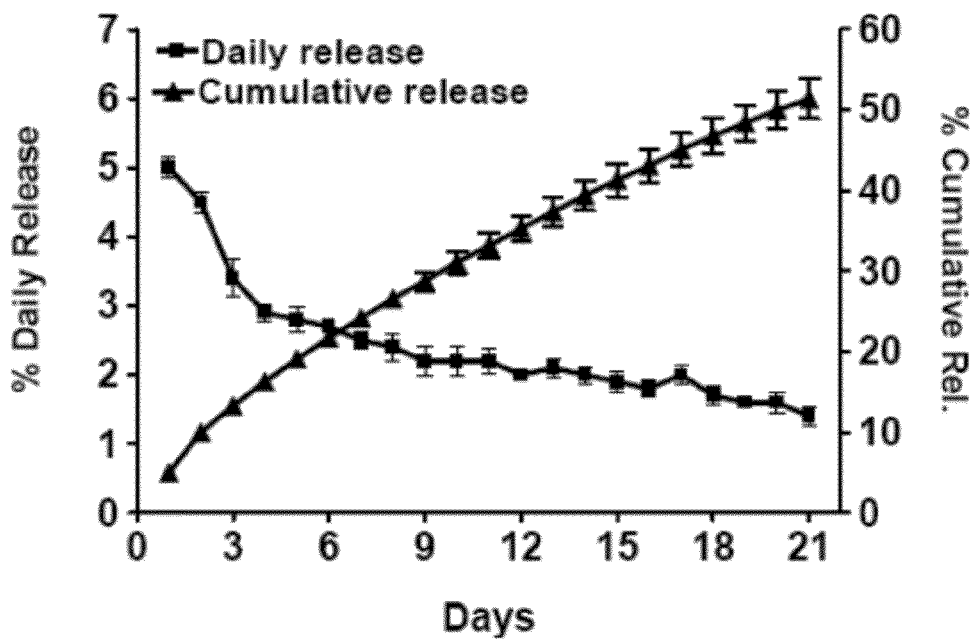
Figure 44D:
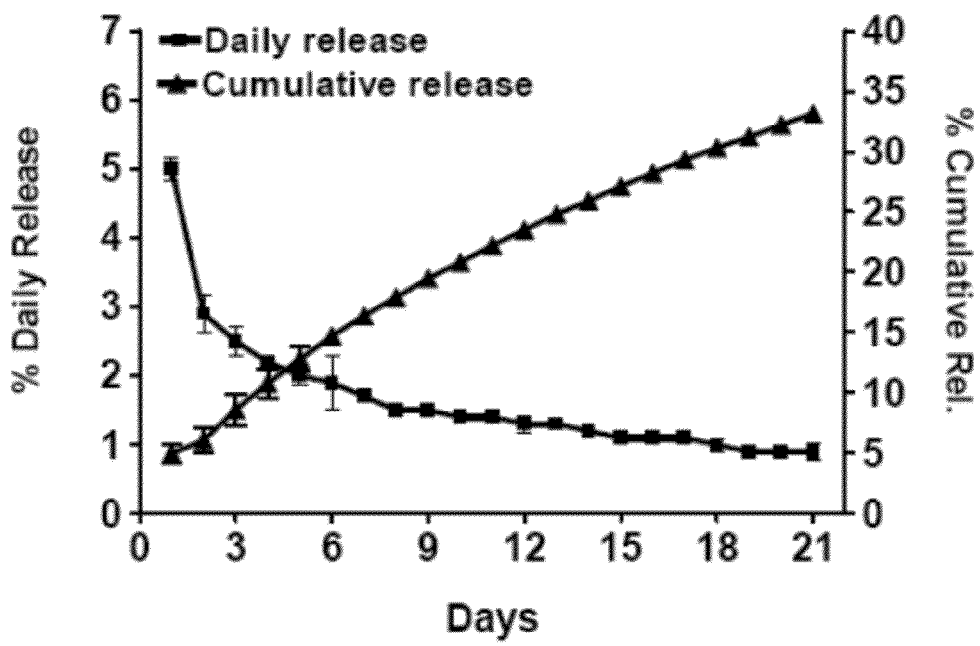

To determine the effect of substituents on the rate of release, coated implants were prepared from individual constituents of curcumin, i.e., curcuminoid I, curcuminoid II (demethoxycurcumin) and curcuminoid III (bisdemethoxycurcumin). While no noticeable differences were found during the formulation of the coated implants, the three curcuminoids were released at different rates, with the cumulative release over 3 weeks being in the following descending order: curcuminoid I (24.8%), curcuminoid II (41.8%) and curcuminoid III (51.4%) (FIGS. 44A, 44B, and 44C, respectively). Thus, it appeared that the presence of none (curcuminoid III), one (curcuminoid II) and two (curcuminoid I) methoxy groups in the curcuminoid structures significantly influenced the rate of release, indicating that the presence of lipophilic group(s) in the structure can reduce the rate of release of the compound from the implants.

Measurement of the residual amounts in the implants recovered from the animals used in the in vivo studies at the end of the 3 week experiment showed that the total release was in the following descending order: withaferin A (30.7%), curcumin (19.9%) and oltipraz (18.6%) (FIG. 45A). Withaferin A release was also measured at additional times points, i.e., by euthanizing animals after 2 weeks and 8 weeks, in addition to the 3 weeks, and the data presented in FIG. 45B showed that withaferin A continued to be released for 8 weeks, with over 50% of the compound still present in the implants. This release pattern suggested that withaferin A release could last for several more months. As expected, no physical change was observed in the withaferin A implants at the end of 8 weeks, since degradation of P80 implants can take over two years based on the time-dependent decrease in the molecular weights reported for this polymeric material. Comparison of the cumulative release over a period of 3 weeks in vivo and in vitro (FIG. 45A) for all the test agents indicated that the in vivo release was 1.3-1,8-fold higher than the respective in vitro release. The higher release in the animal system presumably resulted from the 'sink' conditions.

As also described above, to determine the effect of chemopreventives delivered by the coated polymeric implants, as well as to determine their rates of release in vivo, groups of female A/J mice (n=4-5) were acclimated and then grafted subcutaneously with implants of oltipraz, withaferin A, curcumin and individual curcuminoids I, II and III and simultaneously challenged with low dose of the carcinogen, dibenzo [a,I]pyrene (DBP) via polymeric implants. Analysis of lung DNA by $^{32}$P-postlabeling showed multiple adducts, while no such adduct spots were detected in sham-treated sample. The identity of DNA adducts has previously been established as guanine and adenine derivatives of the electrophilic metabolites, DBP-11,12-diol-13,14-epoxides. No qualitative differences were observed in the adduct profiles in the absence or presence of test chemopreventives. However, quantitative differences were observed. Both withaferin A and oltipraz delivered via the implants showed reduction in the DNA adduct levels but the reduction was statistically significant only with oltipraz (p<0.05) (FIGS. 46A and 46B). Intervention with curcumin and the individual curcuminoids showed virtually no effect on the adduct levels.

As described herein above, it is known that when curcumin is administered orally, it exhibits poor bioavailability and rapid metabolism both in the intestine as well as in the liver. To measure tissue the distribution of curcuminoids delivered by the implant route, curcuminoids were extracted from the lung, liver and brain tissues by solvent extraction and UPLC-UV. All the curcuminoids were readily measurable even after 21 days of grafting the implants. When delivered individually, the three curcuminoids I, II and III were found to be present in essentially the same ratio. In the liver, curcuminoid I and III levels were similar (5-6 ng/g tissue); however, curcuminoid II was present in 4-5 times lower levels (FIGS. 47A and 47B), suggesting this analog underwent more rapid metabolism. Furthermore, when these curcuminoids were given in the form of the mixture as the commercial curcumin, the liver levels of the three curcuminoids I, II and III were found to be present essentially the same ratio as present in the original mixture and the total levels were significantly higher (15 ng/g tissue) than when given individually.

To determine if the individual curcuminoids administered by the implant could cross the blood-brain-barrier (BBB), the brain tissues were also analyzed. Data presented in FIG. 47C demonstrated that while curcuminoids I and II accumulated to similar levels (1.4 and 1 ng/g tissue, respectively), the levels of curcuminoid III were substantially higher (6.4 ng/g tissue). The higher curcuminoid III levels in the brain tissue may result either due to the curcuminoid III levels readily crossing of the BBB and/or lesser metabolism in the brain tissue. The higher accumulation of curcuminoid III in the brain may have biologically important consequences in view of the recent report indicating protecting effects of this curcuminoid against Alzheimer in a cell culture model.

Animals were also observed for the possible toxicity after subcutaneous polymeric implants embedded with chemopreventive agents (withaferin A and curcumin) or DBP. There was no effect on the body weight irrespective of sham of drug implants. No significant differences in various hematological parameters (white blood cells, red blood cells, hemoglobin), liver enzymes (like aspartate transaminase, alanine aminotransferase, alkaline phosphatase, gamma-glutamyl transpeptidase, amylase, or lipase), or biochemical parameters of kidney function (like blood urea nitrogen, creatinine, $Ca^{2+}$, $Na^+$, and $Cl^-$ levels) were observed with any of the compound administered via the implant compared with the sham implant 3 weeks after grafting. Furthermore, neutrophils, lymphocytes, monocytes, eosinophils, and basophils were also analyzed and no statistical difference was observed in the animals treated with polymeric implants.

Additionally, to assess the effect of the implants on tumor xenografts, five- to six-week old female athymic nude mice (Harlan Laboratories, Indianapolis, Ind.) were acclimated for a week and then inoculated with human lung cancer (A549) cells ($3\times10^6$ cells) in matrigel. Following inoculation, two groups of animals (n=10), were treated intraperitoneally with vehicle (tricaprylin) or withaferin A (8 mg/kg, b.wt., respectively) on alternate days, while two additional groups were treated with sham or withaferin A "coated" implants (two 1.5-cm, 5% drug load) after tumor grew to approximately 50 mm$^3$. Animals were weighed and the tumors were measured by a digital caliper weekly. At the end of 6 to 8 weeks, animals were euthanized by $CO_2$ asphyxiation, tumors were collected and measured. Implants were also recovered, dried under vacuum and stored in amber vials under argon at 4° C. until analysis.

To further determine if the coated polymeric implants could deliver therapeutic doses, withaferin A was administered via the implants or intraperitoneally, while control groups received respective sham treatments. Measurement of the body weights weekly showed that sham and withaferin A-treated animals had essentially the same body weight at the end of the 8-week study, indicating that the drug administration via the implants was well tolerated. Measurement of the tumor volume weekly showed a significant reduction of 51% in the growth of the tumor in the group receiving withaferin A via the implants (FIG. 48A). Similar (53%) inhibition of the tumor was observed when withaferin A was given intraperitoneally (8 mg/kg) (FIG. 48B), while no reduction was observed when a lower dose of withaferin A (4 mg/kg) was administered intraperitoneally. The total dose of withaferin A administered via the implants (2.69 mg), calculated based on the residual amount in the implants, was less than one half of the total dose (5.6 mg) given intraperitoneally (8 mg/kg). These data demonstrated that the "coated" implant delivery could be used to achieve a therapeutic dose of withaferin A, and that the effective implant dose was 2.1-fold lower than the dose given by the traditional (intraperitoneal) route, a difference that was only expected to grow as the study was continued.

Based on the results from these experiments, it was thus found that the coated polymeric implant formulations allowed embedding any compound in the polymeric matrix as long the compound was soluble in dichloromethane or any other solvent (e.g., tetrahydrofurone, ethanol and acetone) which is miscible with dichloromethane. Further, since the in vitro release of the test agents correlated with the in vivo release, it was found that is was possible to manipulate the in vivo dose based on the drug load or implant size or both. As such, the polymeric implant formulation accommodated heat-labile compounds, circumvented the problem of oral bioavailability, delivered continuous sustained low doses for long durations (e.g., months), and allowed in vivo efficacy assessment of minor plant constituents and synthetic metabolites which otherwise remains uninvestigated due to their insufficient quantities available.

Throughout this document, various references are cited. All such references are incorporated herein by reference, including the references set forth in the following list:

REFERENCES

1. Aggarwal B B & Shishodia S. (2004) Suppression of the Nuclear Factor-κB Activation pathway by spice derived phytochemicals. *Ann NY Acad Sci* 1030: 434-441.
2. Aggarwal B B, Kumar A and Bharti A C. (2003) Anticancer potential of curcumin: preclinical and clinical studies. *Anticancer Res*, 23: 363-398.
3. Aggarwal B B, Takada Y & Oommen O V (2004) From chemoprevention to chemotherapy: common targets and common goals. *Expert Opin Investig. Drugs* 13: 1327-1338.
4. Aiyer H S, Srinivasan C & Gupta R C. (2006) Dietary berries and ellagic acid diminish estrogen-mediated mammary tumorigenesis in ACI rat model. *Proc Am Assoc Cancer Res* 47: Abst. #1145.
5. Aiyer H S, Vadhanam M V & Gupta R C. (2002) Efficacy of cancer chemopreventive agents in protecting against oxidative DNA damage from $Cu^{2+}$-mediated activation of 4-hydroxy-estradiol. *Proc Am Assoc Cancer Res* 43: 5682.
6. American Cancer Society. (2005) *Breast Cancer Facts and Figures* 2005-2006. American cancer society.
7. American Institute for Cancer Research. (1997) Diet and the cancer process. In, *Food Nutrition and the Prevention of Cancer*: A Global Perspective. BANTA Book Group, Menasha, pp 252-287.
8. Anderson D, Schmid T E, Baumgartner A, Cemeli-Carratala E, Brinkworth M & Wood, J M. (2003) Oestrogenic compounds and oxidative stress (in human sperm and lymphocytes in the Comet assay). *Mutat Res* 544: 173-178.
9. Anilakumar K R, Nagaraj N S & Santhanam K. (2001) Effect of coriander seeds on hexachlorocyclohexane induced lipid peroxidation in rat liver. *Nutr Res* 21: 1455-1462.
10. Arif J M & Gupta R C. (2003) Artifactual formation of 8-oxo-2'-deoxyguanosine: role of fluorescent light and inhibitors. *Oncol Rep* 10: 2071-2074.
11. Arif J M, Gairola C G, Glauert H P, Lubet R A, Kelloff G J & Gupta R C. (1998) Inhibition of cigarette smoke-related lipophilic DNA adducts in rat tissues by dietary oltipraz. *Carcinogenesis* 19: 1515-1517.
12. Arif J M, Gairola C G, Kelloff G J, Lubet R A & Gupta R C. (2000) Inhibition of cigarette smoke-related DNA adducts in rat tissues by indole-3-carbinol. *Mutat Res* 452: 11-18.
13. Arif J M, Gairola C G, Lubet R A, Kellof G J & Gupta R C. (1997) Effects of dietary supplementation off N-acetyl-1-cysteine on smoke-induced DNA adducts in rat tissues. *Int J Oncol* 11: 1227-1233.
14. Banerjee S, Bueso-Ramos C and Aggarwal B B. (2002) Suppression of 7,12-Dimethylbenz(a)anthracene-induced Mammary Carcinogenesis in Rats by Resveratrol: Role of Nuclear Factor-kB, Cyclooxygenase 2, and Matrix Metalloprotease 9. *Cancer Res,* 62: 4945-4954.
15. Bansal S S, Vadhanam M V & Gupta R C. Development and in vitro-in vivo evaluation of polymeric implants for continuous systemic delivery of curcumin. *Pharm Research,* 28:1121-30, 2011.
16. Bansal S S, Goel M, Aqil F, Vadhanam M & Gupta R C. Advanced drug-delivery systems of curcumin for cancer chemoprevention. *Cancer Prev Res.* 4: 1158-1171, 2011.
17. Bansal S S, Kausar H, Aqil F, Jeyprakash J, Vadhanam M V & Gupta R C. Curcumin implants for continuous systemic delivery: safety and biocompatibility. *Drug Deliv. and Transl. Res.* 1: 332-341, 2011.
18. Bartsch H, Nair J & Owen R W. (1999) Dietary polyunsaturated fatty acids and cancers of the breast and colorectum: emerging evidence for their role as risk modifiers. *Carcinogenesis* 20, 2209-2218.
19. Bendich A. (1989) Carotenoids and the immune response. *J Nutr,* 119: 112-115.
20. Bernstein L & Ross R K. (1993) Endogenous hormones and breast cancer risk. *Epidemiol Rev* 15: 48-65.
21. Bettuzzi S, Brausi M, Rizzi F, Castagnetti G, Peracchia G, Corti A. (2006) Chemoprevention of human prostate cancer by oral administration of green tea catechins in volunteers with high-grade prostate intraepithelial neoplasia: a preliminary report from a one-year proof-of-principle study. *Cancer Res.* 66:1234-40.
22. Block G, Patterson B and Sauber A. (1992) Fruit and vegetables and cancer prevention: a review of the epidemiological evidence. *Nutr Cancer,* 18: 1-29.
23. Blot W J, Li J Y, Taylor P R, Guo W, Dawsey S, Wang G Q, (1993) Nutrition intervention trials in Linxian, China: supplementation with specific vitamin/mineral combinations, cancer incidence, and disease-specific mortality in the general population. *J Natl Cancer Inst,* 85: 1483-1492.
24. Bolton J L, Pisha E, Zhang F & Qiu S. (1998) Role of quinoids in estrogen carcinogenesis. *Chem Res Toxicol* 11: 1113-1127.
25. Bolton J L, Trush M A, Penning T M, Dryhurst G & Monks T J. (2000) Role of quinones in toxicology. *Chem Res Toxicol* 13: 135-160.

26. Cao P, Vadhanam M V, Spencer W S, Cai J & Gupta R C. Sustained systemic delivery of green tea polyphenols by polymeric implants significantly diminishes benzo[a]pyrene-induced DNA adducts. *Chem ResTox,* 24: 877-896, 2011.
27. Carolin K A & Pass H A. Prevention of breast cancer. (2000) *Critical Rev Oncol Hemat* 33: 221-238.
28. Castagnetta L A, Granata O M, Arcuri F P, Polito L M, Rosati F & Cartoni G P. (1992) Gas chromatography/mass spectrometry of catechol estrogens. *Steroids* 57: 437-443.
29. Cavalieri E, Frenkel K, Liehr J G, Rogan E & Roy D. (2000) Estrogens as endogenous genotoxic agents—DNA adducts and mutations. *J Natl Cancer Inst Monogr* 27: 75-93.
30. Chadwick C C, Chippari S, Matelan E, Borges-Marcucci L, Eckert A M, Keith J C Jr, Albert L M, Leathurby Y, Harris H A, Bhat R A, Ashwell M, Trybulski E, Winneker R C, Adelman S J, Steffan R J, Harnish D C. (2005) Identification of pathway-selective estrogen receptor ligands that inhibit N F-kappaB transcriptional activity. *Proc Natl Acad Sci USA* 102:2543-8.
31. Chaudhary A K, Nokubo M, Reddy G R, Yeola S N, Morrow J D, Blair I A & Marnett L J. (1994) Detection of endogenous malondialdehyde-deoxyguanosine adducts in human liver. *Science* 265: 1580-1582.
32. Chithra V & Leelamma S. (2000) *Coriandrum sativum*—effect on lipid metabolism in 1,2-dimethyl hydrazine induced colon cancer. *J Ethnopharm* 71: 457-463.
33. Chung F-L, Raghu G N, Ocando J, Nishikawa A & Zhang L. (2000) Deoxyguanosine adducts of t-4-Hydroxy-2-nonenal are endogenous DNA lesions in rodents and humans: detection and potential sources. *Cancer Res* 60: 1507-1511.
34. Cribb A E, Knight M J, Dryer D, Guernsey J, Hender K, Tesch M, Saleh T M. (2006) Role of polymorphic human cytochrome P450 enzymes in estrone oxidation. *Cancer Epidemiol Biomarkers Prev.* 15: 551-8.
35. Dandapani S, Subramanian V R, Rajagopal S & Namasivayam N. (2002) Hypolipidemic effect of *Cuminum cyminum* L. on alloxan-induced diabetic rats. *Pharmacol Res* 46: 251-255.
36. Dickson R B & Lippman M E. Growth factors in breast cancer. (1995) *Endocr Rev* 16: 559-589.
37. DiGianni L M, Garber J E & Winer E P. (2002) Complementary and alternative medicine use among women with breast cancer. *J Clin Oncol* 20: 34s-38s.
38. Dorai T & Aggarwal B B. (2004) Role of chemopreventive agents in cancer therapy. *Cancer Lett* 215, 129-140.
39. Dunnick J K, Elwell M R, Huff J & Barrett J C. (1995) Chemically-induced mammary gland cancer in the National Toxicology Program's carcinogenesis assay. *Carcinogenesis* 16, 173-179.
40. Evans M J, Harris H A, Miller C P, Karathanasis S K, Adelman S J. (2002) Estrogen receptors alpha and beta have similar activities in multiple endothelial cell pathways. *Endocrinology,* 143:3785-95.
41. Foley J, Ton T, Maramport R, Butterworth B, Goldsworthy T L. (1993) Comparison of proliferating cell nuclear antigen to tritiated thymidine as a marker of proliferating hepatocytes in rats. *Environ Health Perspect.* 101: 199-206.
42. Gagandeep, Dhanalakshmi S, Mendiz E, Rao A & Kale R K. (2003) Chemopreventive effects of cuminum cyminum in chemically induced forestomach and uterine cervix tumors in murine model systems. *Nutr Cancer* 47: 171-180.
43. Green S, Walter P, Kumar V, Krust A, Bornert J M, Argos P & Chambon P. (1986) Human estrogen receptor cDNA: sequence, expression and homology to v-erbA. *Nature* 320: 134-139.
44. Greenlee R T, Hill-Harmon M B, Murray T & Thun M. (2001) Cancer statistics, 2001. *CA-Cancer J Clin* 51: 15-36.
45. Greenwald P, Kelloff G J, Burch-Whitman C & Kramer B S. (1995) Chemoprevention. *CA-Cancer J Clin* 45: 31-49.
46. Grilli S. (2006) Tamoxifen (TAM): the dispute goes on. *Ann 1st Super Sanita* 42: 170-173.
47. Gulcin I, Oktay M, Kirecci E, Kufrevioglu O I. Screening of antioxidant and antimicrobial activities of anise (*pimpinella anisum* L.) seed extracts. *Food Chemistry,* 83, 371-382, 2003.
48. Gupta R, Meireles S, Stoner G, Clapper M & Gairola C G. (2006) Cytochrome P450 1B1 as a potential molecular target for cigarette smoke-mediated mouse lung cancer and its prevention—to be presented at the Cancer Susceptibility and Cancer Susceptibility Syndromes, *Am Assoc Cancer Res, Maui, Hi.*
49. Gupta R C & Arif J M. (2001) A TLC enrichment-mediated $^{32}$P-postlabeling assay for the sensitive detection of 8-oxodeoxyguanosine in tissue DNA. *Chem Res Toxicol* 14: 951-957.
50. Gupta R C & Lutz W K. (1999) Background DNA damage from endogenous and unavoidable exogenous carcinogens: a basis for spontaneous cancer incidence? *Mutat Res* 424: 1-8.
51. Gupta R C, Reddy M V & Randerath K. (1982) $^{32}$P-Postlabeling analysis of non-radioactive aromatic carcinogen-DNA adducts. *Carcinogenesis* 3: 1081-1092.
52. Gupta R C, Stoner G & Gairola C G. (2005) Inhibition of cigarette smoke-mediated lung tumorigenesis in A/J mice by dietary berries. *Proc Am Assoc Cancer Res* 46: Abst #3895.
53. Gupta R C. (1985) Enhanced sensitivity of $^{32}$P-postlabeling analysis of aromatic carcinogen-DNA adducts. *Cancer Res* 45: 5656-5662.
54. Gupta R C. (1996) $^{32}$P-Postlabeling for detection of DNA adducts. In: *Technologies for Detection of DNA Damage and Mutations,* Pfeifer G P (ed), Plenum Press, New York, pp. 45-61.
55. Hampton T. (2005) Clinical trials point to complexities of chemoprevention for cancer. *J Am Med. Assoc.* 294: 29-31.
56. Harnish D C, Albert L M, Leathurby Y, Eckert A M, Ciarletta A, Kasaian M, Keith J C Jr. (2004) Beneficial effects of estrogen treatment in the HLA-B27 transgenic rat model of inflammatory bowel disease. *Am J Physiol Gastrointest Liver Physiol,* 286:G118-25.
57. Harvell D M E, Strecker T E, Xie B, Pennington E L, McComb R D & Shull J D. (2002) Dietary energy restriction inhibits estrogen-induced mammary, but not pituitary, tumorigenesis in the ACI rat. *Carcinogenesis* 23: 161-169.
58. Hemminiki K & Thilly W G. (2004) Implications of results of molecular epidemiology on DNA adducts, their repair and mutations for mechanisms of human cancer. *IARC Sci Publ* 157: 217-235.
59. Hemminki K. DNA adducts in biomonitoring. (1995) *J Occup Environ Med* 37: 44-51.
60. Henderson B E, Ross R K & Pike M C. (1991) Towards primary prevention of cancer. *Science* 254: 1131-1138.
61. Hennekens C H, Buring J E, Manson J E, Stampfer M, Rosner B, Cook N R, (1996) Lack of effect of long-term supplementation with beta carotene on the incidence of malignant neoplasms and cardiovascular disease. *N Engl J Med,* 334: 1145-1149.

62. Hu W, Feng Z, Eveleigh J, Iyer G, Pan J, Amin S, Chung F L & Tang M S. (2002) The major lipid peroxidation product, trans-4-hydroxy-2-nonenal, preferentially forms DNA adducts at codon 249 of human p53 gene, a unique mutational hotspot in hepatocellular carcinoma. *Carcinogenesis* 23: 1781-1789.

63. Ikeda K & Inoue S. (2004) Estrogen receptors and their downstream targets in cancer. *Arch Histol Cytol* 67: 435-442.

64. Issacs J T. (1988) Inheritance of a genetic factor from the Copenhagen rat and the suppression of chemically induced mammary adenocarcinogenesis. *Cancer Res* 48: 2204-2213.

65. Jemal A, Murray T, Ward E, Samuels A, Tiwari R, Ghafoor A, Feuer E & Thun M J. Cancer Statistics 2005. *CA Cancer J Clin* 55: 10-30, 2005.

66. Jeyabalan J, Vadhanam M V, Ravoori S & Gupta R C. Sustained overexpression of CYP1A1 and 1B1 and steady accumulation of DNA adducts by low-dose, continuous exposure to benzo[a]pyrene by polymeric implants. *Chem. Res. Tox.* 24: 1937-1943, 2011.

67. Kelloff G J, Boone C W, Steele V E, Fay J R, Lubet R A, Crowell J A & Sigma C C. (1994) Mechanistic considerations in chemopreventive drug development. *J Cell Biochem Suppl* 20:1-24.

68. Kelsey J L & Bernstien L. Epidemiology and prevention of breast cancer. (1996) *Annu Rev Pub Hlth* 17: 47-67.

69. Kuiper G, Enmark E, Pelto-Huikko M, Nilsson S & Gustafsson J A. (1996) Cloning of a novel estrogen receptor expressed in rat prostate and ovary. *Proc Natl Acad Sci* 93: 5925-5930, 1996.

70. Lee A J, Cai M X, Thomas P E, Conney A H, Zhu B T. (2003) Characterization of the oxidative metabolites of 17beta-estradiol and estrone formed by 15 selectively expressed human cytochrome p450 isoforms. *Endocrinology.* 144:3382-98.

71. Lee C K, Son S H, Park K K, Park J H, Lim S S, Kim S H and Chung W Y. (2008) Licochalcone A inhibits the growth of colon carcinomas and attenuates cisplatin-induced toxicity without a loss of chemotherapeutic efficacy in mice. *Basics Clin. Pharmacol. Toxicxol.* 103, 48-54.

72. Lee M I, Cook N R, Manson J E, Buring J E and Hennekens C H. (1999) β-Carotene supplementation and incidence of cancer and cardiovascular disease: the women's health study. *J Natl Cancer Inst*, 91: 2102-2106.

73. Li J J, Li S A, Oberley T D & Parsons J A. (1995) Carcinogenic activities of various steroidal and nonsteroidal estrogens in the hamster kidney: relation to hormonal activity and cell proliferation. *Cancer Res* 55: 4347-4351.

74. Li S A, Liao J D & Li J J. (2000) Estrogen-induced breast cancer in female ACI rats. In: *Hormonal Carcinogenesis* (Eds. Li J J, Daling J R and Li S A), vol III, pp 178-188, Springer-Verlag, NY.

75. Li S A, Weroha S J, Tawfik O & Li J J. (2002) Prevention of solely estrogen-induced mammary tumors in female ACI rats by tamoxifen: evidence for estrogen receptor mediation. *J Endocrinol* 175: 297-305.

76. Liehr J G & Ricci M J. (1996) 4-Hydroxylation of estrogens as marker of human mammary tumors. *Proc Natl Acad Sci USA* 93: 3294-3296.

77. Liehr J G, Ricci M J, Jefcoate C R, Hannigan E V, Hokanson J A & Zhu B T. (1995) 4 Hydroxylation of estradiol by human uterine myometrium and myoma microsomes: implications for the mechanism of uterine tumorigenesis. *Proc Natl. Acad. Sci. USA,* 92: 9220-9224.

78. Liehr J G. (2000) Is Estradiol a genotoxic mutagenic carcinogen? *Endocrine Rev* 21: 40-54.

79. Majumder P K & Gupta M. (1998) Effect of seed extract of carrot (*Daucus carota* Linn.) on the growth of Ehrlich ascites tumors in mice. *Phytotherapy Research* 12: 584-585.

80. Malins D C & Haimanot R. (1991) Major alterations in the nucleotide structure of DNA in cancer of the female breast. *Cancer Res* 51: 5430-5432.

81. Malins D C, Polissar N L, Gunselman S J. (1996) Progression of human breast cancers to the metastatic state is linked to hydroxyl radical-induced DNA damage. *Proc Natl Acad Sci USA.,* 93, 2557-2563.

82. Mambo E, Gao X, Cohen Y, Guo Z, Talalay P & Sidransky D. (2003) Electrophile and oxidant damage of mitochondrial DNA leading to rapid evolution of homoplasmic mutations. *Proc Natl Acad Sci USA* 100: 1838-1843.

83. Marnett L J. Oxyradicals and DNA damage. (2000) *Carcinogenesis* 21: 361-370.

84. Martinez-Tome M, Jimenez A M, Ruggieri S, Frega N, Strabbioli R & Murcia M A. (2001) Antioxidant properties of Mediterranean spices compared with common food additives. *J Food Prot* 64:1412-1419.

85. McPherson K, Steel C M & Dixon J M. (2000) Breast cancer-epidemiology, risk factors, and genetics. *BMJ* 321: 624-628.

86. Meyskens F L and Szabo E. (2005) Diet and cancer: the disconnect between epidemiology and randomized clinical trials. *Cancer Epidemiol Biomarkers Prev.* 14: 1366-1369.

87. Morton C L & Houghton P J. (2007) Establishment of human tumor xenografts in immunodeficient mice. *Nature Protocols,* 2(2), 247-250.

88. Narod S A & Offit K. (2005) Prevention and management of hereditary breast cancer. *J Clin Oncol* 23: 1656-1663.

89. Nath R G, Ocando J E & Chung F-L. (1996) Detection of 1,$N^2$-propanodeoxyguanosine adducts as potential endogenous DNA lesions in rodent and human tissues. *Cancer Res* 56: 452-456.

90. Nesnow S, Ross J A, Mass M J & Stoner G D. (1998) Mechanistic relationship between DNA adducts, oncogene mutations, and lung tumorigenesis in strain A mice. *Exp Lung Res* 24: 395-405.

91. Newbold R R & Liehr J G. (2000) Induction of uterine adenocarcinoma in CD-1 mice by catechol estrogens. *Cancer Res* 60: 235-237.

92. Omenn G S, Goodman G E, Thornquist M D, Balmes J, Cullen M R, Glass A, Keogh J P, Meyskens F L, Valanis B, Williams J H, Barnhart S, Cherniack M G, Brodkin C A, Hammar S. (1996a) Risk factors for lung cancer and for intervention effects in CARET, the beta-carotene and retinol efficacy trial. *J Natl Cancer Inst,* 88: 1550-1559.

93. Omenn G S, Goodman G E, Thornquist M D, Balmes J, Cullen M R, Glass A, (1996b) Effects of a combination of beta carotene and vitamin A on lung cancer and cardiovascular disease. *N Engl J Med,* 334: 1150-1155.

94. Prall O W, Rogan E M & Sutherland R L. (1998) Estrogen regulation of cell cycle progression in breast cancer cells. *J Steroid Biochem Mol Biol,* 65: 169-174.

95. Pratt M A, Bishop T E, White D, Yasvinski G, Menard M, Niu M Y, Clarke R. (2003) Estrogen withdrawal-induced N F-kappaB activity and bc1-3 expression in breast cancer cells: roles in growth and hormone independence. *Mol Cell Biol,* 23:6887-900.

96. Randerath K, Randerath E, Zhou G & Donghui Li. (1999) Bulky endogenous DNA modifications (I-compounds)-possible structural origins and functional implications. *Mutat Res* 424: 183-194.

97. Ravoori S, Vadhanam M V, Davey, D D, Srinivasan C, Nagarajan B & Gupta R C. (2006) Modulation of novel DNA adducts during human uterine cervix cancer progression. *Int J Oncol* (in press).

98. Ray B K, Gao X, Ray A. (1994) Expression and structural analysis of a novel highly inducible gene encoding alpha 1-antitrypsin in rabbit. *J Biol Chem*, 269:22080-6.

99. Russo J, Yun-Fu H, Yang X & Russo I. (2000) Chapter 1: Developmental, cellular and molecular basis of human breast cancer. *J Natl Cancer Intst Monogr* 27: 17-37.

100. Satyanarayana S, Sushruta K, Sarma G S, Srinivas N & Subba R G V. (2004) Antioxidant activity of the aqueous extracts of spicy food additives—evaluation and comparison with ascorbic acid in in-vitro systems. *J Herb Pharmacother* 4: 1-10.

101. Scholen T & Gerdes J. (2000) The Ki-67 protein: from the known and the unknown. *J Cell Physiol* 182: 311-322.

102. Shang Y. (2006) Molecular mechanisms of oestrogen and SERMs in endometrial carcinogenesis. *Nat Rev Cancer,* 6:360-368.

103. Shaw J A, Udokang K, Mosquera J M, Chauhan H, Jones J L & Walker R A. (2002) Estrogen receptors alpha and beta differ in normal human breast and breast carcinomas. *J Pathol* 198: 450-457.

104. Shull J D, Spady T J, Snyder M C, Johansson S L & Pennington K L. (1997) Ovary-intact, but not ovariectomized female ACI rats treated with 17β-estradiol rapidly develop mammary carcinoma. *Carcinogenesis* 18: 1595-1601.

105. Smith W A & Gupta R C. (1996) Use of a microsome-mediated test system to assess efficacy and mechanisms of cancer chemopreventive agents. *Carcinogenesis* 17: 1285-1290.

106. Smith W A & Gupta R C. (1999) Determining efficacy of cancer chemopreventive agents using a cell-free system concomitant with DNA adduction, *Mutat Res* 425: 143-152.

107. Smith W A, Arif J M & Gupta R C. (2001a) 1,2-Dithiole-3-thione and its structural analogue oltipraz are potent inhibitors of dibenz[a,l]pyrene-DNA adduction in female Sprague-Dawley rats. *Int J Cancer* 91: 132-136.

108. Smith W A, Arif J M & Gupta R C. (1998) Effect of chemopreventive agents on microsome-mediated DNA adduction of the breast carcinogen dibenzo[a,l]pyrene. *Mutat Res* 412: 307-314.

109. Smith W A, Freeman J W & Gupta R C. (2001b) Effects of chemopreventive agents on DNA adduction induced by the potent mammary carcinogen dibenzo[a,l]pyrene in the human breast cells MCF-7. *Mutat Res* 480-481: 97-108.

110. Srinivasan P, Vadhanam M V, Arif J M & Gupta R C. (2002) A Rapid Screening Assay for Antioxidant Potential of Natural and Synthetic Agents in vitro. *Int J Oncol* 20: 983-986.

111. Srivastava K C. (1989) Extracts from two frequently consumed spices—cumin and turmeric-inhibit platelet aggregation and alter eicosanoid biosynthesis in human blood platelets. *Prostaglandins Leukot Essent Fatty Acids* 37: 57-64.

112. Steinmetz K A & Potter J D. (1991) Vegetables, fruit, and cancer. I. *Epidemiology. Cancer Causes Control*, 2: 325-57.

113. Stone J P, Holtzman S & Shellabarger C J. (1980) Synergestic interactions of various doses of diethylstilbestrol and X-irradiation on mammary neoplasia in female ACI rats. *Cancer Res* 40: 3966-3972.

114. Sun Y. (1990) Free radicals, antioxidant enzymes, and carcinogenesis. *Free Radic Biol Med* 8: 583-599.

115. Teyssier C, Belguise K, Galtier F and Chalbos D, (2001) Characterization of the physical interaction between estrogen receptor a and JUN proteins. *J Biol Chem* 276: 36361-36369.

116. Todorovic R, Devanesan P, Higginbotham S, Zhao J, Gross M L, Rogan E G & Cavalieri E L. (2001) Analysis of potential biomarkers of estrogen-initiated cancer in the urine of Syrian golden hamsters treated with 4-hydroxyestradiol. *Carcinogenesis*, 22: 905-911.

117. Turan V K, Sanchez R I, Li J J, Li S A, Reuhl K R, Thomas P E, Conney A H, Gallo M A, Kauffman F C & Mesia-Vela S. (2004) The effects of steroidal estrogens in ACI rat mammary carcinogenesis: 17β-estradiol, 2-hydroxyestradiol, 4-hydroxyestradiol, 16α-hydroxyestradiol and 4-hydroxyestrone. *J Endocrin* 183: 91-99.

118. Uma Pradeep K, Geervani P & Eggum B O. (1993) Common Indian spices: nutrient composition, consumption and contribution to dietary value. *Plant Foods Hum Nutr* 44: 137-148.

119. Vadhanam M V, Ravoori S, Sahoo S, Srinivasan C & Gupta R C. (2006) An improvised model for estrogen-mediated mammary tumors in aci rats. *Proc Am Assoc Cancer Res* 47: Abst #1771.

120. Weitberg A B and Corvese D. (1997) Effect of vitamin E and beta-carotene on DNA strand breakage induced by tobacco-specific nitrosamines and stimulated human phagocytes. *J Exp Clin Cancer Res,* 6:11-4.

121. Willett W C. (2005) Diet and cancer. *J Am Med. Assoc.* 293: 233-234.

122. Yu L L, Zhou K K & Parry J. (2005) Antioxidant properties of cold-pressed black caraway, carrot, cranberry, and hemp seed oils. *Food Chem* 91: 723-729.

123. Yun J M, Afaq F, Khan N & Mukhtar H. (2009) Delphinidin, an anthocyanidin in pigmented fruits and vegetables, induces apoptosis and cell cycle arrest in human colon cancer HCT116 cells. *Mol. Carcinog.* 48, 260-270.

124. Zhang S, Hunter D J, Forman M R, Rosner B A, Speizer F E, Colditz G A, Manson J E, Hankinson S E, Willett W C. (1999) Dietary carotenoids and vitamins A, C, and E and risk of breast cancer. *J. Natl. Cancer Inst.* 91: 547-556.

125. U. S. Pat. No. 5,326,902.

126. U. S. Pat. No. 5,234,933.

127. International Application Publication No. WO 93/25521.

128. Berkow, et al., (1997) *The Merck Manual of Medical Information*, Home ed. Merck Research Laboratories, Whitehouse Station, N.J.

129. Goodman, et al., (2006) *Goodman & Gilman's the Pharmacological Basis of Therapeutics,* 11th ed. McGraw-Hill Health Professions Division, New York.

130. Ebadi. (1998) *CRC Desk Reference of Clinical Pharmacology*. CRC Press, Boca Raton, Fla.

131. Katzung. (2007) *Basic & Clinical Pharmacology,* 10th ed. Lange Medical Books/McGraw-Hill Medical Pub. Division, New York.

132. Remington, et al., (1990) *Remington's Pharmaceutical Sciences,* 18th ed. Mack Pub. Co., Easton, Pa.

133. Speight, et al., (1997) Avery's Drug Treatment: A Guide to the Properties, Choice, Therapeutic Use and Economic Value of Drugs in Disease Management, 4th ed. Adis International, Auckland/Philadelphia.

134. Duch, et al., (1998) *Toxicol. Lett.* 100-101:255-263.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A composition, comprising:
    a biocompatible polymeric matrix incorporating an effective amount of a phytochemical agent; and
    a polymeric coating surrounding the biocompatible polymeric matrix,
    wherein the composition releases a controlled low dose of the phytochemical agent over a time period, and
    wherein the polymeric coating is comprised of polycaprolactone.

2. The composition of claim 1, wherein the time period is at least about 18 months.

3. The composition of claim 1, wherein the biocompatible polymeric matrix is comprised of a polymer selected from the group consisting of polycaprolactone, cyclodextrin, F68, polyethylene glycol, and combinations thereof.

4. The composition of claim 1, wherein the biocompatible polymeric matrix comprises polycaprolactone in combination with a second polymer.

5. The composition of claim 4, wherein the second polymer is selected from the group consisting of cyclodextrin, F68, and polyethylene glycol.

6. The composition of claim 4, wherein the polycaprolactone and the second polymer are combined in a ratio of about 4:1 or about 9:1.

7. The composition of claim 1, wherein the biocompatible polymeric matrix comprises polycaprolactone and F68 in a ratio of about 4:1.

8. The composition of claim 1, wherein the biocompatible polymeric matrix comprises polycaprolactone and polyethylene glycol in a ratio of about 65:35.

9. The composition of claim 1, wherein the phytochemical agent is curcumin.

10. The composition of claim 1, wherein the biocompatible polymeric matrix is biodegradable.

11. The composition of claim 1, wherein the phytochemical agent comprises about 2% to about 50% of the polymer weight.

12. The composition of claim 1, wherein the phytochemical agent is selected from the group consisting of curcumin, green tea polyphenols, punicalagin, diindolylmethane, oltipraz, tocotrienol, tocopherol, plumbagin, cyanidin, delphinidin, lycopene, lupeol, curcurbitacin-B, Withaferin A, indole-3-carbinol, genestein, equol, resveratrol, co-enzyme Q-10, ellagic acid, petunidin, malvidin, peonidin, fennel extract, and combinations thereof.

13. The composition of claim 1, wherein the phytochemical agent is a combination of:
    oltipraz and curcumin;
    curcumin, ellagic acid, co-enzyme Q-10, and lycopene;
    curcumin, green tea polyphenols, diindolylmethane, and punicalagin;
    delphinidin, petunidin, malvidin, peonidin, and cyanidin; or
    punicalagin and delphinidin.

14. The composition of claim 13, further comprising a second biocompatible polymeric matrix, wherein the second biocompatible polymeric matrix incorporates at least one phytochemical agent.

15. The composition of claim 1, further comprising an effective amount of an anti-inflammatory agent incorporated into the biocompatible polymeric matrix or a second biocompatible polymeric matrix.

16. The composition of claim 1, further comprising an effective amount of a chemotherapeutic agent incorporated into the biocompatible polymeric matrix or a second biocompatible polymeric matrix.

17. The composition of claim 1, wherein the polymeric coating comprises one or more layers.

18. The composition of claim 17, wherein the one or more layers comprise about 5 to about 40 layers.

19. The composition of claim 1, wherein the biocompatible polymeric matrix is in the form of a coating.

20. The composition of claim 19, wherein the coating comprises about 20 to about 40 layers.

* * * * *